US006913877B1

(12) United States Patent
Chaplen et al.

(10) Patent No.: US 6,913,877 B1
(45) Date of Patent: Jul. 5, 2005

(54) METHODS FOR DETECTING BIOACTIVE COMPOUNDS

(75) Inventors: Frank W. R. Chaplen, Albany, OR (US); William H. Gerwick, Corvallis, OR (US); Goran Jovanovic, Corvallis, OR (US); Wojtek Kolodziej, Corvallis, OR (US); Jim Liburdy, Philomath, OR (US); Phil McFadden, Corvallis, OR (US); Brian Kevin Paul, Corvallis, OR (US); Thomas K. Plant, Philomath, OR (US); Janine E. Trempy, Corvallis, OR (US); Corwin Willard, Monroe, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 89 days.

(21) Appl. No.: 10/024,654

(22) Filed: Dec. 17, 2001

Related U.S. Application Data

(63) Continuation of application No. 09/952,216, filed on Sep. 12, 2001, now abandoned.
(60) Provisional application No. 60/232,171, filed on Sep. 11, 2000.

(51) Int. Cl.[7] .......................... A61K 35/60; A61K 9/14; C12Q 1/00; C12Q 1/02

(52) U.S. Cl. ....................... 435/4; 435/40.5; 435/29; 424/489; 424/520

(58) Field of Search ............................... 424/520, 489; 435/29, 40.5, 4

(56) References Cited

U.S. PATENT DOCUMENTS

| 4,401,755 A | 8/1983 | Weaver |
| 4,985,353 A | 1/1991 | Elving |
| 5,462,856 A | 10/1995 | Lerner et al. |
| 5,641,644 A | 6/1997 | Klebe |
| 5,721,135 A | 2/1998 | Thastrup et al. |
| 5,900,361 A | 5/1999 | Klebe |
| 5,919,646 A | 7/1999 | Okun et al. |
| 5,998,212 A | 12/1999 | Corio et al. |

OTHER PUBLICATIONS

Paul, Vignais; "Photo phosphorylation in bacterial chromatophores entrapped in alginate gel improvement of the physical and biochemical properties of gel beads with barium as gel inducing agent", Enzyme and Microbial Technology, 1980, vol. 2, No. 4, p. 281–87.*
Kotz et al., "Intracellular calcium and cAMP regulated directional pigmetn movements in teleost erythrophores", J Cell Biology, 1994, vol. 124, No. 4, pp. 463–474.*
Karlsson et al., "The melanophore aggregating response of isolated fish scares: a very rapid and sensitive diagnosis of whooping cough," *FEMS Microbiology Letters* 82:169–176 (1991).
Karlsson et al., "The Effect of Pertussis Toxin on Alpha–2–Adrenoceptor–Mediated Pigment Migration in Fish Mediated Pigment Migration in Fish Melanophores," *Life Science* 37:1043–1949 (1985).
Karlsson et al., "Pronounced Supersensitivity of Postjunctional Alpha Adrenoceptors after Denervation of Fish Melanophores," *The Journal of Pharmacology and Experimental Therapeutics* 246:345–351 (1988).
Land, M.F., "The Physics and Biology of Animal Reflectors,"0 *Dept. of Physiology, University of California, Berkeley*, pp. 75–105.
Lu et al., "Single–Molecule Enzymatic Dynamics," *Science* 282:1877–1881 (Dec. 1998).
Maeno et al., "Adrenergic Mechanisms Associated with the Movement of Platelets and Iridophores from the Freshwater Goby, Odontobutis Obscura," *Comp. Biochem. Physiol.* 102C:233–237 (1992).
Martensson, et al., "Denervation of Pigment Cells Lead to a Receptor that is Ultrasensitive to Melatonin and Noradrenaline," *Life Sciences* 18:1575–1582 (1997).
Oshima and Nagaisha, "Study of the Motile Mechanism in Neon Tetra (Paracheirodon innesi) Iridophores," *Comp. Biochem. Physiol.* 102A:273–278 (1992).
Potenza et al., "A Method for Evaluating the Effects of Ligands upon $G_S$ Protein–Coupled Receptors Using a Recombinant Melanophre–Based Bioassy," *Anal. Biochem.* 206:315–322 (1992).
"Axiom Biotechnologies Issued U.S. Patent on High Throughput Pharmacy System (HT–PS™)" Axiom Biotechnologies, Inc., Apr. 3, 2000, http://www.axiombio.com/home.html.
Clothier et al., "Light–induced colour changes by the iridophores of the Neon tetra, Paracheirodon innesi," *J. Cell Sci.* 88:663–668 (1987).

(Continued)

*Primary Examiner*—Leon B. Lankford, Jr.
*Assistant Examiner*—Ruth A. Davis
(74) *Attorney, Agent, or Firm*—Klarquist Sparkman, LLP

(57) ABSTRACT

Methods of detecting bioactive compounds include exposing compounds to one or more classes of chromatophores and measuring or sensing associated changes in one or more of the chromatophores. Representative methods permit identification and quantification of neurotransmitters, toxins, hormones, and chemical warfare agents with or without prior knowledge of the content of a sample. In some examples, chromatophores based on Betta fish are used. Cytosensor apparatus using such chromatophores include means for exposing chromatophores to a sample and optical detection systems for assessing changes in chromatophore optical properties. Compounds can be identified or quantified based on a red-green-blue or hue saturation-value representations of transmitted or reflected light or based on other characterizations of transmitted or reflected light.

22 Claims, 35 Drawing Sheets

OTHER PUBLICATIONS

Danosky et al., "Biosensors based on the chromatic activities of living, naturally pigmented cells: digital image processing of the dynamics of fish melanophores," *Biosensors & Bioelectronics* 12:925–936 (1997).

Elwing et al., "Fish Scales as Biosensors for Catecholamines," *Biosensors & Bioelectronics* 5:449–459 (1990).

Fujii, R., "Coloration and Chromatophores" in *The Physiology of Fishes,* D.H. Evans, ed., (CRC Press, 1993).

Fujii et al, "Control of Chromatophore Movements in Telecost Fishes," *Zoological Science* 3:13–47 (1986).

Fujii et al., "Cytophysiology of Fish Chromatophores," *International Review of Cytology* 143:191–255 (1993).

Jayawickreme et al., "Creation and functional screening of a multi–use peptide library," *Proc. Natl. Acad. Sci. USA* 91:1614–1618 (1994).

Jayawickreme et al. "Discovery and Structure–Function Analysis of α–Melanocyte–stimulating Hormone Antagonists," *J. Biological Chemistry* 269:29846–29854 (1994).

Quillan et al., "Combinatorial diffusion assay used to identify topically active melanocyte–stimulating hormone receptor antagonists," *Proc. Natl. Acad. Sci USA* 92:2894–2898 (1995).

Rohrlich, S.T., "Fine Structural Demonstration of Ordered Arrays of Cytoplasmic Filaments in Vertebrate Iridophores," *J. Cell Bio.* 62:295–304 (1974).

Svensson et al., "Melanophores in Isolated Scales of *Labrus Berggylta* (Ascanius): Innervation and $Alpha_2$–Adrenoceptor–Mediated Pigment Aggregation," *Comp. Biochem. Physiol.* 930:247–251 (1988).

Yamada et al., "Autoradiographic Demonstration of Adrenergic Innervation to Scale Melanophores of a Teleost Fish, *Oryzias latipes,*" *J. Exp. Zoology* 229:73–80 (1984).

"The New English Bible", Oxford University, Genesis, pp. 33–34, (1970). (See especially p. 33, line 46 through p. 34, line 25).

\* cited by examiner-

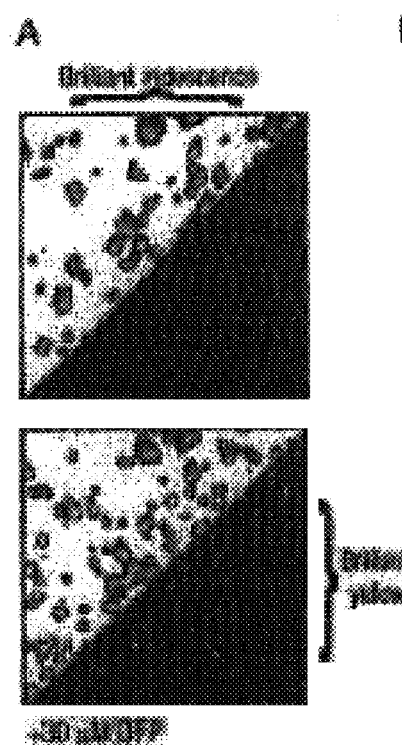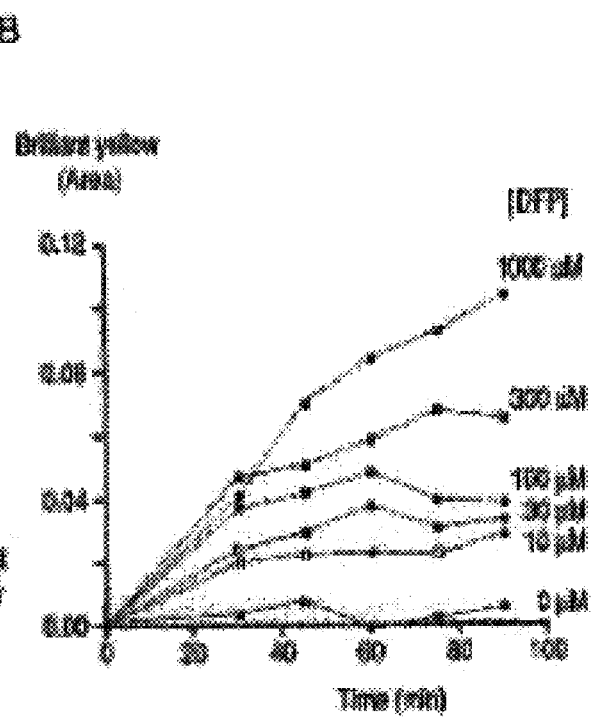
FIG. 5A
FIG. 5B

Before adding bacteria    After adding bacteria
FIG. 7A 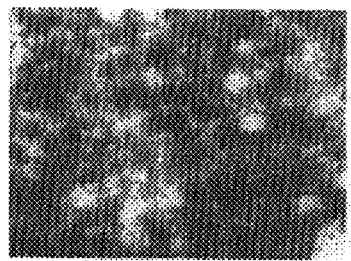 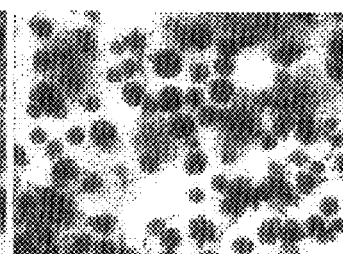 FIG. 7B
Strain 1
Strain 2
FIG. 8A 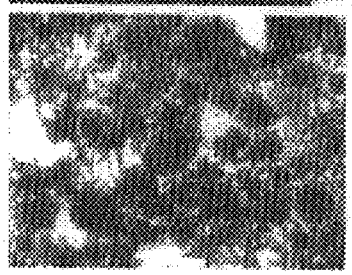 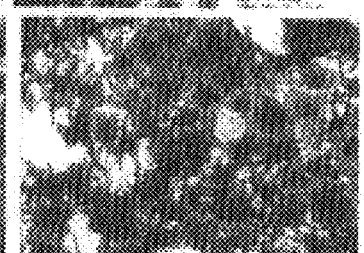 FIG. 8B
Strain 3
FIG. 9A  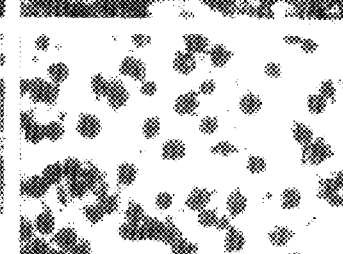 FIG. 9B
Strain 4
FIG. 10A 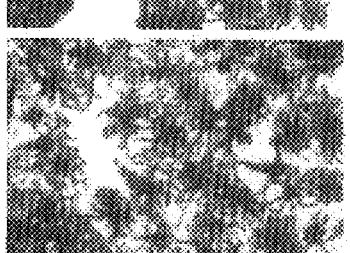  FIG. 10B
Strain 5
FIG. 11A 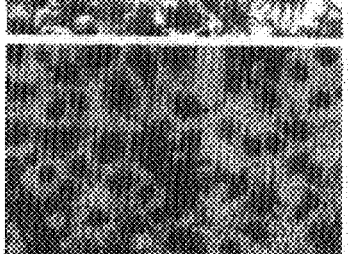 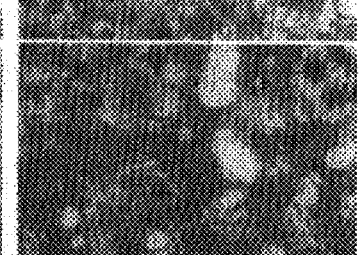 FIG. 11B

FIG. 13

| | Agent | Chemical Type | Effective dose | Direct Effects | Challenge A (norepinephrine) | Challenge B (forskolin) |
|---|---|---|---|---|---|---|
| Control | None | -- | -- | | | |
| I | DFP Mipafox Paraoxon | phosphorofluoridate phosphorofluorodithioate phosphate | ppm | | | |
| II | EPN | salicyl fluoride phosphorothioate | ppb | | | |
| III | Naviraphos Dichlorvos | phosphate phosphate | ppt | | | |
| IV | Trichlorfon | phosphonate | ppt | | | |
| V | Chlorpyrifos Fenthiothion Morphos Carbaryl Methomyl 2,5 Hexanedione Acrylamide | phosphorothioate phosphorothioate phosphorothioate carbamate carbamate diketone amide | ND | | | |

100 microns

Hardware construction for the encapsulation of SOS sensor cells.

Extruder hardware (assembled)

Air-flow adjustment mechanism

FIG. 19A  
(+) Ca²⁺ applied as $(+) Ca^{2+}$
Before
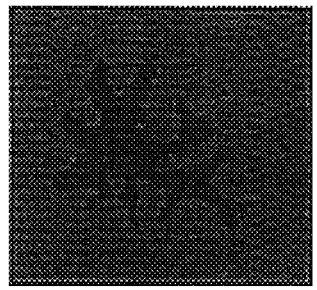
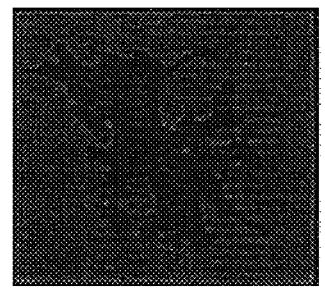
FIG. 20A  
$(-) Ca^{2+}$
After 10nM Norepinephrine
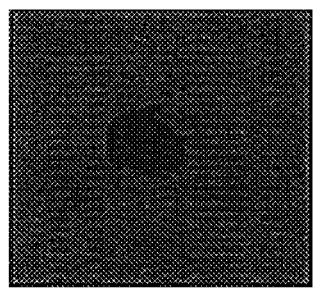
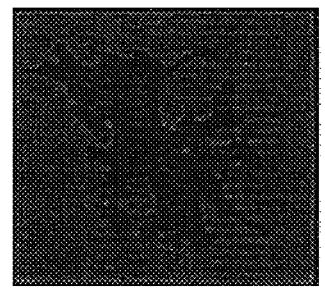
FIG. 19B      FIG. 20B

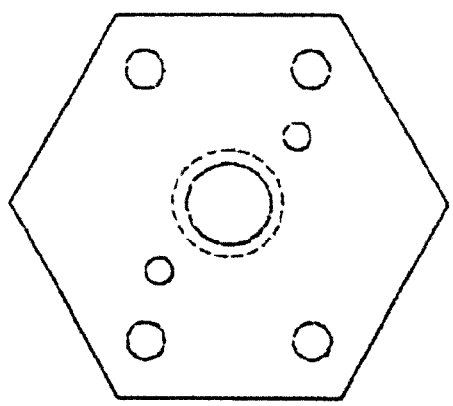
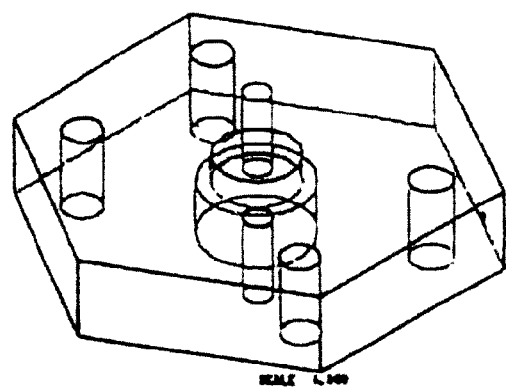
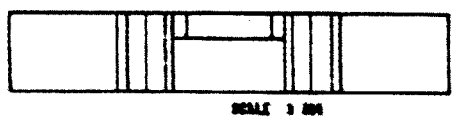
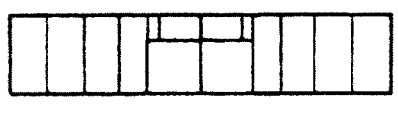
FIG. 27

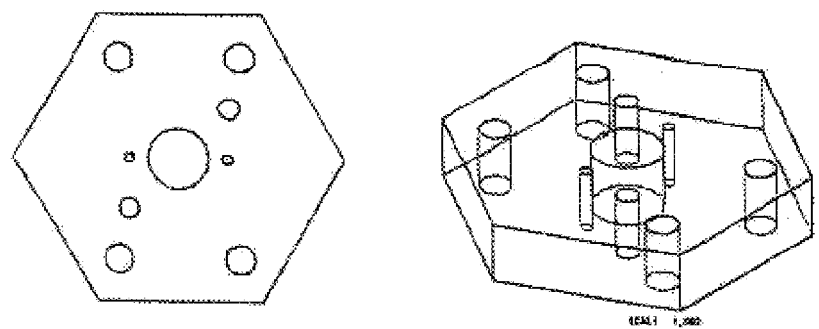
FIG. 28A
FIG. 28B
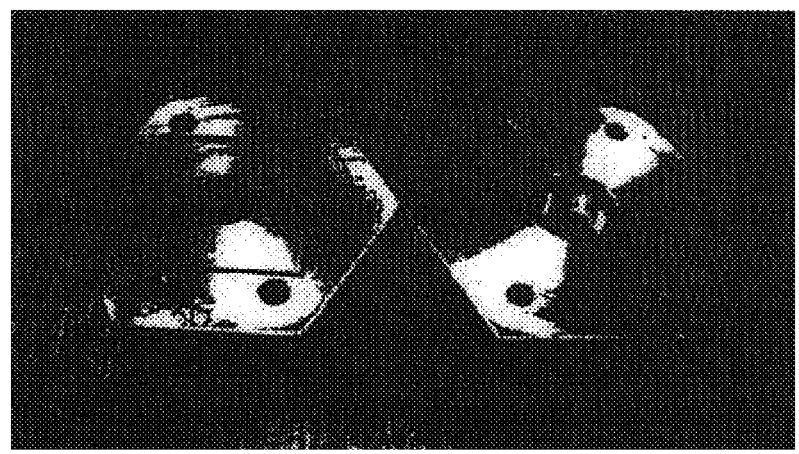

Magnetic Field is OFF
Solenoid

Magnetic Field is ON
Solenoid

METHODS FOR DETECTING BIOACTIVE COMPOUNDS

RELATED APPLICATIONS

This application is a continuation of U.S. application Ser. No. 09/952,216, filed Sep. 12, 2001 now abandoned, which claims the benefit of U.S. Provisional Application No. 60/232,171, filed Sep. 11, 2000, both of which are incorporated herein by reference.

GOVERNMENT LICENSE RIGHTS

The U.S. Government has a paid-up license in this invention and the right in limited circumstances to require the patent owner to license others on reasonable terms as provided for by the terms of Contract No. N66001-99-C-8631 and Grant No. N00014-96-1-0566 awarded by the Defense Advanced Research Projects Agency and the Office of Naval Research, respectively.

FIELD OF THE INVENTION

The invention pertains to methods and apparatus for detecting bioactive compounds using chromatophores.

BACKGROUND AND SUMMARY OF THE INVENTION

Biosensors use biological elements to detect and quantify analytes and have applications in toxicology, pharmacology, medical diagnostics, and environmental monitoring. Biosensors that include living cells as sensing elements are referred to as cytosensors. Cytosensors are function-based sensors because they typically detect substances based on the effect of an analyte on functional activities of sensor cells. Sensor cells provide a large number of functional targets for detecting biologically active agents. These functional targets (such as enzymes, receptors, membranes, cytoskeletal structures, cellular organelles, second messenger signals, cytoplasmic elements and others) may be partly specified or unspecified at the time a measurement is performed and can remain unspecified even for a test standardized for a particular application. In addition, classes of analytes can be identified with or without identification of any specific analytes. For example, irritants in cosmetics can be detected by a standardized reaction with a cytosensor without knowledge of a reaction mechanism. Such a test need not identity any specific irritants but may indicate the presence of irritants. Such methods can serve as alternatives to animal testing in applications such as food and drug testing. Because cytosensors are based on living cells, cytosensor measurements can be configured to replace live animal tests.

The living cells used in cytosensors must be maintained for sufficiently long time periods for performance of cytosensor tests and cells that exhibit longevity and ruggedness after extraction are particularly useful. The cells must also be configured so that cell changes in response to analyte exposures can be detected.

Okun et al., U.S. Pat. No. 5,919,646, describes an apparatus and method for real-time measurement of cellular response of a test compound. Elving, U.S. Pat. No. 4,985,353, discloses detection of a toxin produced by *Bordetella pertussis* based on a color change in a fish scale. Lerner et al., U. S. Pat. Nos. 5,462,856 and 6,051,386 disclose methods for identifying chemicals that act as agonists for a G-protein coupled cell surface receptor. Danosky and McFadden, Biosensors & Bioelectronics 12:925–936 (1997), describes biosensors based on the chromatic activities of fish melanophores. Weaver, U.S. Pat. No. 4,401,755, discloses a process for encapsulating a biologically active compound with a material, allowing the material to gel, and then detecting a response.

Living cells can be used to identify or quantify bioactive agents in samples based on changes in, for example, cell morphology and/or physiology. Such changes can be directly detected or detected with the aid of instrumentation. For example, cells can be arranged so that visual inspection is adequate to identify the presence of bioactive agents, or, alternatively, an optical measurement system or other instrumentation can be provided.

In representative embodiments, methods of using at least one chromatophore to detect bioactive agents are provided. These methods involve placing the chromatophore in functional contact with a sample containing at least one suspected bioactive agent. Functional contact in this context means than the chromatophore is placed in a position relative to the sample such that the chromatophore can react to the various bioactive agents in the sample. Hence, the term has a broader meaning that physical contact.

In other representative examples, living cells used as sensors include chromatophores that exhibit changes in color, morphology, and/or distribution of pigment in response to selected analytes. These changes are monitored with or without additional instrumentation.

According to another aspect of the invention, encapsulated chromatophores are configured for the detection of bioactive agents. In a particular example, encapsulated chromatophores are at least partially surrounded in a coating configured to maintain the chromatophores in a suitable environment and in functional contact with test samples.

In further embodiments, cytosensors are configured to detect samples that include a variety of different types of compounds. For example, samples can contain organisms such as bacteria, fungi, viruses, plants, and animals. Samples can also contain neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. Test kits for use in detecting bioactive agents are provided. In some examples, the test kits include a nutrient solution, at least one chromatophore, and a positive control solution.

Cytosensors are configured to expose chromatophores and to detect changes in the chromatophores. The cytosensors include a reaction chamber configured to retain chromatophores and an optical detection system situated to detect associated optical changes. A signal processing system detects chromatophore changes based on a red-green-blue or hue-saturation-value color representation of a transmitted or reflected optical flux that is received by the optical detection system. In other examples, such detection systems and methods are configured to detect changes in the coloration of cells other than chromatophores.

Cytosensors include a vessel defining an inlet configured to receive at least one bioactive material or test compound. A mixing zone is provided that is fluidically coupled to receive the chromatophores and the test compound from the inlet. The mixing zone is configured to expose the chromatophores to the test compound. The cytosensor can also include means for mixing the bioactive unit with the chromatophores, and a sensor for detecting changes in chromatophore cell properties (such as, for example, color or other optical properties, electrical properties such as capacitance or conductivity or other properties). The cytosensors described herein can also contain at least one signal processing system coupled to the sensor and at least one processor that converts a digital output from the signal processing system into an analytical result.

Fish chromatophores of varies species of fish can be used. Examples include freshwater zebrafish, south American cichlids, African cichlids, saltwater damsels, goldfish, gouramis, and other species. In addition, chromatophores can be based on fish scales, fin tissues, and the like. For use in cytosensors, encapsulation of chromatophores or analytes is unnecessary.

Cytosensors are configured so that chromatophores can detect agents that act on functional targets selected from a group consisting of enzymes, receptors, membranes, cytoskeletal structures, cellular organelles, second messenger signals, cytoplasmic elements and the like at a molecular and/or a cellular level. Such targets may be partly or wholly undefined at the time the measurement is performed. These targets-trigger a detectable response to an active compound and can remain undefined even when a test is commonly used or is standardized for a particular industrial, commercial, or academic application.

These and other features of the invention are set forth below with reference to the accompanying drawings.

BRIEF DESCRIPTION OF THE DRAWINGS

FIG. 5A illustrates a segmentation of colors from iridophore patches before (top) and after (bottom) exposure to DFP.

FIG. 5B is a graph of response of the iridophore patch of FIG. 5A as a function of time to various concentrations of DFP.

FIGS. 7A–11A illustrate the appearance of *Betta splendens* chromatophores prior to exposure and FIGS. 7B–11B illustrate the appearance of *Betta splendens* chromatophores after exposure, respectively, to various strains of bacteria.

FIG. 13 illustrates the appearance of a scale that includes several types of chromatophores after exposure to one or more analytes.

FIGS. 19A–19B are photographs of an erythrophore prior to and after exposure to NE in a solution containing calcium ions.

FIGS. 20A–20B are photographs of an erythrophore prior to and after exposure to norepinephrine in a solution lacking calcium ions.

FIG. 27 is a schematic diagram of one portion of a fluid interconnect.

FIGS. 28A–28B illustrate another portion of the fluidic interconnect of FIG. 27.

FIGS. 38A–38D are photographs of masks for a round coil and a square coil, respectively.

DETAILED DESCRIPTION

Figure 1A:
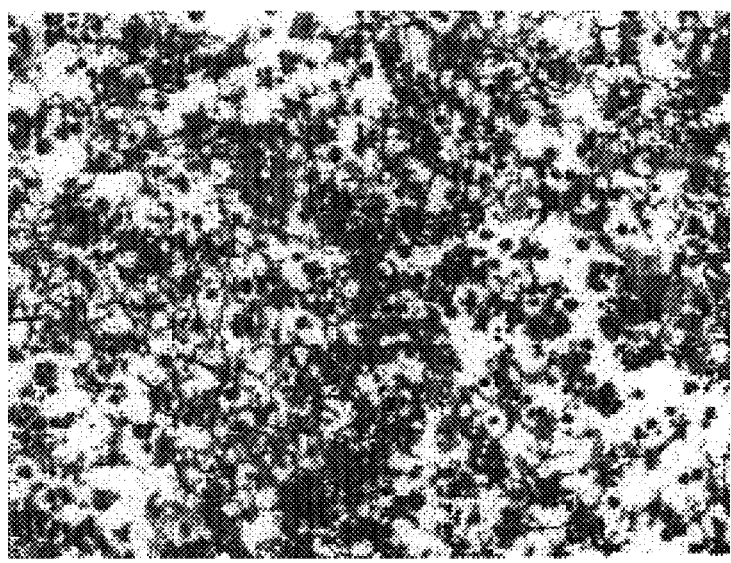
FIGS. 1A–1B illustrate pigment aggregation in chromatophores obtained from fish of the genus Betta prior to and after exposure to norepinephrine, respectively.

For convenience, several terms used in describing examples are defined. A bioactive material is a material that elicits a physiological, morphological, or other response from a living cell either alone or in combination with other materials. An analyte is a substance to be detected or quantified and in some examples is a bioactive agent that is a chemical agent or a living organism such as fungi, bacteria, virus, molds, protists, animal cells, or other animals that elicits a response from a living cell. A cytosensor is an apparatus that uses living cells to detect analytes. In some examples, a cytosensor includes at least one cell and changes produced in the cell by an analyte or combination of analytes are detected by methods such as visual inspection, or other methods. In other examples, changes produced in response to exposure to an analyte are detected by a statistical analysis of cell properties.

Chromatophores are naturally colored cells in the skin of cold-blooded animals such as fish, amphibians, and reptiles. The optical properties of chromatophores can change and such changes are part of some well known phenomena, such as the color changes exhibited by chameleons and flounders. These color changes can be produced by movement of colored organelles within the cytoplasm of the chromatophore. For example, a chromatophore can become lighter in appearance as result of transport of pigment so that the pigment aggregates in a small region near the center of the chromatophore. An overall darkening of a chromatophore can be produced by transport of pigment to zones that are dispersed throughout the cell.

The optical properties of some chromatophores are determined by organelles that include light-absorbing pigments such as melanins (black), pteridines (red), and carotenes (yellow). The optical properties of other chromatophores are based on organelles that have periodic internal structures that iridescently interfere with incident light causing selective reflection of certain colors and transmission of other colors. Such organelles are referred to as iridescent and can change their hue, and hence the hue of the cell, in response to various stimuli. Any single chromatophore generally contains one type of organelle so that its appearance is determined by this type of organelle.

Classes of chromatophores are commonly assigned names based on a dominant color, for example, melanophores (black), erythrophores (red), and iridophores (yellow and/or iridescent). Subtypes of these classes include bluish-black melanophores, yellowish-red erythrophores, and others. The complex spectral properties of various animal skins are typically produced by combinations of chromatophores of several types.

In an intact animal, chromatophore appearance is regulated by the nervous and endocrine systems via the actions of neurotransmitter and hormone molecules that act through transmembrane receptor proteins on the surface of the chromatophore. The binding of such molecules triggers a cascade of intracellular processes that produces a color change in the chromatophore. With chromatophores extracted from animals, changes in chromatophore appearance in response to exposure to analytes of known or unknown composition can be detected visually or quantified with an optical detection system. Representative detection systems include light microscopes or other optical systems such as those described below.

One source of chromatophores is *Betta splendens* fish. These fish are readily available in many colors, and the fins typically include chromatophores of various types. Male *Betta splendens* are generally more noticeably colored and hence are superior to females as a source of chromatophores, but female *Betta splendens* fish can be used. Chromatophores can also be obtained from other fish species.

Betta fish are customarily classified as Asian labyrinth fishes in the family Belontiidae. The family Belontiidae includes five subfamilies (Belontinae, Macropodinae, Trichogasterinae, Sphaerichthyinae, and Ctenopinae). The subfamily Ctenopinae includes the genus Betta (see, for example, H. Pinter, *Labyrinth Fish,* Barron's Educational Press, New York (1986)). Species included in the genus Betta that are listed by Pinter include: B. (Schaumnestbauer); *B. bellica* Sauvage, 1884; *B. coccina* Vierke, 1979; *B. fasciata* Regan, 1909; *B. foerschi,* Vierke, 1979; *B. imbellis I.adiges,* 1975; *B. rmaragdina I.adiges,* 1972; *B. splendens* Regan, 1909; Betta (Maulbruter); *B. avabatoidcs* Bleeker, 1850; *B. balunga* Herre, 1940; *B. brederi* Myers, 1935; *B. macractoma* Regan, 1909; *B. picta* (Cuvier u. Valenciennes, 1846); *B. pugnax* (Cantor, 1850); *B. rubra* Perugia, 1893; *B. taeniata* Regan, 1909; and *B. unimaculata* (Popta, 1905). Betta fish and fish of the whole subfamily Ctenopinae are sources of useful chromatophores. Some useful fish include freshwater zebrafish, south American cichlids, African cichlids, saltwater damsels, goldfish, gouramis, and others.

Chromatophores can be used to test a wide range of analytes for the presence of bioactive compounds, organisms, or toxins, and prior knowledge of the type or structure of the bioactive compound is unnecessary. For example, chromatophores respond to analytes derived from medical, forensic, or pharmaceutical specimens such as neurotransmitters, norepinephrine, adenosine, dopamine and analogs thereof such as LSD, cocaine, serotonin analogs, hormones such as MSH (1 nM), melanophore concentrating hormone (MCH) and analogs thereof, intracellular signal transduction agents such as nitric oxide, forskolin (10 mM), cAMP, cGMP, calcium ion, protein kinase A, and analogs thereof; pharmaceutically active agents such as caffeine (100 $\mu$M), alpha-2 adrenergic agonists (yohimbine), pertussis toxin, dibutyryl cAMP, dibutyryl cGMP, including prescription drugs, off-the-shelf drugs, and illicit drugs; toxic agents such as chemical warfare agents (for example, diisopropyl fluorophosphate (DFP)); agricultural chemicals such as paroxon; chemical toxins in food and water, biological toxins in food and water such as *cholera* toxin; toxin-producing bacteria (*Bacillus cereus, Salmonella enteriditis Escherichia coli* 0157:H7, *Vibrio cholera*); bacterial cells, fungal cells, yeast, protists, and animal cells, such as PC12 neuronal cells.

Figure 1B:
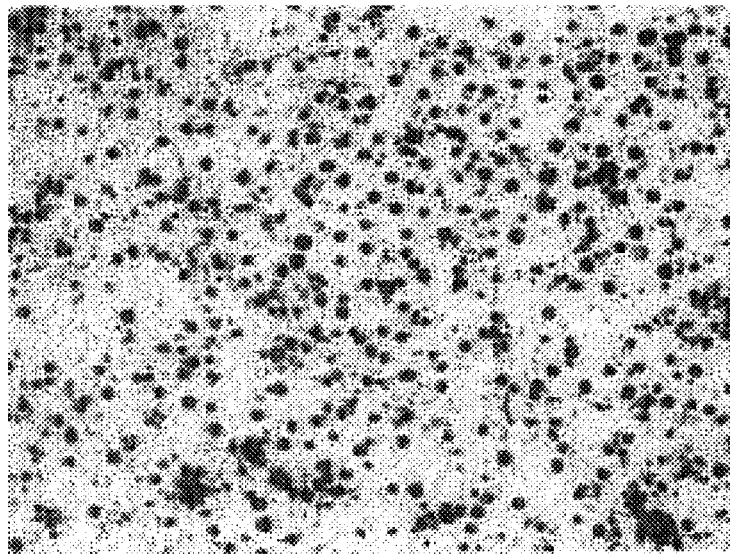
Figure 2A:
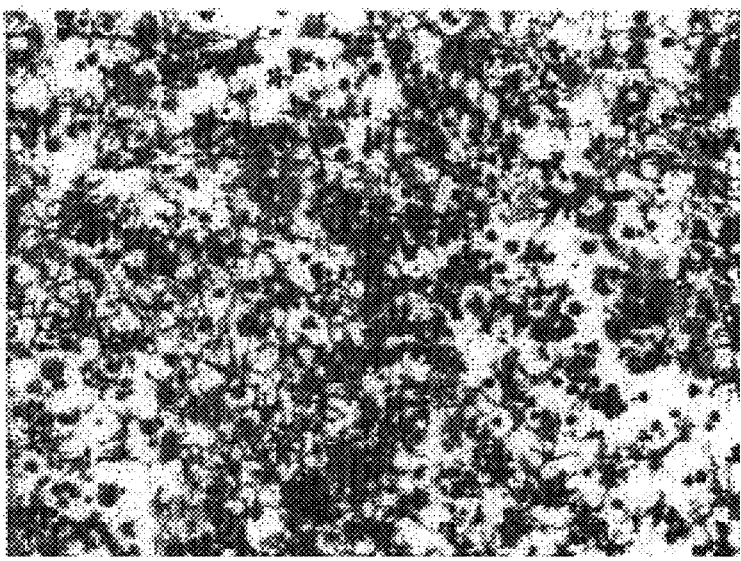
FIGS. 2A–2B illustrate the appearance of Betta chromatophores prior to and after an exposure of a few hours duration to *cholera* toxin (CTX).
Figure 2B:
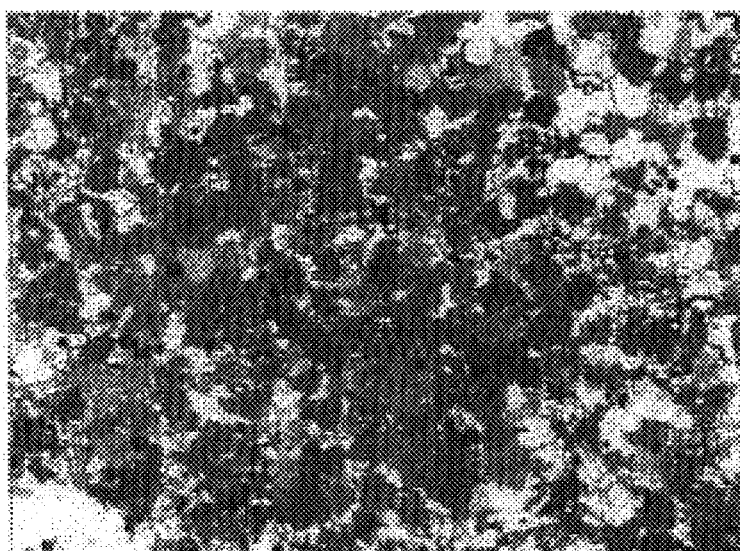

Chromatophore response to some of these analytes is illustrated in the accompanying figures. FIGS. 1A–1B illustrate the appearance of Betta chromatophores before exposure and after a few seconds of exposure, respectively, to a 1 nM solution of norepinephrine. Referring to FIG. 1B, aggregation of chromatophore pigment is apparent FIGS. 2A–2B illustrate chromatophore appearance before and after, respectively, exposure to a 100 pM solution of *cholera* toxin. Pigment aggregation is evident.

Figure 3A:
FIGS. 3A–3B illustrate the appearance of a jewel cichlid scale (from *Hemichromis bimaculatus*) before and after, respectively, exposure to diisopropyl fluorophosphate (DFP).
Figure 3B:
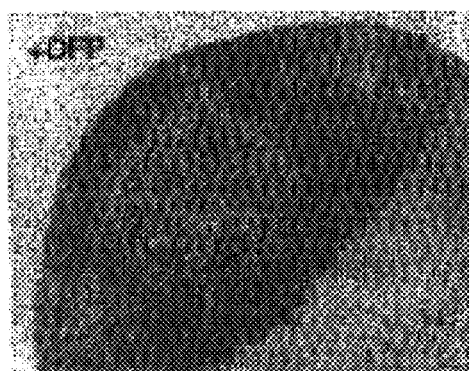
Figure 3C:
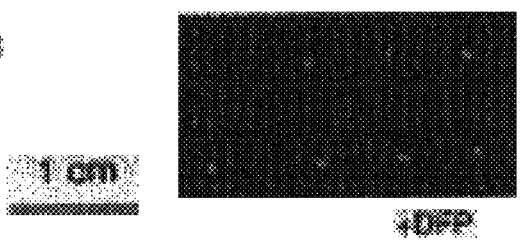
FIG. 3C illustrates eight scales from a jewel cichlid viewed in reflected light. Four scales were exposed to DFP and four scales were unexposed.

FIGS. 3A–3B illustrate the appearance of a jewel cichlid scale from *Hemichromis bimaculatus* before and after exposure to diisopropyl fluorophosphate (DFP), respectively, at a concentration of about 100 $\mu$M. FIG. 3C illustrates the appearance of eight scales from a jewel cichlid viewed by reflected light on a black background. Four scales on the right were exposed to DFP while the four scales on the left were unexposed.

Figure 4A:
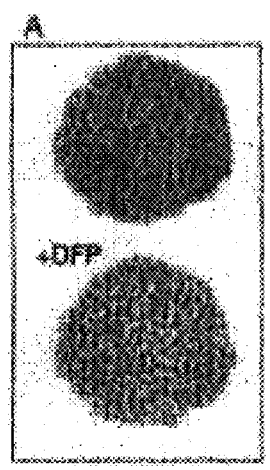
FIG. 4A shows iridophore patches of a jewel cichlid scale before and after exposure to DFP.
Figure 4B:
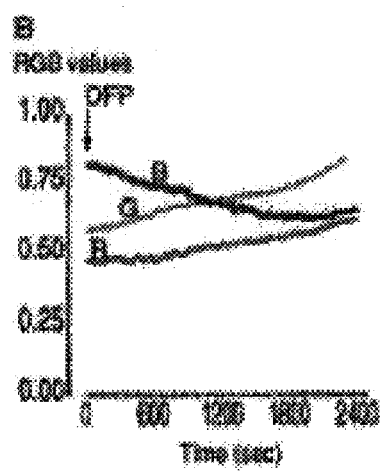
FIG. 4B is a graph of color changes of an iridophore patch as a function of time following exposure to DFP.
Figure 4C:
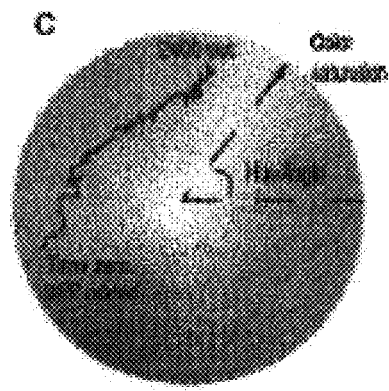
FIG. 4C is a color-space rendering of a color trajectory of the iridophore patch of FIG. 4B following DFP exposure.

FIGS. 4A–4C also illustrate changes in jewel cichlid chromatophores in response to DFP exposure. FIG. 4A shows iridophore patches of a jewel cichlid scale before and after exposure to DFP. FIG. 4B contains graphs of red (R), green (G), and blue reflectances (B) of an iridophore patch as a function of time after exposure to DFP. FIG. 4C contains a color-space rendering of a color trajectory of the iridophore patch following DFP exposure.

FIGS. 5A–5C further illustrate DFP exposure on iridophore patches. FIG. 5A contains a segmentation of colors from an iridophore patches before (top) and after (bottom) exposure to 30 µM DFP. The upper-left corners of the images show the segments that are more brilliant than a cut-off intensity (i.e., those that are the most iridescent among the population of chromatophores). The lower-right corners show the sub-segment of brilliant iridophores that were yellow in hue. FIG. 4B is a graph of brilliant yellow area as a function of time for exposure of iridophores to various concentrations of DFP.

Figure 6A:
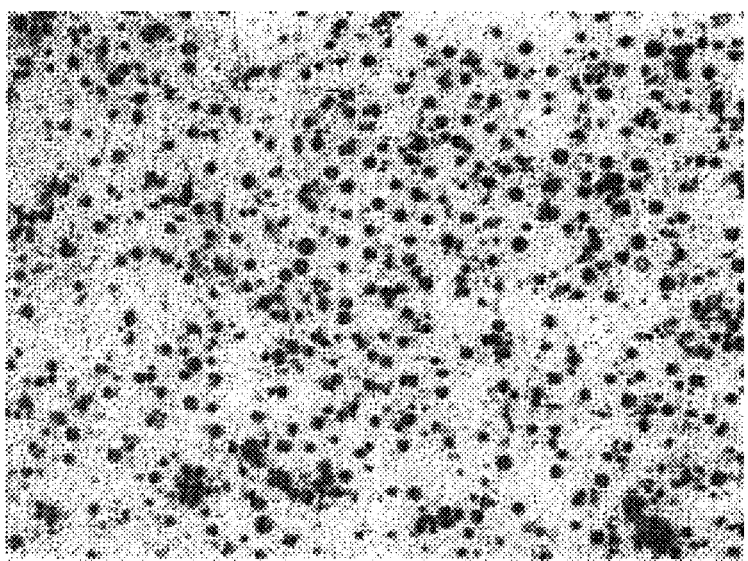
FIGS. 6A–6C illustrate pigment aggregation in Betta chromatophores after exposure to norepinephrine (NE) without pre-incubation with CTX, with pre-incubation with a threshold concentration of CTX, and with pre-incubation with a substantial concentration of CTX, respectively.
Figure 6B:
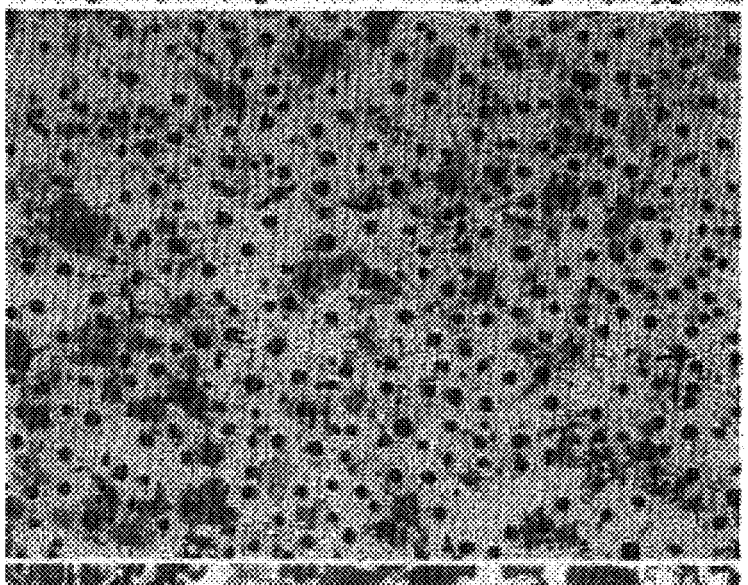
Figure 6C:
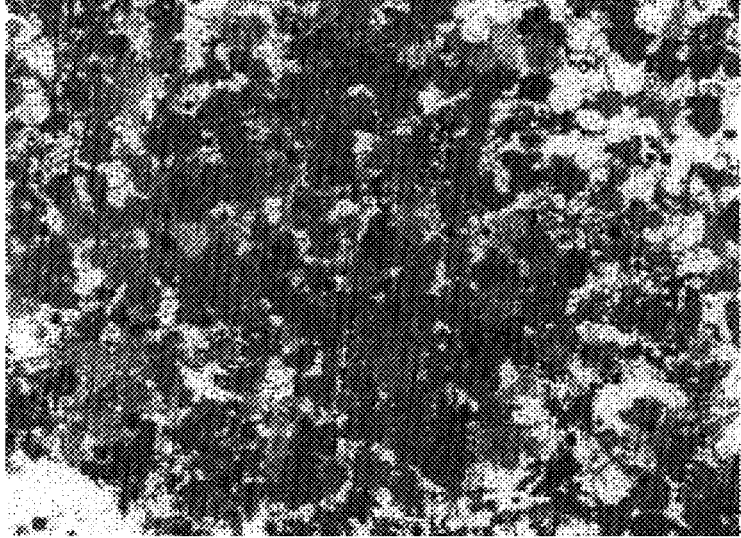

FIGS. 6A–6C illustrate pigment aggregation in Betta chromatophores after exposure to norepinephrine without pre-incubation with *cholera* toxin (CTX), with pre-incubation with a threshold concentration of CTX, and with pre-incubation with a substantial concentration of CTX, respectively. The pre-incubation period lasted a few hours, and then the chromatophores were exposed to norepinephrine (NE). As is evident, pre-incubation with CTX impaired pigment aggregation in response to NE.

Figure 12A:
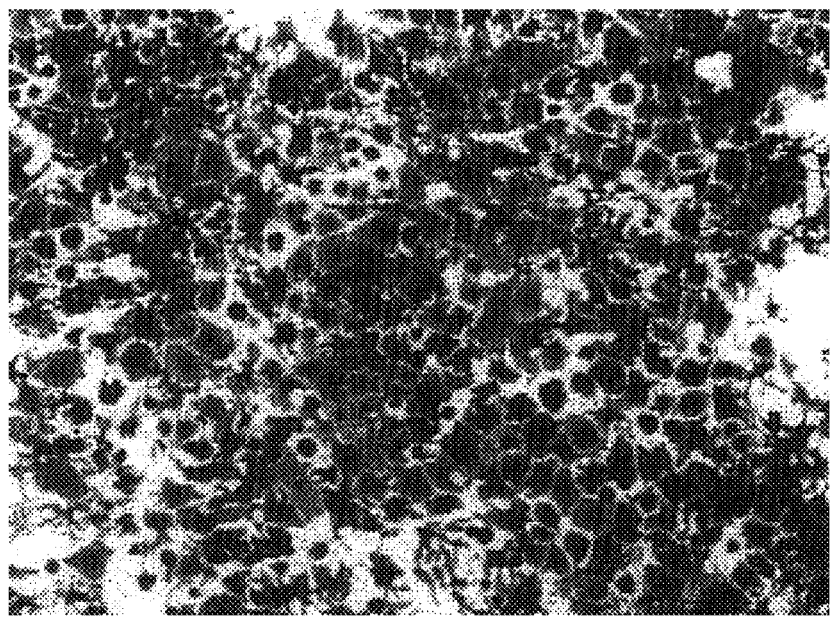
FIGS. 12A–12B illustrate the appearance of cultured chromatophores before and after, respectively, exposure to another strain of bacteria.
Figure 12B:
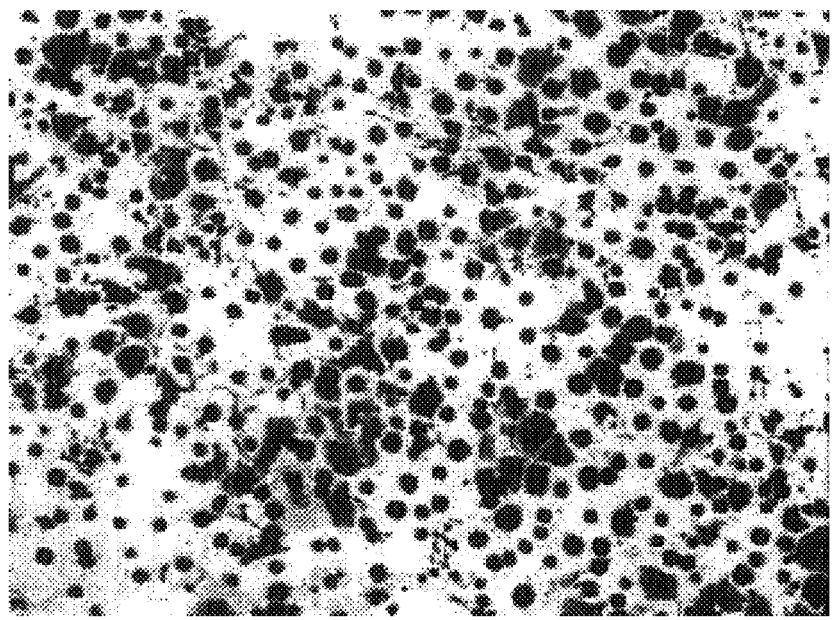
Figure 14A:
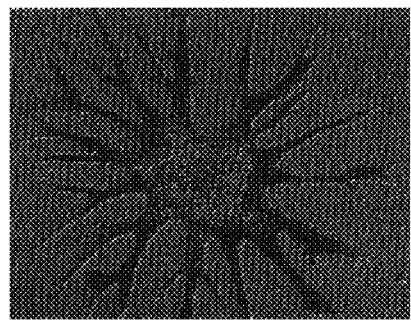
FIGS. 14A–14D are photographs of chromatophores after exposure to bioactive agents.
Figure 14B:
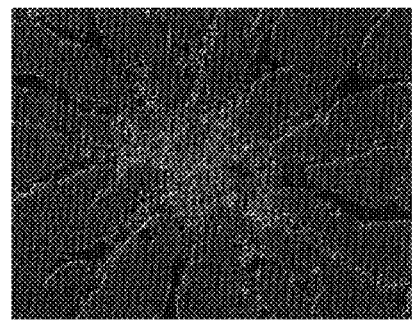
Figure 14C:
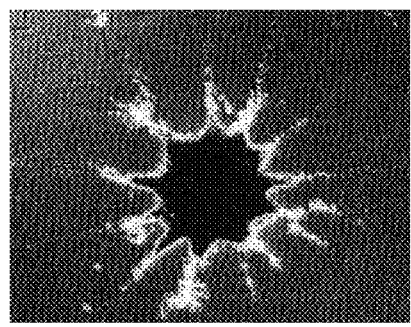
Figure 14D:
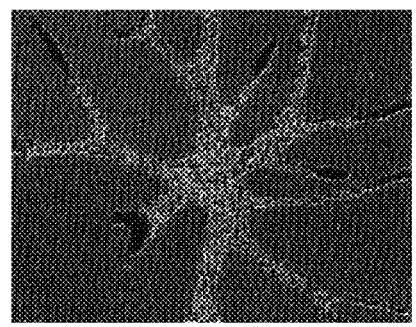

Chromatophores can be used to detect bacterial exposures. For example, FIGS. 7A–11B illustrate the appearance of *Betta splendens* chromatophores exposed to various strains of bacteria. FIGS. 12A–12B illustrate pigment aggregation produced by exposing cultured chromatophores to yet another strain of bacteria FIG. 12A illustrates the appearance prior to exposure and FIG. 12B illustrates the effects of exposure to bacteria.

Additional breadth of sensitivity to bioactive compounds can be achieved by using more than one type of chromatophore in a cytosensor. For example, FIG. 13 illustrates the effects of some bioactive agents on various types of chromatophores that are present in fish scales. The bioactive agents are divided into categories I–V and representative agents (listed in the second and third columns of FIG. 13) associated with these categories are used to exposure chromatophores at concentrations of up to a few parts per million (ppm) or parts per trillion (ppt). A fourth column lists an approximate concentration at which a chromatophore response was apparent to an observer. Effective doses noted as ppm indicate that concentrations of less than about 300 ppm were effective and those noted as ppt indicate that a response was evident at concentrations as low as about 1 ppt. The appearance of chromatophores is illustrated in the last three columns. Three types of chromatophores (black melanophores, red erythrophores, and a variably-hued iridescent patch) are included. The sizes of the melanophore and erythrophores symbols indicate whether pigment was dispersed or aggregated as a result of exposure; the color of the central iridophore patch corresponds to an overall color of the patch as a result of the exposure. The fifth column illustrates scale appearance after response to an agent listed in the first column. The sixth and seventh columns illustrate appearance of scales after exposure to an agent, followed by a challenge with norepinephrine or forskolin, respectively.

FIGS. 14A–14D are photographs of chromatophores after exposure to bioactive agents. Differences in appearance can be associated with different bioactive agents.

Figure 15A:
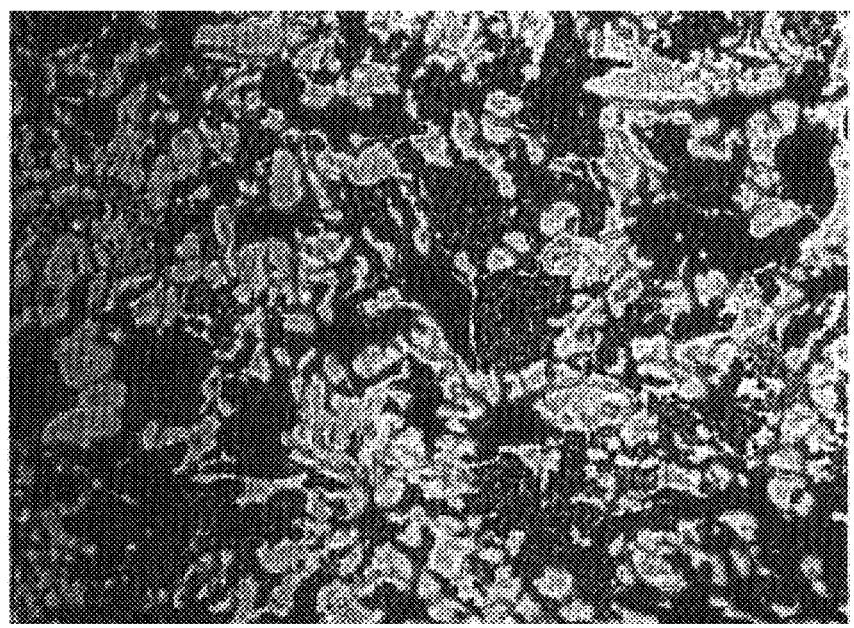
FIGS. 15A–15B are photographs of *Betta splendens* and *Hemichrorms bimaculatus* chromatophores, respectively, cultured on polystyrene using a common method.
Figure 15B:
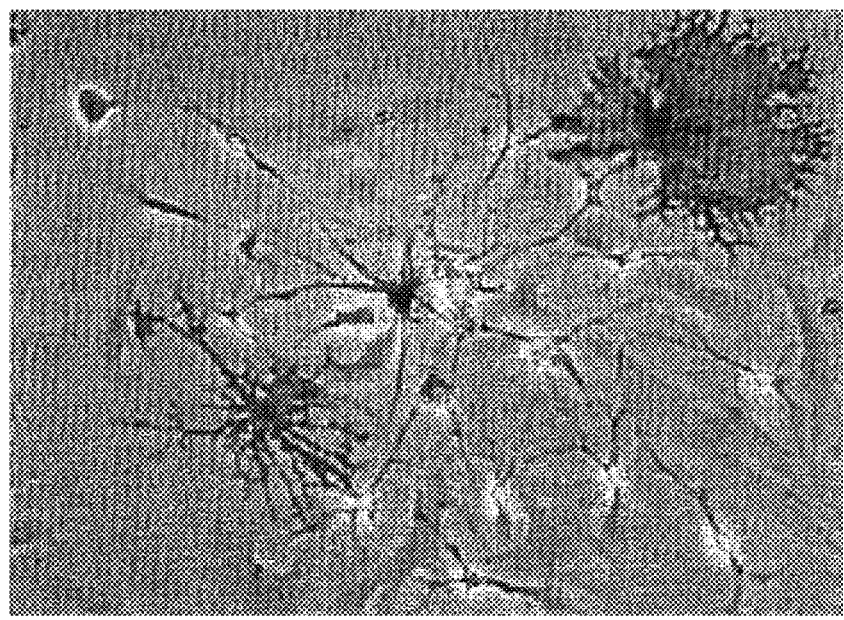

Chromatophores obtained from different species can exhibit different plating densities and morphologies. FIGS. 15A–15B are photographs of *Betta splendens* and *Hemichromis bimaculatus* chromatophores, respectively, cultured on polystyrene using a common method. The photographs were obtained at the same magnification.

Figure 16C:
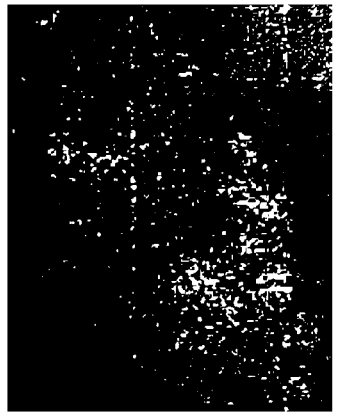
FIGS. 16A–16C are photographs of several *Betta splendens* chromatophore color variants unexposed to analytes.
Figure 16B:
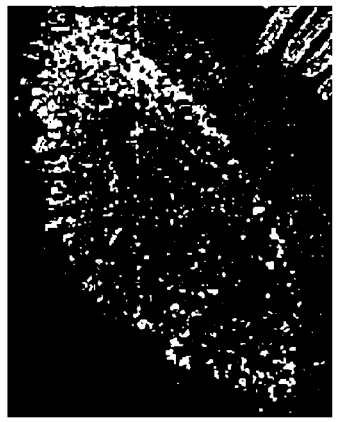
Figure 16A:
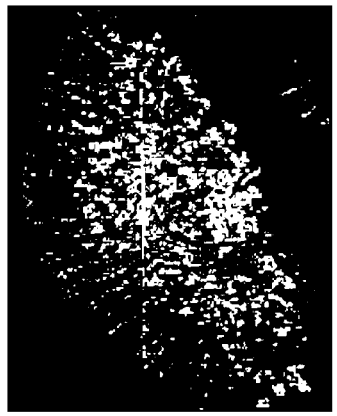
Figure 17:
FIG. 17 is a dark field photograph of chromatophores from a violet variant of *Betta splendens* without exposure to analytes.

FIGS. 16A–16C are photographs of several *Betta splendens* chromatophore color variants unexposed to an analyte. FIG. 17 is a dark field photograph of chromatophores from a violet variant of *Betta splendens* unexposed to an analyte.

As shown in the figures described above, chromatophores have morphological and color characteristics that are ideal for visual, microscopic, or instrumented analysis. As a specific example, Betta chromatophores are small in diameter in comparison with other fish chromatophores that are can be as large as 30 microns or more in effective diameter. (Effective diameter is defined as a length of a minor axis of an ellipse that circumscribes 90% of the visible plasma membrane of a chromatophore. Because chromatophores are often dendritic, cell diameter can be otherwise difficult to characterize.) In addition, Betta chromatophores tend to be uniform in size and can be densely packed to facilitate detection of color changes either visually or electronically. (See FIG. 15A.) Thus, dense, information-rich populations occupy small areas and can be interrogated with microscopic analysis and/or video recording. As a specific example, 1000 *Betta splendens* chromatophores can be situated in an area of less than 1 $mm^2$. In contrast, 1000 Nile tilapia chromatophores require an area of about 100 $mm^2$. At higher densities, Nile tilapia chromatophores were observed to not thrive. Multispectral data collection is facilitated using *Betta splendens* chromatophores because uniform populations of colors are readily prepared. FIGS. 16A–16C illustrate the appearance of *Betta splendens* scales. FIG. 17 shows cultured *Betta splendens* chromatophores.

The following example protocol was used to isolate chromatophores from a blue-green *Betta splendens* variety, a mostly black Nile tilapia, and a multicolored *Hemichromis bimaculatus*. Betta chromatophores were cultured in FSL Medium (described below) and survived in a 24-well culture dish for 30 days. The chromatophores remained filly responsive to norepinephrine (NE) during this time with cell numbers dropping by less than half at the end of 30 days. Most of this loss was attributable to the cell feeding method (the medium was suctioned away and the cells were then flooded with fresh medium). The remaining Betta chromatophores were healthy, responsive, and displayed normal morphologies. Any overgrowth of non-chromatophore cells such as epithelial cells and fibroblasts can be reduced or eliminated by differential centrifugation procedures that reduce these cell types during an initial plating of cultures.

In contrast, similarly prepared cultures of Nile tilapia melanophores were generally deteriorated at 30 days, with 90% of the cells either lost during medium changes, or remaining as non-responsive, morphologically abnormal remnants. The multispectral chromatophores of *Hemichromis bimaculatus* also exhibited substantial deterioration after less than 3 weeks in culture.

In addition, scales and fin slices from *Betta splendens* survive as active explants for at least 4 weeks, a time that is approximately as long as the longest survival time of chromatophores in explants from other tested fish species (Nile tilapia, *Hemichromis bimaculatus,* and zebrafish). Betta chromatophores can also survive exposure to broad temperature ranges. For example, Betta erythrophores were found to be tolerant of temperatures of up to 30° C. for up to 1 week. Shorter exposure periods of 2 hours at temperatures up to 35° C. did not affect viability. However, 12 hours at 35° C. caused Betta erythrophores to shown signs of deterioration. These upper temperature tolerance limits are a few degrees higher for Bettas than for chromatophores from Nile tilapia that generally cannot withstand 30° C. temperatures for sustained periods. Betta chromatophores are also relatively insensitive to changes in salinity and osmolarity. Evidence for this is described below in conjunction with experiments in which Betta splendens chromatophore response to bacteria was monitored. In these experiments it was found that the Betta chromatophores could be shifted into a FSL medium that was diluted by at least a 1:1 ratio with bacterial culture medium. Bacterial culture medium is different in both ionic composition and osmolarity from FSL. Similarly, tests of chemical agents have often entailed adding pure water as a diluent to FSL, and the ensuing decrease in ionic strength and osmolarity by at least 20% did not alter the responsiveness of the chromatophores in subsequent testing. Thus, Betta chromatophores can be effectively deployed in instrumentation and protocols that involve substantial changes in ionic strength and osmolarity.

Figure 18A:
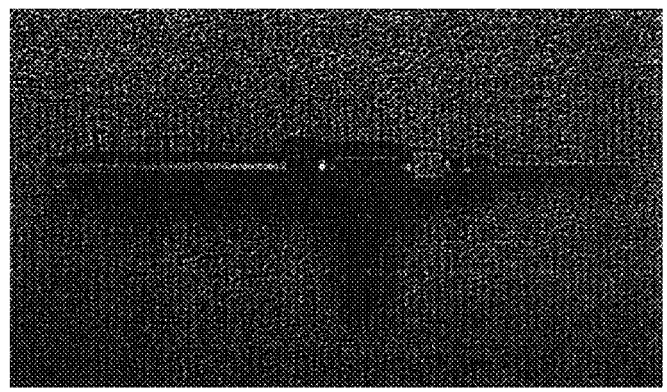
FIGS. 18A–18C are photographs of an extruder used for encapsulation.
Figure 18B:
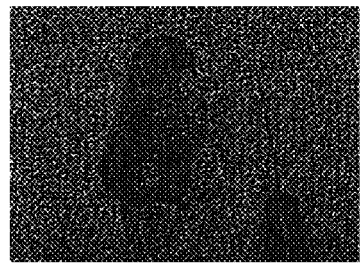
Figure 18C:
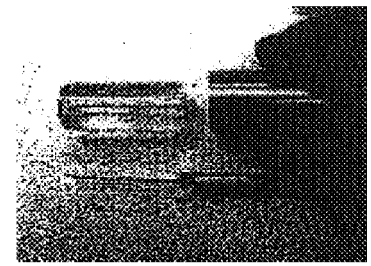

Chromatophores can be entrapped using a variety of techniques. In a particular example, a suspension of isolated chromatophores was mixed with alginate solution containing 1% to 2.5% weight percent of sodium alginate in de-ionized water. The alginate solution can contain ferromagnetic material (10% to 30% by weight) to facilitate manipulation of beads containing chromatophores within cytosensor device. The mixture was extruded into beads via an extrusion device 100 shown in FIGS. 18A–18C with a method described below in Example Embodiment 2. The diameter of the extruded beads can be adjusted to any desired diameter, typically in the range 100 $\mu$m to 2000 $\mu$m, by controlling the flow of the cell-alginate mixture and the flow of the shearing fluid. Entrapped chromatophores typically do not spread into a morphology characteristic of substrate-anchored living cells. The beads containing entrapped chromatophores can then be used in a cytosensor device.

In another method, the chromatophores can be immobilized on a substrate such as a glass or plastic substrate. Typically, a suspension of isolated chromatophores is brought into contact with glass or polymer beads that have outside diameters in a range of about 100 $\mu$m to 2000 $\mu$m. The surface of these beads can be treated with attachment factors (acid washing for glass beads for roughness enhancement, collagen and/or fibronectin) to promote cell adhesion. The beads can contain ferromagnetic material (10%–30% by weight) to facilitate bead manipulation within a cytosensor device. See, for example, Example Embodiment 12. The chromatophores typically attach weakly to the bead surface within a few minutes, and then more tightly during the next hour. During the next 24 hours the cells spread into morphologies typical of substrate-anchored living cells. The beads containing immobilized chromatophores can then be used in a cytosensor device.

Exposure of chromatophores to an analyte can be performed outside or inside a cytosensor. These methods are referred to as ex-situ and in-situ, respectively. Ex-situ mixing can be done by mixing the analyte containing at least one bioactive agent, such as chemicals, fungi, bacteria, virus, mold, protists, animal cells, or animals with an alginate solution (such as the one provided in Example Embodiment 2), with an analyte and a suspension of chromatophores. The analyte/chromatophore/alginate mixture can be extruded into beads. The extrusion is done in the device such as the one shown in FIGS. 18A–18C. Bead size can be adjusted to a size suitable for the injection of the beads into microchannels of a cytosensor device. Alternatively, the encapsulated chromatophores can be visually examined.

In some cases, the resulting beads can be encapsulated with a polymer that allows bioactive agents to pass into the bead such that the bioactive agent is maintained in physiological contact with the chromatophore. The encapsulation of the bead also functions to maintain the moisture content and nutrient content of the alginate bead such that the chromatophore is maintained in a stabilized environment. Suitable encapsulating agents include, for example, poly-L lysine, poly-D-lysine, and poly-lysines in fractional mixtures with collagen. The permeability of the membrane for chemicals of different molecular weights may be adjusted separately by adjusting the concentration of polylysine solution, molecular weight of polylysine, and reaction time between polylysine and alginate.

When used in conjunction with a cytosensor, the encapsulated beads can be loaded into a cytosensor device and manipulated as described below. Once the semi-permeable membrane (i.e., poly-L lysine) is formed, transport of fungi, bacteria, virus, mold, protists, animal cells, and/or other animals between the interior of the capsule and the exterior of capsule is prevented. The fungi, bacteria, virus, mold, protists, animal cells, and/or other animals can be encapsulated either alive or dead. The transport of chemicals across the membrane (from inside the capsule to the capsule environment, or from the capsule environment into the capsule) depends on the molecular weight of the chemical and the cut-off molecular weight of the membrane, and can be suitably selected.

In-situ methods of exposing chromatophores to analyte involve, for example, first forming alginate beads as described herein and then placing the analyte in functional contact with the beads and allowing the alginate, which surrounds the beads, to dissolve. More specifically, entrapped chromatophores in the form of the alginate beads can be loaded into the cytosensor device and placed/retained in microchannels, a cell chamber, or an observation chamber. The alginate beads are then exposed to an analyte and the bead is dissolved/disrupted. The beads can be dissolved/liquefied with the use of a suitable complexing agent for polyvalent metal ions. The analyte is thus placed in functional contact with the chromatophore, and this creates an in-situ mixture of analyte and chromatophores at a desired location within the cytosensor device.

Another representative method of in-situ presentation of encapsulated chromatophores and analyte involves performing all of the steps inside a cystosensor. Encapsulation of the chromatophores and, for example, an environmental analyte is performed inside a cytosensor device. A sample of analyte is injected into a receiving chamber of the cytosensor device that already contains admixture of liquid alginate and chromatophores. Such an admixture can be produced by inserting entrapped chromatophores as described below, followed by dissolution of the beads with a complexing agent.

In yet another example, a method of creating an admixture of liquid alginate, chromatophores and analyte involves introducing liquid alginate containing chromatophores and an analyte either sequentially or simultaneously into a mixing chamber of a cytosensor device. The mixing of the two streams occurs partially by the dissolution of one liquid stream into the other and by the shear created by relative motion of the two fluids. The admixture is then extruded through a coaxial microchannel surrounded with a microchannel annulus carrying a sheeting fluid. The sheeting fluid provides shear for the detachment of the alginate bead, and also provides polyvalent metal ions for the cross linking of alginate. This method repeats the same steps as discussed above for ex-situ mixing except that it is performed inside the cytosensor device within the microchannel structure. The entrapped analyte and chromatophores in the form of alginate beads are then pushed by the sheeting fluid flow into a washing/encapsulation chamber where the bead is captured by a capture dot as described Example Embodiment 12.

The flow of sheeting fluid is replaced with a washing fluid and subsequently with a lysine solution. The lysine solution forms the capsule around the bead just as described in the encapsulation procedure. After another washing, the complexing agent is introduced to liquefy the content of the capsule. Encapsulation is complete and the capsule is ready to be sent to an observation chamber.

This process is repeated with new analyte samples thus providing continuous formation of capsules containing analyte captured at different times and/or locations. Such methods of mixing of analyte and chromatophores are referred to as in-situ snapshot methods.

Cytosensors described herein typically detect an analyte or quantify an analyte concentration based on a morphological, color, or other change in a biological element. In a specific embodiment, a cytosensor includes a group of distinct elements that are either fluidically connected or electronically connected such that they facilitate the capture of data derived from chromatophore color. The elements can be distinct structures or can be integrated such that the entire cytosensor is contained within a single housing.

In a representative embodiment, a cytosensor is configured so that analytes are delivered in an aqueous solution or other solution. Typically, an analyte is dissolved in an aqueous medium having a chemical composition that includes osmotically balanced salts, a physiological pH, and that is free of caustic components that can corrode or otherwise degrade the cytosensor. It is generally desirable to present the analyte in a solution that is free or particulates that can clog or foul cytosensor fluid transfer components. Typically, the analyte solution is filtered using an in-line filter that admits bacteria (1 micron) but removes particles larger than about 20 microns.

Representative cytosensor fluid handling systems include a syringe configured to deliver analyte into a carrier fluid stream flowing in tubing. The carrier fluid and the analyte are directed to chromatophores that are retained in a chamber that includes an optical window or that is generally transparent. In a representative example, plastic tubing of about 0.25 mm inside diameter is configured to receive an analyte volume of about 1 microliter delivered by a glass or stainless steel syringe injected at a rate of about 0.1 microliter/sec.

Other representative examples deliver analytes using wicking or capillary flows. For example, a wick material such as cellulose fiber is configured to draw an analyte sample into a chromatophore chamber. The analyte can be applied by inserting a portion of the wick into an analyte volume or by releasing a volume of analyte onto the wick. Variable such as wick diameter, analyte volume, and flow rates can be selected for a particular application. Wick-based flows are advantageous for applications in which pumps and pump power sources are to be avoided.

In other examples, an analyte volume enters a cytosensor prior to being encapsulated. The procedure is similar to the syringe delivery of the analyte described above, except the analyte is mixed with chromatophores and a gelling agent.

Chromatophores can be provided in animal parts such as fish scales or fins, or individual chromatophores can be provided. Scales can be isolated by procedures similar to those described in Example Embodiment 1. The scale (or scales) is then mounted in a chamber, enclosed under a flow of medium, and viewed by, for example, light microscopy. Fish scales are conveniently retained by placement on a porous or fibrous material such as a nylon fabric or cellulose.

Chromatophores can be delivered into a chamber at a flow rate sufficient to allow the chromatophores time to settle onto the floor of the chamber. The floor of the chamber can be treated with attachment factors (e.g., collagen and fibronectin) to promote cell adhesion. The chromatophores typically attach weakly to the floor within a few minutes, and then more tightly during the next hour, at which time the flow-rate can be increased if needed. Over the next 24 hours the cells spread into morphologies typical of substrate-anchored living cells. At this time, the cells are ready for testing under a flow of medium.

These and other aspects of the invention are illustrated below with reference to example embodiments.

EXAMPLE EMBODIMENT 1

Betta chromatophores were generally cultured as described in this Example Embodiment. All steps in the culturing process were done using sterile technique in a tissue culture hood.

Selected fish are placed in a 4-liter anesthetic ice bath until dead, typically for at least 10 minutes, and are then washed by swirling with a large, blunt forceps in sterile water. The washed fish are then transferred into a plastic petri dish and the fins are removed using surgical scissors and fine forceps. The fins are transferred to another plastic petri dish containing phosphate buffered saline (PBS, 128 mM NaCl, 5.6 mM glucose, 2.7 mM KCl, antibiotic/antimycotic (1:100 dilution of GIBCO penicillin-streptomycin-fungizone 100×stock solution), 10 mM $Na_2HPO_4$ (pH 7.4), and 1.46 mM $KH_2PO_4$). The fin tissue is then diced with scissors into pieces of a selected size, typically 0.5–1.0 $cm^2$.

Skin is removed by placing the fin pieces in a 50 mL plastic tube containing 10 mL skinning solution (1 mM NAEDTA in PBS at a pH of 7.4). The tube is then placed in an orbital shaker at about 80–100 rpm for about 20 minutes and the skinning solution is changed about five or more times during this time. After the last skinning solution change, a filter-sterilized (0.2 $\mu$m filter) digestion solution (collagenase I (3 mg/mL)), and hyalouronidase (0.2 mg/mL) in 7 mL PBS is added. After 10–20 minutes, the digestion solution is removed using a transfer pipet and placed in a 15 mL plastic tube that is spun in a tabletop centrifuge for 2–3 minutes. The digestion solution (supernatant) is then transferred back to the 50-mL plastic tube containing the fin pieces and returned to the orbital shaker.

A pellet remaining in the bottom of the 15 mL tube contains individual cells from the fins, but the first pellet collected typically contains primarily epithelial cells and is discarded. This pelleting process is repeating at 15 minutes intervals and is repeated until substantially all of the chromatophores are collected.

Cells are recovered from the pellet by adding 7 mL of L-15 (25 mM HEPES, antibiotic/antimycotic, pH 7.4), mixing thoroughly, and re-spinning 1000 ×g for 2–3 minutes. The L-15 is then aspirated and the cells are resuspended in about 6 mL of fresh L-15. The volume of media used depends on the size of the pellet and the desired density of the cultures. Typically between 2 to 10 mL are used.

The cells are then plated in media that contains no serum because serum proteins compete with chromatophores for binding to the substrate. The substrate (typically a cell chamber surface, such as MELINEX, polycarbonate, glass, polystyrene) is coated with collagen IV (basement membrane collagen) at 0.5 to 5 µg/mL and fibronectin at 0.25 to 2.5 µg/mL and allowed to stand for a hour to allow adsorption to substrate. The substrate is then rinsed with PBS and let dry. Cells, after being plated onto substrate, are then covered and left to stand for about an hour to allow them to settle and attach After 1–2 hours in the hood the cultures now attached to the substrate and the reservoirs are filled with FSL cell culture medium (L-15, 5% fetal bovine serum, 25 mM HEPES, antibiotic/antimycotic prepared as a 1:100 addition of GIBCO penicillin-streptomycin-fungizone 100× concentrate at a pH of 7.4). The cultures can be stored at room temperature.

EXAMPLE EMBODIMENT 2A

A representative encapsulation method is described with reference to his Example Embodiment. The on-line creation of microcapsules containing both an environmental sample and chromatophores can be done with an extruder, such as shown in FIG. 18, that receives feed-streams of a gel-forming material to produce sub-millimeter sized spheres containing chromatophores and sample.

Fish cells (chromatophores) from Betta fish are isolated (as described above) from the fish tail and fins and mixed with sterile alginate solution. Polymerized alginate beads of uniform size (~400 µm) are obtained by extruding the alginate solution through the needle of an air-jet droplet generator (see FIG. 18) and collecting them in the $CaCl_2$ solution. The beads are subsequently encapsulated within a semipermeable poly-L-lysine (PLL) capsule. The interior of the microcapsules is liquefied with citric acid. This enables a liquid environment for the fish cells within a permeable capsule that will allow the diffusion of nutrients and toxins of certain molecular weight ranges.

The fish cells are pelleted by centrifugation and resuspended in 5 mL of 1.5–2.5% sodium alginate solution that has been filter sterilized using a 0.2-µm filter. The sodium alginate solution is made by dissolving alginate powder into warm saline solution (0.85 g NaCl in 100 mL distilled water). The alginate is sprinkled into the saline solution, a small amount at the time, with gentle mixing. Once it has dissolved (approximately 1–2 h), the viscous solution is allowed to cool, and then it is transferred into plastic tubes, capped, and stored in refrigerator until required.

The fish cells that were resuspended in sodium alginate solution are then extruded using either a syringe or an air-jet droplet generator into 100 mL of a 1.5% $CaCl_2$ solution. Ferromagnetic particles are added to the cell/alginate mixture prior to extrusion. The ferromagnetic particles help control motion of the microcapsules in the biosensor device using a magnetic field. See Example Embodiment 12 for description of magnetic particle manipulation.

The resulting beads are then transferred to a sterile 50-mL plastic centrifuge tube with a conical bottom. The beads are washed (10 times) with 30 mL of 0.1% 2-α-cyclohexylamino ethane sulfimic acid. A 0.1% CHES solution is prepared by adding 5 mL of CHES stock solution to 95 mL of 1.1% $CaCl_2$ solution, CHES stock solution is made by dissolving 2 g of CHES and 0.51 g of NaCl in 90 mL of distilled water, adjusting the pH to 8.2 with NaOH, and increasing the volume to 100 mL. After allowing the beads to settle (for up to 60 s), the volume of the supernatant is reduced with a vacuum aspirator.

A semipermeable capsule membrane is then formed by reacting the get droplets with 30 mL of a 0.05% (w/v) poly-L-lysine (PLL) solution (PLL hydrobromide-SIGMA (Mw=30,000–70,000) in sterile saline. The resulting capsules are then allowed to settle, the excess PLL solution is aspirated off, and then the capsules are washed with 30 mL each of 0.1% CHES and 1.1% $CaCl_2$ and with two aliquots of saline. The capsules are then resuspended in 30 mL of 0.03% sodium alginate solution for 4 min to form an outer layer on the capsules and to neutralize free active groups on the PLL membrane.

The interior of the PLL microcapsule is liquified by suspending 5 mL of the capsules in 30 mL of a 0.05 M sodium citrate solution (2.58 g of sodium citrate and 0.85 g of NaCl in 200 mL of distilled water) for 6 minutes. The capsules are then washed several times in saline to remove any excess citrate and then rocked end-to-end for 30 min to allow the alginate to diffuse out of the capsules, and for the capsules to swell toward their equilibrium state.

The capsules are now ready to be incubated with various test compounds. Incubation permits bacteria to express toxins that are detected by chromatophores.

EXAMPLE EMBODIMENT 2B

A second example embodiment included more than one population of sensor cells. One or more cell chambers were micromachined in polycarbonate. In representative examples, 2 and 5 cell chambers were defined Each of the chambers can supplied from a common reservoir. Such a design allows flexibility in fluidic connections as well as in a number and use of chromatophore chambers. Supply lines or inlet channels can be independently controlled with valves or pumps to set desired flow rates for different analytes.

Syringe pumps situated upstream of the chambers can be used to apply the sample to successive chambers. Each chamber can include individual control of sample intake volumes and flow rate using valves or with pump control. A common downstream pumping mechanism can be used to maintain a basal flow of fluid to the bank of chambers. The downstream pump can be a syringe pump, a capillary wick, a negative partial pressure, or some other pumping system. All chambers are typically configured with a basal flow of fluid that can be achieved by either individual pumps or a common downstream pump. Such a pump can be a syringe pump, a wicking type pump mechanism, an electro-osmotic type, or some other pump. A multi-stream arrangement can be used to direct parallel and separate streams through a common chamber to achieve concurrent sampling in a common cell chamber. Multiple streams within a single chamber may be possible and thereby permit introduction of multiple analytes into a common chamber. By setting the proper flow conditions these streams can remain separate within the chamber. A simple two-stream prototype was used to evaluate the extent of fluid mixing by adjacent streams within a single chamber and showed that fluid mixing control is achievable.

An illumination system includes a light source such as a laser diode, light emitting diode, or lamp that emits radiation that is directed to the sensor cells. An optical system can be provided to shape and direct the radiation, and mirrors or beamsplitters can be configured so that a single light source illuminates more than one cell chamber. One or more cameras are arranged to receive radiation from the cell chambers. A single camera can be arranged to image cells in one or more cell chambers using relay optics, or several cameras can be used. Multitasking can be used to enable one or more computer systems to process the images collected from multiple chambers.

An encapsulation machine can be used to take periodic samples of analytes and package them for optical measurements, using a method of continuous encapsulation of sensor cells. After formation, capsules can be arranged in an order that allows each to be associated with the period of time that a respective sample was fed into the system. Controlled microfluidics and/or movements achieved by the use of magnetic fields on suitably doped capsules can be used to move the capsules to positions within an instrument where they can be optically observed. An optical detection system can be used to measure optical appearance of the chromatophores within the capsules.

Various types of illumination can be used to irradiate the capsules, including a fluorescent lighting arrangement based on innate fluorescence of some chromatophores (including erythrophores), or fluorescence of a marker introduced into the chromatophores.

An analyzer with parallel processing capabilities or other suitable hardware architecture can be used to keep track of the optical appearance of the capsules and determine whether a significant change occurs in any capsule. Given that each capsule is associated with a particular sample entry time, results can be associated with analyzer times at which biologically active agents are introduced.

A sensor cell feed line provides chromatophores in a form that makes them readily available for encapsulation and an analyte feed line receives a liquid sample that is directed to an encapsulation zone. The encapsulation zone is a portion of a cytosensor at which sensor cells and analyte are mixed together and, in conjunction with gel-forming and gel-dissolving components, capsules are formed.

EXAMPLE EMBODIMENT 3

Detection of algal extracts with chromatophores is described in this Example Embodiment. A correlation between cytosensor activity and pharmacological activity of algal extracts was established using a cytosensor assay. The degree of aggregation and dispersion in chromatophore cells, specifically melanophores, is determined using a melanophore index rating system. The melanophores are placed in contact with an algal extract for twenty-four hours and then tested by exposure with norepinephrine. Norepinephrine is known to cause complete melanophore aggregation. Four basic types of responses were observed as the result of cytosensor exposure to algal extracts.

In a type I response, the extract has no effect on the cytosensor. In a type II response, a direct change in the melanophore index is produced as the result of extract exposure followed by complete aggregation due to norepinephrine exposure. In a type III response there is a direct response to extract exposure followed by impaired aggregation when exposed to norepinephrine. In a type IV response there is no direct response to algal extract exposure and there is impaired aggregation from subsequent norepinephrine exposure. Extracts were tested along with fractions from extract 1233, and three pure marine toxins: brevetoxin A, saxitoxin, and curacin A. The activity of melanophore aggregation or loss of ability to aggregate suggests that there is a correlation between algal extract activity and cytosensor activity. This correlation indicates that such a cytosensor is useful in screening active algal extracts for pharmaceutical activity.

Algal extracts were detected using melanophore activity from Nile tilapia scales. A solution of 2.3 mM tricaine methanesulfonate (MS222) and 20 mM Tris-HCl (pH 7.6) in deionized water is used to euthanize the Nile tilapia fish. (Plunging the animal in a cold ice bath can also be used to kill the fish.) The tilapia is removed from the solution and placed in a plucking apparatus. The plucking apparatus consists of a pipette box lid containing a fish tank water filter cut in half. The water filter is pre-moistened with deionized water or PSS (see below). Residual MS222 is removed from the fish by rinsing both sides of the fish. Typically, 60 scales are removed from the dorsal fin area of the tilapia. The scales are placed into 100 mm petri dishes containing 20 mL of a divalent cation-free "skinning solution" (1 mM EDTA and 10 mM glucose in phosphate-buffered saline, pH 7.4). The skinning process consists of four 30-minute intervals at 70 rpm on the shaker. The time and degree of shaking can be selected according to the efficiency at which the skinning process removes epithelial cell from the surface skin layers of the scale. For *Betta splendens* scales, a shorter incubation time and gentler agitation can generally be used. After each 30-minute interval, the spent skinning solution is replaced with 20 mL of fresh skinning solution. The final exchange replaces skinning solution with 20 mL of physiological saline solution (PSS) (128 mM NaCl, 2.7 mM KCl, 1.8 mM $CaCl_2$, 1.8 mM $MgCl_2$, 5.6 mM glucose, 10 mM Tris-HCl 7.2 pH, 100 U/mL penicillin, and 100 $\mu$g/mL streptomycin). Following the skinning process, the scales are stored at 25° C. for 24 hours during which time they undergo a period of spontaneous optical changes. These spontaneous changes are related to the tissue injury caused by their excision, which causes internal bioactive agents (neurotransmitters and hormones) to temporarily induce optical changes. Scales can be stored for periods of weeks in PSS. A change of the PSS solution each week to serve as a periodic feeding was used, but other feeding regimens that maintain the sensitivity of the chromatophores can be used.

EXAMPLE EMBODIMENT 4

In this embodiment, testing for bacteria is described. Defined bacterial strains can be obtained from research labs or from culture collections such as the American Type Tissue Culture. A pure culture of bacteria (one that consists of only one type of bacteria) is cultivated in a culture-specific medium using aseptic technique. This medium can be Luria broth's (LB) or any other conventional, nonconventional, chemically defined (synthetic) or undefined (complex) medium as described in references such as that published by ATCC (American Type Tissue culture). In addition to appropriate nutrients, cultivating bacteria requires suitable environmental conditions, including temperature, pH, and oxygen conditions. When necessary, these environmental conditions are adjusted to obtain optimal growth of bacterial cultures.

Bacterial strains can be obtained from natural habitats. Aseptic technique is used to obtain a pure culture of bacteria from its natural habitat These pure culture isolates are then cultivated as described above.

If desired, the bacterial culture can be filtered or centrifuged to separate bacterial cells from the medium, each of which can then be assayed in FSS (fish saline) or FSL (fish complete medium). Alternatively, the whole suspension bacteria plus medium) can be diluted into FSS or FSL and used directly in the toxicity assay.

Gram negative and Gram positive bacterial strains have been tested against *Betta splendens* chromatophores. The experimental approach was similar for all bacterial strains tested. Pure cultured bacterial strains were cultivated and approximately $10^7$ bacterial cells were added to FSS (fish saline) or FSL (fish complete medium) containing biosensor cells, and the reaction of the biosensor cells to the bacterial cells was noted microscopically after 5, 10, 15, 30 and 60 minutes. A direct positive reaction was observed when the pigment of the biosensor cells rapidly aggregated (in the first 5 minutes after the addition of the bacterial cells to the biosensor cells) in a manner similar to that observed with norepinephrine (NE). The Gram negative bacterial strain JM101, a non-toxin producing *Escherichia coli* strain used commonly in molecular genetic manipulations, did not cause the pigment of the biosensor cells to aggregate, thus indicating a negative response. This *E. coli* strain can be used as a negative control in toxicity assays. The Gram positive bacterial strain ATCC #6051, a non toxin producing *Bacillus subtilis* strain used commonly in molecular genetic manipulations, does not cause the pigment of the biosensor cells to aggregate, thus indicating a negative response. This *B. subtilis* strain can be used as a negative control in toxicity assays. Similarly, the Gram positive non-toxin producing *Lactococcus lactis* bacteria used commonly in food fermentations processes does not cause the pigment of the biosensor cells to aggregate, thus indicating a negative response. This Lactococcal strain can also be used as a negative control in toxicity assays. In contrast, the Gram negative bacterial strain ATCC#4931, a toxin-producing *Salmonella enteritidis* strain, caused the pigment of the biosensor cells to aggregate within the first 5 minutes indicating a direct and rapid response of the biosensor cells to the toxin-producing *Salmonella enteritidis*. Similarly, the Gram positive bacterial strain ATCC#49064, a toxin producing *Baillus cereus* strain, causes the pigment of the biosensor cells to aggregate within the first 5 minutes indicating a direct and rapid response of the biosensor cells to the toxin producing *Baillus cereus*. Both the *Salmonella enteritidis* (ATCC#4931) and the *Baillus cereus* (ATCC#49064) strains were isolated as a result of a human gastroenteritis outbreak. Similar aggregation responses were elicited by a toxin-producing *Escherichia coli* O157:H7 strain and a *Vibrio cholera* strain.

In addition to the defined bacterial strains obtained from research labs or from culture collections such as the American Type Tissue Culture, bacterial strains obtained from natural habitats were also assayed. Of the seven pure bacterial isolates obtained from natural habitats and tested to date, three caused pigment of the biosensor cells to rapidly aggregate (within 5 minutes) indicating the presence of a toxin. The three naturally occurring bacterial isolates have been putatively identified as a Bacillus sp., a *Baillus cereus*, and a Clostridium sp. The other four bacterial isolates that did not cause the biosensor cells to rapidly aggregate (thus indicating no presence of toxin) were identified as either a Pseudomonas sp. or a *Bacillus subtilis*.

EXAMPLE EMBODIMENT 5

Biological toxins in food and water can also be detected using a cytosensor. Three classes of purified toxins were tested, including an enterotoxin, a membrane damaging toxin, and a protein synthesis inhibitor. Purified *cholera* toxin, an enterotoxin from *Vibrio cholera*, causes hyperdispersion at toxin concentrations of 50 ng/mL down to 1 ng/mL, following a 20 hour incubation of *Betta splendens* chromatophores with purified toxin. The levels of cAMP are increased with the addition of *cholera* toxin, and presumably this impact correlates with the observed hyperdispersion. The inhibition of norepinephrine (NE) induced pigment aggregation in *Betta splendens* chromatophores by *cholera* toxin is detected at concentrations as low as 1 ng/m after a 20 hour reaction time. The NE inhibition affect by *cholera* toxin is more evident at higher *cholera* toxin concentrations.

A membrane damaging toxin, alpha-hemolysin from *Staphylococcus aureus,* directly changes *Betta splendens* chromatophores in a manner similar to NE. Pigment aggregation in these chromatophores can be observed one hour after the addition of 0.5 or 0.1 µg/mL of alpha hemolysin toxin. A protein synthesis inhibitor, Shiga-like toxin, had no readily observable effect on the *Betta splendens* chromatophores at the highest dose tested (0.1 mg/mL).

EXAMPLE EMBODIMENT 6

A cellular biosensor that couples the analytical sensitivity of fish chromatophores to the neurotransmitter secretory behavior of nerve cells can be implemented. Such a system can be applied to detection of the neurological toxins botulinum and tetanus in unknown samples and can used with combinations of several types of chromatophores.

A multi-cell system uses culture procedures that allow chromatophores and PC12 nerve cells to coexist in similar environments of temperature and media composition for an extended period. The system also allows the neuron-chromatophore bioassay to detect the effects of neurotoxins on PC12 cells. This method has been developed to monitor the activity of nerve cell neurotransmitter secretion using changes in chromatophore morphology. The substances examined with this assay include toxins whose pathogenesis is mediated through inhibition of the neurosecretory pathway. In this Example Embodiment, the Clostridial toxins botulinum and tetanus are selected. In addition, the responses caused by each toxin are characterizable, allowing differentiation of toxins in an unknown sample. For example, toxins including *cholera, pertussis*, and β-latrotoxin can be measured or detected using a neuron-chromatophore bioassay.

EXAMPLE EMBODIMENT 7

In this example, a population of 1000 Betta chromatophores contained in a cell chamber was used to detect a known bioactive agent, norepinephrine. The sample of norepinephrine was introduced into the cell chamber via syringe injection. Video images of the optical appearance of the chromatophores were analyzed. A statistically significant change in the appearance of the chromatophores was recognized by an analysis algorithm built into the cytosensor. Thus, at the expected moment when norepinephrine entered the cell chamber, the ensuing optical changes in the chromatophore sensor cells were sensitively reported by the cytosensor instrumentation.

Male fish of a red variety of *Betta splendens* were used as source of chromatophores that were obtained using the protocol described above. The chromatophores were transferred to a cell chamber and included approximately 1000 chromatophores (90% erythrophores, 9% melanophores, 1% iridophores) that occupied a 1 $mm^2$ viewing area. See FIGS. 1A–1B for examples of Betta chromatophore appearance.

A cell chamber was constructed using a laminate construction method as described herein. The geometry of the cell chamber is describe in Example Embodiment 10. An outer layer was a transparent material (Melinex 453) for viewing the sensor cells. In this embodiment, the chromatophores were attached to the interior-facing surface of a transparent window layer. A chamber interior was routed with fluidic lines so that entry and exit of fluids and analytes could be accomplished. The fluidics geometry was designed such that the shear tolerance of cells fell below the expected allowable value of 1 $N/m^2$ at a height of 350 microns with a flow rate of 10 microliters per minute in a one millimeter wide section.

The cell chamber was sandwiched between the two halves of a fluid interconnect (see Example Embodiment 10). The interconnect supplied the tubing to the fluid delivery system and the sample injection system. A connector was used that had an inlet tube at right angles to the chamber flow direction. The end of the tube was flanged, with the flanged portion held tight against the inlet port walls so that fluid could escape through the tube into the chamber. The dimensions and hexagonal geometry of the fluid interconnect were chosen so that the light source and camera mechanism could be mounted for recording the optical signals from the sensor cells.

A syringe injection system and syringe pumping system was used to deliver sample and aqueous medium to the cell chamber. A commercially available syringe pump (Hamilton, Reno Nev.) was used to deliver fluids into the chamber. Various flow rate could be selected. The syringe pump and injection system are described in additional detail elsewhere herein.

The optics subsystem imaged a central 1 mm×1 mm area of the 3 mm×3 mm total sample area onto the color CCD array for optimal field of view. A Hastings triplet lens provided an achromatic, flat field of view. The cell chamber was illuminated with white light emitting diodes.

An example analyte sample (two microliters of 100 nM norepinephrine dissolved in FSL medium) was delivered as a uniform front (slug) into the chamber.

A detection and identification algorithm used a time sequence of images acquired every five seconds. Analysis included the steps described in the flowchart referred to in Example Embodiment 10 and the steps were implemented on a general-purpose microprocessor running Windows NT. Screen capture shown in Example Embodiment 10 shows detection results using 92 images. An alarm was triggered at a 60th frame, with a delay of two frames. Signature identification used 10 frames (from 58th to 67th). Frames 1 to 57 correspond to slowly changing statistics (null hypothesis). Frames 68 to 92 represent statistical equilibrium. Control injections of a blank analyte (FSL medium with no added norepinephrine) caused no alarm. Thus, upon injection of 100 nM norepinephrine, the analyzer indicated >0.99 probability of a biologically active agent. The response time of the cytosensor was typical of the biological response time to norepinephrine (i.e., less than about 1 minute).

EXAMPLE EMBODIMENT 8

Multispectral optical changes of chromatophores offer a great deal of information that can be used to evaluate exposure to biologically active agents. Automated cytosensors can be built to utilize this full set of color information. In Example Embodiment 8, multiple colors are used to detect or quantify analytes or classes of analytes. The skin and scales of some brightly colored fish generally include patches of iridophores that reflect specific wavelengths of light as well as pigmented chromatophores that absorb various wavelengths of light. As a result, various colors can be produced as regulated by the nervous and endocrine systems of the animal. In this example, such multispectral features are used in a cytosensor for detection of many kinds of biologically active agents.

Scales of the West African *Hemichromis bimaculatus* include several color classes of chromatophores that are responsive to numerous bioactive agents. For example, the agent DFP (at a concentration of about 0.5 mM or approximately 100 ppm) triggers optical changes in several color classes. As observed, DFP exposure triggers the reflected coloration of the iridophore patch to change within about 1 minute from predominantly blue to predominately green in appearance. Other chromatophores (e.g., melanophores, erythrophores, xanthophores) change with respect to an area occupied by cell pigment. Other biologically active substances (including norepinephrine, forskolin, and *cholera toxin*) also change the appearance of the *Hemichromis bimaculatus* chromatophores.

About 500 light reflecting centers are responsible for the light reflectance from a typical patch of iridophores, enabling the color changes in the iridophore patches to be easily visible, and suggesting that iridophores can be readily adapted for use in cytosensors. Reflection from an iridophore is produced by a subcellular organelle referred to as an iridosome. When viewed with an electron microscope, iridosomes include stacks of microcrystalline platelets separated by distances of between about ½ to ¼ of the wavelength of visible light. Such microcrystals are typically composed of guanine and other purines. Analyte-induced changes in platelet separations produce shifts in maximum reflectance wavelengths.

Because chromatophores include complex signaling pathways, chromatophores are sensitive to many agents. The class of organophosphate enzyme inhibitors can serve as an example that illustrates how chemical enzyme inhibitors change the appearance of multispectral populations of chromatophores. Organophosphate inhibitors (including biochemistry reagents such as DFP as well as notorious chemical warfare agents such as sarin) generally act via an irreversible reaction with active site amino acid residues of hydrolases.

Exposure of *Hemichromis bimaculatus* scales to aqueous solutions of DFP produced a pronounced color change from blue to green. This change was quantified with video microscopy and digital image analysis. The color changes and analysis are illustrated in FIGS. 4A–4C. FIG. 4A shows an example in which an iridophore patch of a scale is viewed by a mixture of transmitted and reflected light at low magnification. FIG. 4B shows quantitative changes in red, green, and blue response of the patch as a function of time after exposure to DFP. FIG. 4C represents patch color change in a hue-saturation-value (HSV) color space, showing that the color dimension hue angle (H) changed markedly from blue to yellow after DFP exposure, while color saturation (S) and the color-intensity (I, not shown) did not change significantly. Thus, cytosensor measurements can be based on hue determinations.

Using HSV as an indicator of exposure to DFP (the yellow-hued channel), cytosensor sensitivity can be increased. Digital color segmentation was used isolate the colors of the brilliantly reflective iridophores and to isolate the yellow-hued reflections. The yellow-hue increased with increasing doses of DFP. The threshold dose for triggering a detectable response was about 10 $\mu$M DFP.

In addition to hue changes in iridophores, other colored cell types also exhibited color changes with DFP, exposure such as melanophore and erythrophore pigment aggregation, and xanthophore pigment dispersion (not shown). Within 10 minutes of exposure to DFP, a series of changes were underway that were measurable in multiple spectral channels. Simplified illustrations such as those of FIG. 13 illustrate how multispectral chromatophores of *Hemichromis bimaculatus* scales are affected by DFP, other organophosphates, and several other cholinesterase inhibitors. The different agents induced differing responses in the multispectral set of chromatophores. A further improvement in differential capability was gained by employing a "failure mode" analysis, which determined how a given biological agent interfered with subsequent optical changes when challenged by a well-characterized agent (norepinephrine and forskolin are two examples of challenges shown here, other agents can be used).

The mechanism for organophosphate induced optical changes in multispectral populations of chromatophores is not completely understood. One target of organophosphates is acetylcholinesterase but acetylcholinesterase is not typically involved in the anatomical locale of chromatophores (subdermal skin regions), and so organophosphates are unlikely to affect jewel cicichlid chromatophores via the inhibition of acetylcholinesterase. Indeed, acetylcholine itself caused no color change. Thus, one or more among the many other serine hydrolases of cells could be the enzymatic targets whose inactivation leads to optical changes in chromatophores.

Many other agents and classes of toxic agents can be detected by the multispectral responses of chromatophores. For example, Hemichromis bimaculatus chromatophores changed in response to exposure to cholera toxin (1 nM, 2 hour exposure, purified cholera toxin from Sigma Chemical Co.). After this exposure, the melanophores were unimpaired upon challenge by norepinephrine (i.e., the black pigment aggregated as normal towards the center of the melanophores). However, erythrophore response was impaired as norepinephrine exposure did not produce the typical aggregation of red pigment.

These categories include toxic organophosphates, toxic pollutants (heavy metals, polyaromatic hydrocarbons, and various categories of pharmacological drugs). In addition, the entirely unique discovery has been made showing that chromatophores are methodologically effective in testing the bioactivity of compounds whose composition is entirely unknown at the time they were presented to chromatophores. Such compounds include compounds in extracts from algae (under study because of their potential content of interesting lead compounds for drug discovery) and compounds produced by microbial cells (under investigation as toxic pathogens from water sites, from food contamination, and from environmental contamination). Furthermore, the purity and concentration of the compound(s) under investigation can be unknown at the time of their exposure to a chromatophore-based biosensor as many different biologically active substances are detectable in various purities and concentrations using chromatophores.

EXAMPLE EMBODIMENT 9

Chromatophores can be used to detect bioactive compounds that act upon specified molecular targets. For example, one important class of compounds includes pharmacological agents that act upon the membrane channels that admit calcium ions into cells. Drugs based on the activation or inhibition of these membrane channels can be useful in treatments of various diseases and syndromes. To provide such chromatophore-based sensors, sensor cells are evaluated for the presence of a calcium ion channel. As a specific example, calcium-dependence of pigment transport in melanophores and erythrophores was evaluated.

The signal transduction pathway initiated by the formation of cAMP by adenylate cyclase has been relatively well characterized in its role on intracellular motility in erythrophores and melanophores. This enzyme is closely connected to the $\alpha_2$-adrenergic receptor, the stimulation of which leads to the direct modulation of intracellular levels of cAMP. These levels have been directly implicated in both the aggregation and dispersion of pigmented vesicles within the cytoplasm. Decreased intracellular levels of cAMP have been shown to induce rapid aggregation of vesicles while increases in cAMP levels lead to dispersion. An alternate signal transduction pathway that has been implicated in vesicle motility in erythrophores involves the role of calcium concentration in the cytoplasm. The role of calcium in erythrophores is relatively misunderstood compared to the role of cAMP. Conflicting results have been obtained concerning whether calcium has a direct impact on intracellular motility in erythrophores. Example Embodiment 9 includes direct pharmacological evidence for the presence of calcium ion channels on the plasma membrane of erythrophores but not melanophores. The activity of these channels leading to altered intracellular calcium concentrations results in the translocation of red pigmented vesicles in erythrophores, but no corresponding changes in the black pigment of melanophores.

Erythrophore cultures were prepared 3–10 days prior use as described below. Dorsal, caudal, and anal fins were clipped from euthanized male Betta splendens and diced into 2.0–4.0 mm squares. The diced fins were washed in six solution changes of phosphate buffered saline (PBS) (137 mM NaCl, 2.7 mM KCl, 10 mM $Na_2HPO_4$, 1.6 mM $KH_2PO_4$, pH 7.4) containing mM NAEDTA, and transferred into 7 ml of digestion solution (PBS containing 960 unit/ml collagenase I and 230 unit/ml hyalouronidase Worthington Biochemical Corp., Lakewood, N.J., USA). After a 30-minute incubation, dissociated erythrophores were separated from the digestion solution by centrifugation for 3 minutes at 300 ×g and resuspended in L15 media (Sigma-Aldrich Co., St. Louis, Mo., USA) supplemented with 5% fetal bovine serum. Erythrophores from three successive digestion solution incubations were pooled and suspended in complete L15 media at a concentration of $1 \times 10^5$ cells/ml. Cells were plated on 15 mm diameter glass cover slips coated with 20 $\mu g/cm^2$ collagen IV and 15 $\mu g/cm^2$ fibronectin (both from Sigma-Aldrich Co.) by placing one drop on each cover slip. After allowing the erythrophores to attach to the substrate for one hour, the cover slips were submerged in complete L15 media and stored at room temperature. Mixed cultures containing both melanophores and erythrophores were prepared by choosing fin tissue that contained both color types of chromatophores. Alternatively, different fish can be used to provide different types of chromatophores and a suitable combination produced by mixing.

Prior to exposure with calcium-modulating chemicals, erythrophores attached to cover slips were loaded into a continuous flow chamber (Warner Instrument Corp., Hamden, Conn., USA) and equilibrated for 5 minutes in physiological saline solution (PSS, 128 mM NaCl, 2.7 mM KCl, 1.8 mM $CaCl_2$, 1.8 mM $MgCl_2$, 5.6 mM glucose, 10 mM Tris/HCl, pH 7.2). Added agents were injected directly into the enclosed cell chamber at the given concentration dissolved in 200 $\mu l$ of PSS. Added chemicals can be flushed out of the cell chamber by continuous upstream flow of PSS.

An assembled erythrophore chamber was mounted on a stage of a Zeiss IM-35 inverted microscope (Oberkochen, Germany) fitted with a Plan 6.3x objective having a 0.16 numerical aperture. A field of view was chosen that included about 200 erythrophores. Digital images were captured every 20 seconds with a Panasonic GP-US502 color 3-CCD camera using a Flashpoint 3D frame grabber and a personal computer based on a Pentium III processor. Image processing was performed using Image Pro 4.1 image analysis software.

Measurements were based on the following steps. Images were segmented to distinguish erythrophores (dark objects) from a bright background and a relative area occupied by erythrophores was calculated. The area was then calculated for all dark objects in the segmented image. The area was calculated in relative size units.

Pigment aggregation and dispersion trends within a sequence of images were determined by calculating a relative aggregation for each image in the sequence. The relative aggregation (Relative Aggr.) was computed using the following formula:

$$\text{Relative Aggr.} = -\log_{10}(\text{Pixel Area/Reference Pixel Area})$$

wherein the pixel area was determined for each image and the reference pixel area was the area for the first image in the sequence.

A dose-response curve was obtained and individual data points in the dose response curves were found by calculating a dispersion ratio for each test. This value was calculated as the following ratio: dispersion ratio=(erythrophore area after 10 mm exposure)/(erythrophore area before exposure).

The requirement of calcium for intracellular transport in erythrophores has been hypothesized for erythrophores previously, but the involvement of the key molecular target of membrane acting calcium channel blocking drugs has not been investigated. The calcium requirement for intracellular transport of pigment was confirmed in *Betta splendens* erythrophores by treating the cells with a common aggregation-inducing stimulus (10 nM norepinephrine) in solution that either contained calcium ion or solution devoid of calcium ion. The results on erythrophores from this treatment are shown in FIGS. 19A–19B and 20A–20B. With reference to FIG. 19B, in calcium containing PSS (1.8 mM added $Ca^{2+}$), treatment of erythrophores with norepinephrine produces apparent aggregation of pigment-containing vesicles with respect to unexposed erythrophores (FIG. 19A). With reference to FIG. 20B, exposure in PSS with 1 mM EGTA and no added calcium produces no apparent aggregation in comparison with unexposed erythrophores (FIG. 20A). It is evident that pigment aggregation was impaired by the lack of calcium. Thus, pigment transport can be altered by pharmacologically perturbing intracellular calcium concentration.

Modulators of plasma membrane calcium channels were initially considered as a means of controlling intracellular calcium levels. The direct application of the calcium channel activator Bay K8644 resulted in neither the aggregation nor dispersion of erythrophore pigment and direct application of a variety of $Ca^{2+}$ channel inhibitors did not produce a direct response in erythrophores. However, pre-treatment with norepinephrine has a two-fold effect on erythrophores. First, NE operates through adrenergic receptors to open receptor-activated calcium channels on erythrophores. This results in a higher transient intracellular $Ca^{2+}$ concentration. Second, NE acts as an agonist of $\alpha_2$-adrenergic receptors that leads to inhibition of adenylate cyclase and a decrease in intracellular cAMP levels, a pathway that is well characterized in association with the aggregation of pigment in all dendritic chromatophores, including erythrophores. The application of inhibitors of plasma membrane calcium channels to erythrophores after pre-treatment with norepinephrine resulted in immediate and rapid dispersion of pigmented vesicles.

Figure 21:
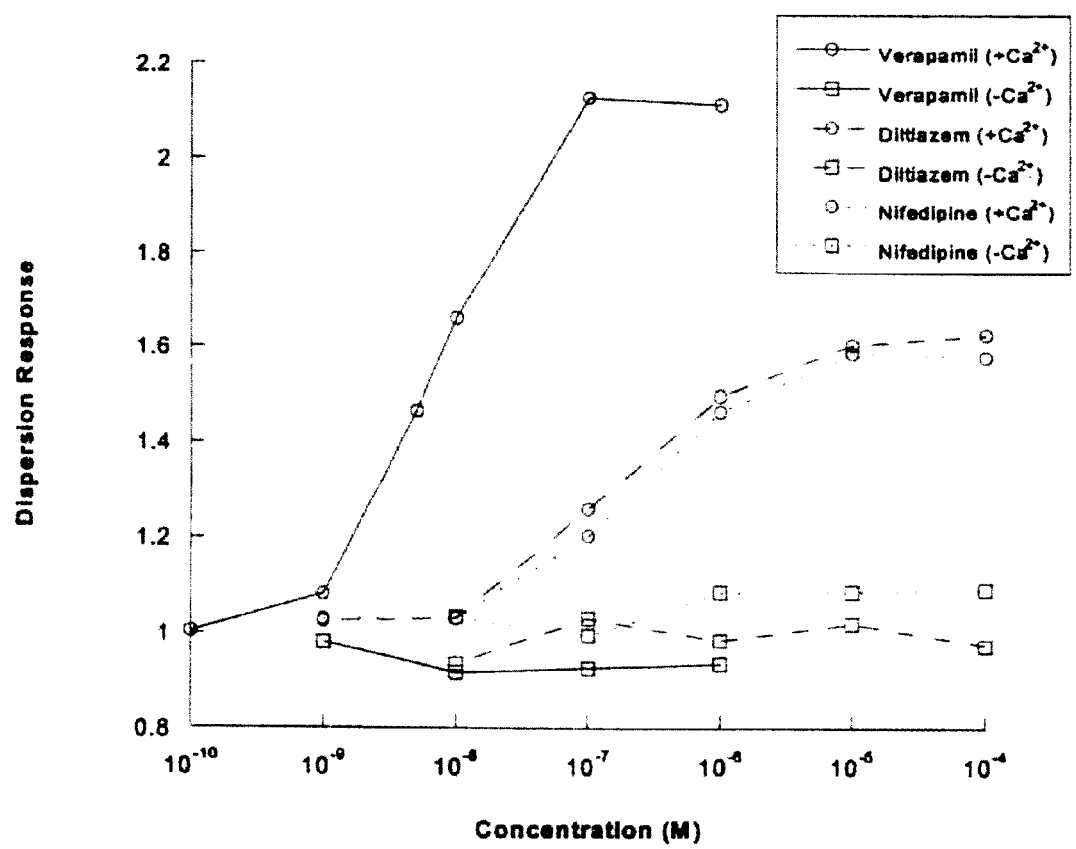
FIG. 21 contains dose-response curves for erythrophores exposed to channel blockers verapmil, nifedipine, and deltiazem, with and without added calcium ions.

FIG. 21 contains dose response curves for inhibitors verapamil, diltiazem, and nifedipine. Erythrophores were treated for at least 5 minutes with 1 nM NE prior to exposure to the L-type $Ca^{2+}$ channel blockers. Dispersion response was calculated as an area occupied by cells after exposure for 10 minutes divided by an area occupied prior to exposure. Curves labeled with (+$Ca^{2+}$) were performed in PSS containing 1.8 mM added $Ca^{2+}$. Curves labeled with (-$Ca^{2+}$) were performed without added $Ca^{2+}$. Each of the above chemicals added directly to erythrophores produces pigment dispersion but does not alter melanophores. The mode of action for each of these agents is similar in that they work by blocking the passage of calcium ions from extracellular space into the cytoplasm. Each of these chemicals induces this response in a dose dependent manner. Control experiments, also seen in FIG. 21, performed in solutions without added calcium failed to induce pigment dispersion response so that a direct role of intracellular calcium concentration in these cells is implicated.

Erythrophore dispersion caused by $Ca^{2+}$ channel inhibition was examined by imaging continuously during an experiment where two different verapamil concentrations were added in succession Continuous pretreatment with norepinephrine caused pigment to aggregate in cells that normally have dispersed pigment. Upon addition of a dose of 1 nM verapamil, rapid dispersion followed until the cell chamber was flushed of verapamil by continued flow of buffered solution with added norepinephrine. This allowed the cells to re-aggregate rapidly until a second, stronger dose (100 nM) of verapamil was added. This stronger dose of verapamil caused the cells to disperse almost as completely as possible and the dispersion was sustained as long as verapamil was present. This demonstrates not only the sensitivity of erythrophores to $Ca^{2+}$ channel inhibitors, but also the ability of these cells to repeatedly and consistently respond.

Figure 22:
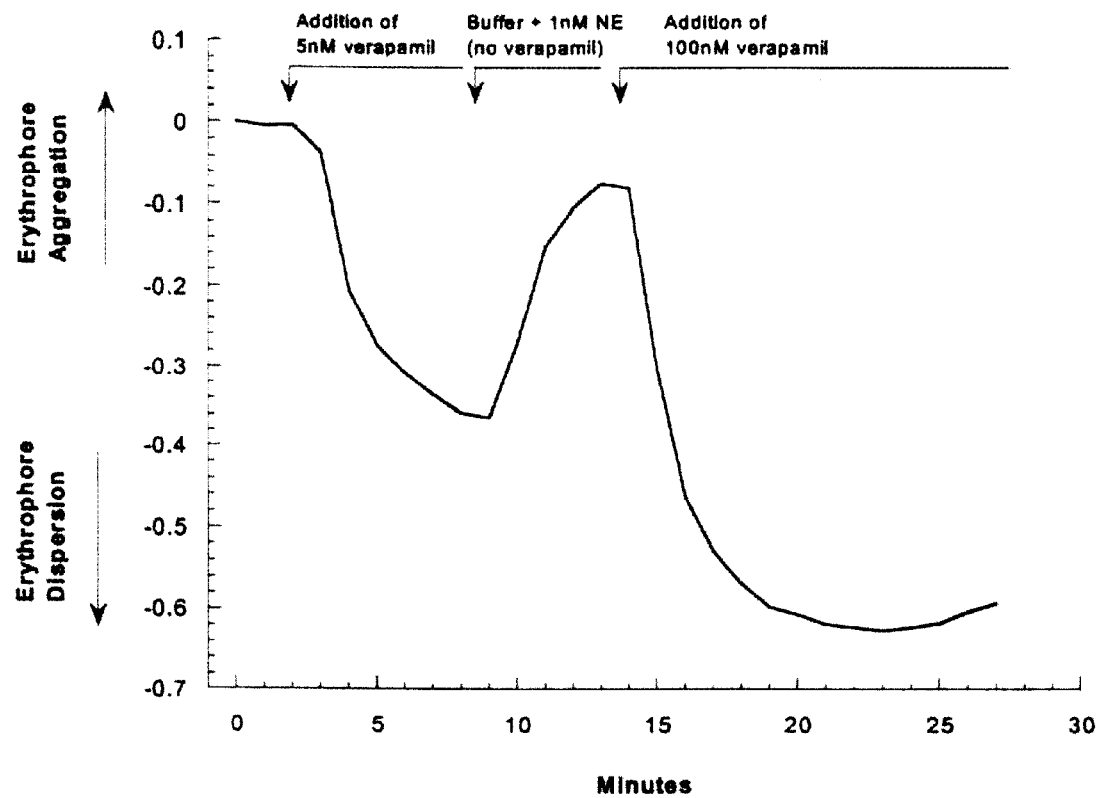
FIG. 22 contains a graph of erythrophore response to verapmil.

FIG. 22 contains a graph of erythrophore aggregation/dispersion as a function of time during which various doses of verapamil are applied. Initially, the erythrophores are exposed to NE and then exposed to 5 nM verapamil causing pigment dispersion. During flushing, there was an exposure to 1 nM NE without verapmil, producing re-aggregation. Exposure to 100 nm verapmil produced a larger dispersion.

Figure 23:
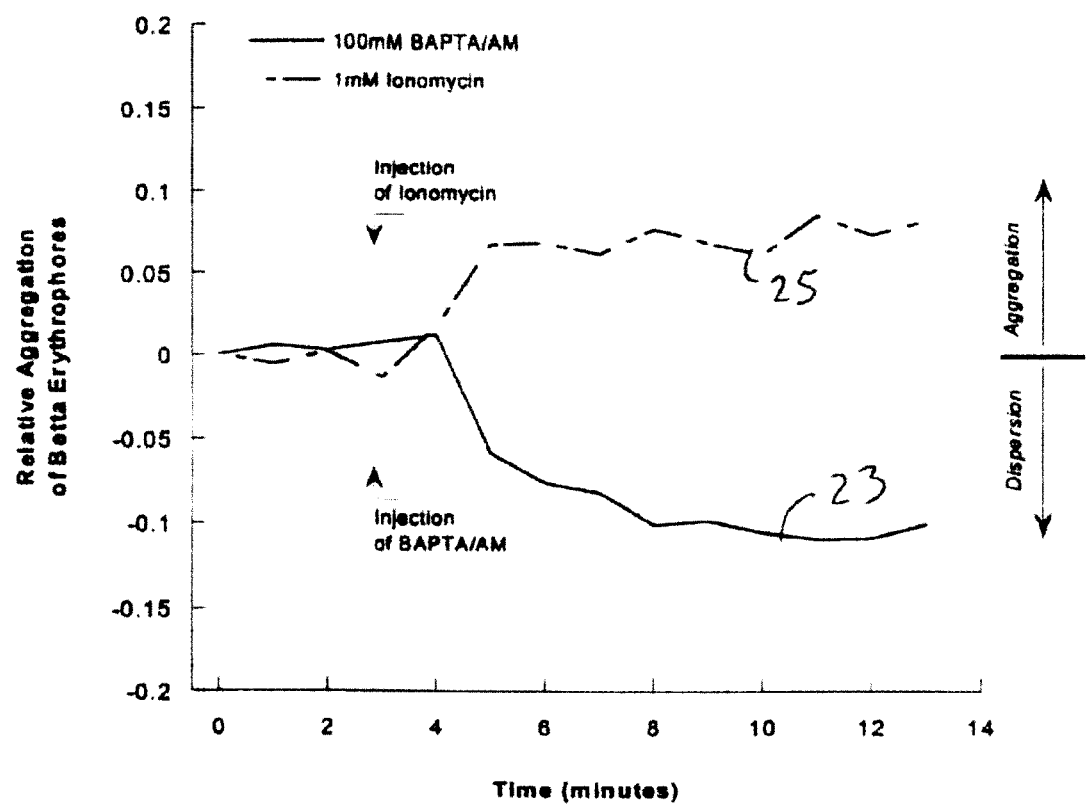
FIG. 23 contains graphs illustrating erythrophore response to BAPTA/AM and ionomycin.

To confirm the results observed by raising intracellular $Ca^{2+}$ concentration with $Ca^{2+}$ channel blockers, the membrane-permeable acetylmethyl (AM) form of the $Ca^{2+}$ chelator BAPTA was added to erythrophores. The lower intracellular $Ca^{2+}$ concentration ensuing from chelation resulted in pigment dispersion as seen in graph in FIG. 23. These results led to the question of whether increasing intracellular $Ca^{2+}$ levels would result in an opposite effect as decreasing levels, namely by aggregating the pigment in erythrophores. Treating erythrophores with the $Ca^{2+}$ ionophore ionomycin tested this idea The results of this experiment can also be seen in FIG. 23 in graph 25. Upon addition of ionomycin to erythrophores a slight, but sustained aggregation is apparent, confirming that $Ca^{2+}$ concentration can independently modulate both dispersion and aggregation in erythrophores.

Figure 24:
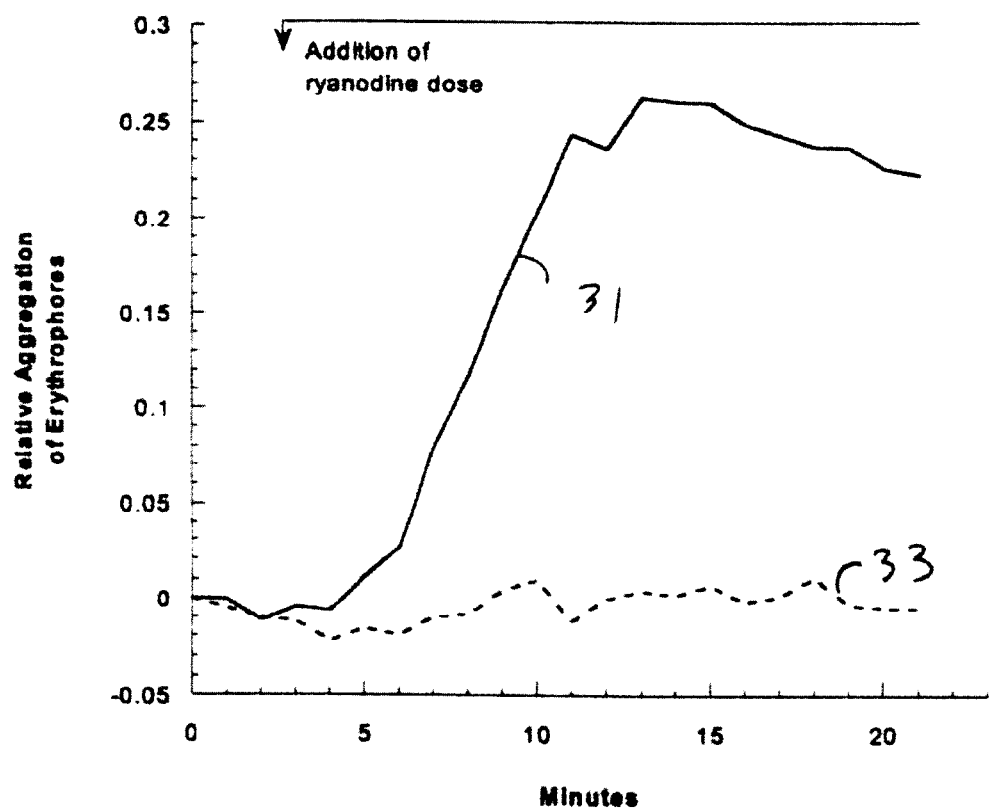
FIG. 24 illustrates erythrophore response to high and low concentrations of ryanodine.

The presence of intracellular $Ca^{2+}$ channels in erythrophores was also investigated. Such ryanodine and $IP_3$ receptors are present on the endoplasmic and sarcoplasmic reticulum in many other cell types and control the flow of $Ca^{2+}$ from intracellular stores. Again the pharmacological applications of receptor modulators were used on ryanodine receptors. $IP_3$ receptors were not examined here because of their cross-reactivity in other signaling pathways and because of the lack of specific cell-permeable agonists. Ryanodine receptors were screened for by the application of the agonist ryanodine as seen in FIG. 24. Ryanodine is a membrane permeable molecule that has an unusual biphasic effect on intracellular receptors because at low concentrations (1 nM–100 nM) ryanodine acts as an agonist of the receptor. However, at high concentrations (>1 μM) ryanodine acts as an antagonist of the same receptors. Referring to FIG. 24, curve 31 corresponding to 10 nM ryanodine is associated with increasing aggregation while curve 33, corresponding to 10 μM ryanodine is associated with decreasing aggregation. This information is consistent with the data shown in FIG. 24. A 10 μM dose of ryanodine onto erythrophores did not produce any morphological change in the cells, signifying that no $Ca^{2+}$ was released into the cytoplasm from intracellular stores. However, a 10 nM dose of Referring to Table 1A, cytosensors can be configured for a variety of applications such as identifying, quantifying, or discriminating among and between neurotransmitters, adrenergic agonists, adrenergic antagonists, serotonergic agonists, serotonergic antagonists, hormones, cytoskeletal inhibitors, cAMP and Ca++ signal transduction modulators, membrane voltage modulators, neurotoxins, and protein kinase modulators. Effects of some $Ca^{2+}$ modulating chemicals are listed in Table 1A. Pharmacological results using $Ca^{2+}$ channel antagonists indicate the presence of L-type channels in *Betta splendens* erythrophores.

TABLE 1A

Effects of $Ca^{2+}$ modulating chemicals on Betta erythrophores

| | Morphology Effect | | |
|---|---|---|---|
| $Ca^{2+}$ channel antagonists[a] | Dispersion | Aggregation | Comments |
| Verapamil (@<1 μM) | Yes | No | Phenylalkylamine, L-type specific |
| Diltiazem (@<1 μM) | Yes | No | Benzothiazepine, L-type specific |
| Nimodipine (@<1 μM) | Yes | No | Dihydropyridine, L-type specific |
| Nifedipine (@<1 μM) | na[c] | na | Dihydropyridine, L-type specific |
| μ-Conotoxin GVIA | No | No | L-type channels are insensitive |
| $Ca^{2+}$ channel agonists | | | |
| Bay K8644 | Na | na | Dihydropyridine, L-type specific |
| High [K+](>50 mM) | No | Yes (slight) | |
| $Ca^{2+}$ chelating chemicals | | | |
| EGTA (extracell.) | na[c] | na | |
| BAPTA/AM (intracell.) | Yes | No | Cell permeable, $Ca^{2+}$ specific |
| Ionophores | | | |
| A23187 | No | No | |
| Ionomycin | No | Yes | More effective than A23187 |
| Intracellular $Ca^{2+}$ channel agonist | | | |
| Ryanodine[b] | | | Mediates $Ca^{2+}$ release from ER |
| Release $Ca^{2+}$ @nM-μM | No | Yes | |
| Inhibit $Ca^{2+}$ release @>1 μM | No | No | |
| Intracellular $Ca^{2+}$ channel antagonist | | | |
| Ruthenium red | na[c] | na | |
| Microsomal $Ca^{2+}$-ATPase inhibitor | | | |
| Thapsigargin (@<1 μM) | No | Yes | Results in elevated cytoplasmic $Ca^{2+}$ levels | ryanodine onto erythrophores did produce a sustained aggregation response. This result is consistent with the biphasic response profile of ryanodine. Images of erythrophores treated with low and high concentrations of ryanodine are consistent with the results of FIG. 24. The aggregation response seen at a low concentration (10 nM) of ryanodine suggests that ryanodine receptors are mediating the release of $Ca^{2+}$ from the endoplasmic reticulum into the cytoplasm.

$Ca^{2+}$ channels are involved in the bi-directional movement of intracellular vesicles in erythrophores. There is no corresponding calcium dependence in melanophores, and so the combined observation of erythrophores and melanophores in response to pharmacological agents can verify or refute the possibility that a given agent acts upon calcium regulating molecular targets within the cells. Such a capability of chromatophores is established by the showing that the requirement for extracellular calcium for pigment movements and the effects of numerous calcium-modulating agents on pigment movements are exclusive to erythrophores and not melanophores.

Additional chromatophore responses to various agents and classes are listed in Table 1B. Response times are indicated as X (minutes), XX (tens of minutes), or hours (X=1–6 hr, XX=6–24 hr). Threshold concentrations are indicated in parts per billion (X=1 to 100 PPB, XX=100 to 1000 PPB), parts per million (X=1 to 100 PPM, XX=100 to 1000 PPM), or parts per thousand (X=1 PPT or higher). The nature of the chromatophore response is summarized for melanophores, erythrophores, xanthophores, iridophores, or combinations thereof, or on chromatophores in representative types of 2-cell cytosensor (chromatophore/neuronal cell, chromatophore/bacterial cell, chromatophore/fungal cell, chromatophore/protozoal cell). Pigment aggregation and dispersion are indicated as Aggr. and Disp., respectively. Aggregation followed by impairment is indicated as A/I and fish scale responses are indicates as FS. Chromatophore impairments is indicated as Imp.

The 2-cell cytosensors associated with Table 1B can include chromatophores and a small inoculum of a selected microbial cell (bacteria, fungus, protozoan) as the second cell type. To test its potency, a potential antibiotic is added to the 2-cell cytosensor. At a later time the chromatophores are evaluated by a known test agent (such as norepinephrine). If the antibiotic is potent, the microbial inoculum will not have thrived and toxified the chromatophores, and so the chromatophores will exhibit a "normal response" to the known test agent. If the antibiotic is not potent, however, the chromatophores will have become toxified by the microbe and the chromatophores will not respond normally to the test agent. Such versions of the 2-cell cytosensor are capable of detecting numerous antibiotics beyond those listed in Table 1B. Moreover, the 2-cell cytosensor is useful because a normal response further indicates that the antibiotic is not harmful to the animal cells (chromatophores). Useful antibiotics such as penicillin, having low animal cell toxicity, are readily detectable in this manner.

Tables 1C–1D list additional agents and categories of agents having chromatophore responses.

TABLE 1B

Chromatophore Response to Categories of Agents

| Functional Category of Agent | Specific agent | Response time | | Threshold concentration | | | Chromatophore response | | | | 2-Cell Cytosensor (second cell type included) |
|---|---|---|---|---|---|---|---|---|---|---|---|
| | | Min. | Hr. | PPB | PPM | PPT | Melano-phores | Erythro-phores | Xantho-phores | Irido-phores | |
| Neurotransmitters | Norepinephrine | X | | | X | | Aggr. | Aggr. | Disp. | Hue changes (FS) | |
| | Adenosine | X | | | XX | | Disp. | | | | |
| | Dopamine | X | | | XX | (FS) | Aggr. | | | | |
| | Serotonin | X | | | X | | Partial Aggr. | | | | |
| | Acetylcholine | X | | | X | | | | | | Eryth. Aggr. (neuronal cells) |
| | ATP | X | | | X | | | | | | Erythr. Aggr. (neuronal cells) |
| Adrenergic agonists | Clonidine | X | | XX | | | Aggr. | Aggr. | Disp. | | |
| | Naphazoline | X | | XX | | | Aggr. | Aggr. | Disp. | | |
| | Oxymetazoline | X | | XX | | | Aggr. | Aggr. | Disp. | | |
| | Tetrahydrozoline | X | | XX | | | Aggr. | Aggr. | Disp. | | |
| Adrenergic antagonists | Phentolamine | X | | XX | | | Blocks norepinephrine | | | | |
| | Yohimbine | X | | X | | | Blocks norepinephrine | | | | |
| | Phenoxy-benzamine | X | | X | | | Blocks norepinephrine | | | | |
| Serotonergic antagonists | | X | | XX | | | Blocks serotonin | | | | |
| Cholinergic agonists | Carbachol | X | | | X | | | | | | Erythr. Aggr. (neuronal cells) |
| Hormones | MCH | X | | X | | | Aggr. | | | | |
| | MSH | X | | X | | | Disp. | Disp. | | Hue changes (isolated iridophores) | |
| | Substance P | XX | | | | | | | | Hue changes (FS) | |
| Cytoskeletal inhibitors | Colchicine | XX | | | XX | | Imp. | | | | |
| | Cytochalasin D | XX | | | XX | | Imp. | | | | |
| cAMP Signal transduction modulators | CAMP | X | | XX | | | Disp. (microinjected and permeabilized melanophores) | | | | |
| | Forskolin | X | | XX | | | Disp. | | | | |
| | Caffeine | XX | | XXX | | | Disp. | | | | |
| Ca++ Signal transduction modulators | Verapamil | X | | X | | | | | Disp. | | |
| | Diltiazem | X | | XX | | | | | Disp. | | |
| | Nifedipine | X | | XX | | | | | Disp. | | |
| | Ryanodine | X | | XX | | | | | Aggr. | | |
| Membrane voltage modulators | Depolarizing K+ in medium | X | | | | X | Aggr. (FS) | Aggr. | | | Erythr. Aggr. (neuronal cells) |
| | Tricaine | X | | | X | | Disp. (FS) | | | | |
| Neurotoxins | Capsaicin | XX | | | X | | Hollow-ing (FS) | | | | |
| | Latrotoxin (spider venom) | X | | XX | | | | Aggr | | | Erythrophore Aggr. (neuronal cells) |
| | w-Conotoxin (peptide neurotoxin) | XX | | | X | | | Disp. | | | |
| | Saxitoxin | XX | | | XX | | Aggr. | Aggr. | | | |

TABLE 1B-continued

Chromatophore Response to Categories of Agents

| Functional Category of Agent | Specific agent | Response time Min. | Response time Hr. | Threshold concentration PPB | Threshold concentration PPM | Threshold concentration PPT | Chromatophore response Melano- phores | Chromatophore response Erythro- phores | Chromatophore response Xantho- phores | Chromatophore response Irido- phores | 2-Cell Cytosensor (second cell type included) |
|---|---|---|---|---|---|---|---|---|---|---|---|
| | (Paralytic shellfish toxin) | | | | | | (FS) | | | | |
| Protein kinase modulators | Protein kinase inhibitor H-8 | X | | | XX | | Disp. | | | | |
| | Protein kinase inhibitor H-9 | X | | | XX | | Disp. | | | | |
| | Protein kinase inhibitor K252a | X | | | X | | Disp. | | | | |
| Caustic irritants | Salicylate | XX | | | XX | | Imp. (FS) | | | | |
| | Formaldehyde | XX | | | XX | | Imp. (FS) | | | | |
| | Ammonium | XX | | | XX | | Imp. (FS) | | | | |
| | Hydrogen peroxide | XX | | | XX | | Imp. (FS) | | | | |
| | Cyanide | | X | | X | | Imp. (FS) | | | | |
| Heavy metals | Pb | XX | | | | X | Imp. (FS) | | | | |
| | Cu | XX | | | | X | Imp. (FS) | | | | |
| | Ag | XX | | | | X | Imp. (FS) | | | | |
| | Ni | XX | | | | X | Imp. (FS) | | | | |
| Polyaromatic hydrocarbons | Pyrene | XX | | | X | | Imp. | | | | |
| | 1,2-Benzanthracene | XX | | | X | | Imp. | | | | |
| | Fluoranthene | XX | | | X | | Imp. | | | | |
| | Acenapthene | XX | | | X | | Imp. | | | | |
| Organo-phosphate nerve agents | DFP | X | | | X | | Imp. | | | | |
| | DFP | XX | | | X | | A/I (FS) | Aggr. (FS) | Hue changes (FS) | | |
| | Paraoxon | XX | | | XX | | A/I (FS) | Aggr. (FS) | Hue changes (FS) | | |
| | Mipafox | | X | | XX | | A/I (FS) | Aggr. (FS) | Hue changes (FS) | | |
| | EPN | | X | | XX | | | | | | |
| | Mevinphos | | X | | | X | Imp. (FS) | Imp. (FS) | Hue change, then Imp. (FS) | | |
| | Dichlorvos | | X | | | X | Imp. (FS) | Imp. (FS) | Hue change, then Imp. (FS) | | |
| | Trichlorfon | | X | | | X | Imp. (FS) | Imp. (FS) | Hue change (FS) | | |
| Pyschogenic agents | Cocaine | X | | | | | Agr. (FS) | | | | |
| | Cannabinoid CP-55940 | | X | | XX | | Disp. (FS) | | | | |
| | Amphetamine | XX | | | X | | Aggr. (FS) | | | | |
| | Desipramine | XX | | | X | | Aggr. (FS) | | | | |
| Various drugs and agents | Pheniramine (antihistamine) | XX | | | XX | | Disp. | | | | |
| | PMSF (enzyme inhibitor) | XX | | | X | | Imp. (FS) | | | | |
| | Hydrocortisone | | XX | | X | | Hyp.D. | HypD. | | | |
| | Bradykinin | X | | | XX | | | | | | Eryth. Aggr. (neuronal cells) |
| | Guanethidine | XX | | | X | | Disp. (FS) | | | | |
| | Histamine | X | | | XX | | Aggr. (FS) | | | | |
| | Imipramine | X | | | X | | Disp. (FS) | | | | |
| Algal toxins (48 sources) | Algal extracts. (six different species of marine algae) | X (various response times) | | | X (range of concentrations, from 0.3 ppm to 10 ppm) | | Aggr. | | | | |
| | Algal extracts. (nineteen different species of marine algae) | X (various response times) | | | X (range of concentrations, from 0.3 ppm to 10 ppm) | | A/I | | | | |

TABLE 1B-continued

Chromatophore Response to Categories of Agents

| Functional Category of Agent | Specific agent | Response time Min. Hr. | Threshold concentration PPB PPM PPT | Melano- phores | Erythro- phores | Xantho- phores | Irido- phores | 2-Cell Cytosensor (second cell type included) |
|---|---|---|---|---|---|---|---|---|
| | Algal extacts. (seventeen different species of marine algae) | X (various response times) | X (range of concentrations, from 0.3 ppm to 10 ppm) | Imp. | | | | |
| | Algal extracts. (six species of marine algae) | No detected response at up to 10 ppm | | | | | | |
| Algal toxins (pure sources) | Brevetoxin | X | X | Aggr. (FS) | | | | |
| | Curacin A | X | X | Aggr. and Imp. (FS) | | | | |
| Bacterial toxins | Cholera toxin | X | X | Imp. | | | | |
| | Pertrussis toxin | X | X | Imp. | | | | |
| | Staph alpha-toxin | X | X | Aggr. | | | | |
| Known pathogenic bacteria (9 tested strains) | *Bacillus cereus* | X | | | Aggr. | Aggr. | | |
| | *Shigella dysenteria* | X | | | Aggr. | Aggr. | | |
| | *Shigella sonnei* | X | | | Aggr. | Aggr. | | |
| | *Salmonella typhi* | X | | | Aggr. | Aggr. | | |
| | *Salmonella enteriditis* | X | | | Aggr. | Aggr. | | |
| | *Escherichia coli* O157:H7 | X | | | Aggr. | Aggr. | | |
| | *Vibrio cholera* | X | | | Aggr. | Aggr. | | |
| | *Clostridium sp.* | X | | | Aggr. | Aggr. | | |
| | *Pseudomonas sp.* | No detected response | | Imp. (FS) | | | | |
| Non-pathogenic bacteria (3 strains) | *Escherichia coli* JM101 | No detected response | | | | | | |
| | *Bacillus subtilis* | No detected response | | | | | | |
| | *Lactococcus lactis* | No detected response | | | | | | |
| Bacterial Isolates (34 tested) | Twenty-four natural isolates of bacteria, collected from air and water sources | X | X | | Various acute responses and impaired responses | | | |
| | Six broths of anaerobic bacteria, prepared from isolates collected from outdoor soil samples | X (range of times) | X (range of concentrations) | | Various acute responses and impaired responses | | | |
| | Exposure to single bacterial colonies collected by exposing agar plates to indoor air (four distinct colonies) | XX | Single-colony dose | | Various acute responses and impaired responses | | | |
| Antibacterial agents | Penicillin | XX | X | | | | | Normal response (bacterial inoculum) |
| | Streptomycin | XX | X | | | | | Normal response (bacterial inoculum) |
| | Tetrasycline | XX | X | | | | | Normal response (bacterial |

TABLE 1B-continued

Chromatophore Response to Categories of Agents

| Functional Category of Agent | Specific agent | Response time | | Threshold concentration | | | Chromatophore response | | | | 2-Cell Cytosensor (second cell type included) |
|---|---|---|---|---|---|---|---|---|---|---|---|
| | | Min. | Hr. | PPB | PPM | PPT | Melano- phores | Erythro- phores | Xantho- phores | Irido- phores | |
| | Trimethoprim-sulfamethoxalzole | | XX | | X | | | | | | inoculum) Normal response (bacterial inoculum) |
| | Nalidixic acid | | XX | | X | | | | | | Normal response (bacterial inoculum) |
| Fungi (14 tested) | Ten uncharacterized fungal broths. prepared from isolates collected from outdoor soil samples and air samples. | X | | X | | | Various acute responses and impaired responses | | | | |
| | Exposure to single fugal colonies, collected by exposing agar plates to indoor air (four distinct colonies representing four distinct fungal species) | XX | | Single-colony dose | | | Various acute responses and impaired responses | | | | |
| Antifungal agents | Amphotericin B | | XX | | X | | | | | | Normal response (fungal inoculum) |
| Antiprotozoal agents | Metronidazole | | XX | | X | | | | | | Normal response (protozoal inoculum) |
| | Chloroquine | | XX | | XX | | | | | | Normal response (protozoal inoculum) |
| | Quinine sulfate | | XX | | XX | | | | | | Normal response (protozoal inoculum) |

TABLE 1C

Additional categories and agents.

| Categories | Detected agents | Likely capability |
|---|---|---|
| DRUGS ACTING AT SYNAPTIC AND NEUROEFFECTOR JUNCTIONAL SITES | | |
| Neurotransmission: The autonomic and somatic motor nervous systems. | Norepinephrine Adenosine ATP | |
| Muscarinic receptor agonists and antagonists. | Acetylcholine Carbachol | |
| Anticholinesterase agents. | DFP, Paraoxon, Mipafox, EPN, Mevinphos, Dichlorvos, Trichlrofon | |
| Agents acting at the neuromuscular junction and autonomic ganglia. | Acetylcholine | |

TABLE 1C-continued

Additional categories and agents.

| Categories | Detected agents | Likely capability |
|---|---|---|
| Catecholamines, sympathomimetic drugs, and adrenergic receptor antagonists. | Norepinephrine, Dopamine, Cloridine, Naphazoline, Oxymetazoline | |
| 5-Hydrosytryptamine (Serotonin) receptor agonists and antagonists. | Serotonin Ketanserin | |
| DRUGS ACTING ON THE CENTRAL NERVOUS SYSTEM | | |
| Neurotransmission and the central nervous system. | — | |
| History and principles of anesthesiology. | — | |
| General anasthetics. | Not tested | Barbituates Benzodiazepines |
| Local anesthetics. | Tricaine, Cocaine, Saxitoxin | |
| Therpapeutic gases. | Not tested | Nitric oxide |
| Hypnotics and sedatives: Ethanol | Not tested | Benzodiazepines |
| Drugs and the treatment of psychiatric disorders: Psychosis and anxiety. | Clonidine, Reserpine | Benzodiazepines |
| Drugs and the treatment of psychiatric disorders: Depression and mania. | Desipramine Imipramine | |
| Drugs effective in the therapy of the epillepsies. | Not tested | Barbituates Benzodiazepines |
| Drugs effective in the therapy of migraine. | Ketanserin, Diltiazem, Nifedipine, Verapamil | |
| Treatment of central nervous system degenerative disorders. | Dopamine, Acetylcholine, Carbachol | |
| Opioid analgesics and antagonists. | Not tested | Morphine |
| AUTACOIDS: DRUG THERAPY OF INFLAMMATION | | |
| Histamine, Bradykinin and their antagonist. | Histamine, Pheniramine, Bradykinin | |
| Lipid-derived autacoids: Eicosinoids and platelet-activating factor. | Not tested | Unknown |
| Analgesic-antipyretic and antiinflammatory agents and drugs employed in the treatment of gout. | Colchicine | Vinbistine |
| Drugs used in the treatment of asthma. | Caffeine | Theophylline |
| DRUGS AFFECTING RENAL AND CARDIOVASCULAR FUNCTION | | |
| Diuretics. | Not tested | FK453, adenosine receptor antagonist |
| Vasopressin aud other agents affecting the renal conservation of water. | Protein kinase inhibitors H-8, H-9, K252a | |
| Renin and angiotensin. | Not tested | Angiotensin |
| Drugs used in the treatment of myocardial ischemia. | Diltiazam, Nifedipine Verpamil | Digoxin |
| Antihypertensive agents and the drug therapy of hypertension. | Guanethidine, Reserpine, Diltiazem, Nifedipine, Verapamil | |
| Pharmacological treatment of heart failure. | Phenolamine Nifedipine | |
| Antiarrythmic drugs. | Clonidine, Adenosine, Diltiazem, Nifedipine, Veraparamil | |
| Drugs used in the treatment of hyperlipoproteinemias. | Not tested | Unknown |
| DRUGS AFFECTING GASTROINTESTINAL FUNCTION | | |
| Agents for control of gastric acidity and treatment of peptic ulcers. | Metronidazole | |
| Agents affecting gastrointestinal water flux and motility; emesis and antiemetics; bile acids and pancreatic enzymes. | Cannabinoid CP-55940 | Metoclopramide Phenothiazines |
| DRUGS AFFECTING UTERINE MOBILITY | | |
| Agents that cause contraction or relaxation of the uterus. | Nifedipine | |
| CHEMOTHERAPY OF PARASITIC INFECTIONS | | |
| Drugs used in the chemotherapy of protozoal infections: Malaria. | Chloroquine, Quinine sulfate, Tetracycline, Sulfonamide | |
| Drugs used in the chemotherapy of protozoal infections: Trypanosomiasis, leishmaalasis, amebiasis, glardiasis, trichhomonlasis, and other protozoal infections. | Chloroquine, Metronidazole | |
| Drugs used in the chemotherapy of helminthiasis. | Not tested | |

TABLE 1C-continued

Additional categories and agents.

| Categories | Detected agents | Likely capability |
|---|---|---|
| CHEMOTHERAPY OF MICROBIAL DISEASES | | |
| Antimicrobial agents: General considerations. | | |
| Antimicrobial agents: Sulfonamides, trimethoprim-sulfamethoxazole, quinolones, and agents for urinary tract infections. | Trimethoprim-sulfamethoxazole, Nalidixic acid | |
| Antimicrobial agents: Penicillins, cephalesporins, and other beta-lactam antibiotics. | Penicillin | Ampicillin |
| Antimicrobial agents: The aminoglycosides. | Streptomycin | Neomycin<br>Kanamycin |
| Antimicrobial agents: Tetracyclines, chloramphenicol, erythromycin, and miscellaneous antibacterial agents. | Tetracycline | Chloramphenicol, Erythromycin, Vancomycin |
| Antimicrobial agents: Drugs used in the chemotherapy of tuberculosis and leprosy. | Streptomycin | Isoniazid<br>Rifampin |
| Antimicrobial agents: Antifungal agents. | Anphotericin B | |
| Antimicrobial agents: Antiviral agents. | Not tested | Unknown |
| CHEMOTHERAPY OF NEOPLASTIC DISEASES | | |
| Antineoplastic agents. | Colchicine | Vinca alkaloids<br>Taxol |
| DRUGS USED FOR IMMUNOMODULATION | | |
| Immunomodulators: Immunosuppressive agents and immunostimulants. | Not tested | Unknown |
| DRUGS ACTING ON THE BLOOD AND THE BLOOD-FORMING ORGANS | | |
| Hematopoetic agents: Growth factors, minerals, and vitamins. | Not tested | Unknown |
| Anticoagulant, thrombolytic, and antiplatelet drugs. | Not tested | Unknown |
| HORMONES AND HORMONE ANTAGONISTS | | |
| Adenohypophyseal hormones and their hypothalamic releasing factors. | MSH | |
| Thyroid and antithyroid drugs. | Not tested | Unknown |
| Estrogens and progestins. | Not tested | Unknown |
| Androgens. | Not tested | Unknown |
| Adrenecorticotropic hormone; adrenecortical steroids and thier synthetic analogs; inhibitors of the synthesis and actions of adrenocortical hormones. | Hydrocortisone | |
| Insulin, oral hypoglycemic agents, and the pharmacology of the endocrine pancreas. | Verapamil<br>Clonidine | Insuhn |
| Agents affecting calcification and bone turnover: Calcium, phosphate, parathyroid hormone, vitamin D, calcitonin, and other compounds. | Not tested | Unknown |
| THE VITAMINS | | |
| Water-soluble vitamins: The vitamin B complex and ascorbic acid. | Not tested | Unknown |
| Fat soluble vitamins: Vitamin A, K and E. | Not tested | Unknown |
| DERMATOLOGY | | |
| Dematological pharmacology. | Hydrocortisone, Capsaicin,<br>Tetracycline, Colehicine | Topical antibacterial agents<br>Topical antibacterial agents |
| OPTHAMOLOGY | | |
| Ocular pharmacology. | Cocaine, Carbacol, DFP, Naphazoline, Tetrahydrozoline | |
| TOXICOLOGY | | |
| Heavy metals and heavy-metal antagonists. | Pb, Cu, Ag, Ni | |
| Nonmetallic environmental toxicants: Air pollutants, solvents, vapors, and pesticides. | Polyaromatic hydrocarbons<br>Organophosphates<br>Cyaninde | Pyrethrin insecticides |

TABLE 1D

Additional classes and agents.

| Class Agent | Detection Demonstrated | Detection Likely |
|---|---|---|
| ANALGESICS AND NONPRESCRIPTION PREPARATIONS | | |
| Acetaminophen | | Not known |
| Salicylates | X | |
| Nonsteroidal antiinflammatory agents | | Not known |
| Iron | | Not known |
| Vitamins | | Not known |
| Dieting agents and regimens | X | |
| Caffeine | X | |
| PRESCRIPTION MEDICATIONS | | |
| Theophylline | | X |
| Hypoglycemic agents | X | |
| Anticonvulsants | X | |
| Antihistamines | X | |
| Antocoagulants | | Not known |
| Antituberculous agents | | X |
| Antimarial agents | X | |
| Ergotamines | | Not known |
| Antibiotics: Penicillin and other substances that cause anaphylaxis and anaphylactoid reactions | X | |
| Antineoplastic agents | X | |
| Digitalis | | X |
| Antihypertensive agents | X | |
| Antidysrhythmic agents | X | |
| SECTION III: PSYCHOPHARMACOLOGIC MEDICATIONS | | |
| Cyclic antidepressants | X | |
| Neuroleptic agents | | X |
| Monoamine oxidase inhibitors | | X |
| Lithium | | Not known |
| Opioids | | Not known |
| Sedative-hypnotic agents | | X |
| ALCOHOLS AND DRUGS OF ABUSE | | |
| Ethanol | | X |
| Methanol, ethylene glycol, and isopropanol | | X |
| Cocaine | X | |
| Amphetamines | X | |
| Phencyclidine | | Not known |
| Lysergic acid diethylamide and other psychedelics | X | |
| Marijuana | | X |
| Disulfiram and disulfiramlike reactions | | Not known |
| Substance withdrawal | N/A | |
| FOOD POISONING | | |
| Food poisoning | X | |
| Staphylococcus aureus | X | |
| Bacillus cereus | X | |
| Clostridium sp. | X | |
| Salmonella sp. | X | |
| Vibrio cholera | X | |
| Ciguatera seafood poisoning | | X |
| Shelfish poisoning (saxitoxin, brevetoxin) | X | |
| Botulism | | X |
| BOTANICALS | | |
| Mushrooms: Toxic and hallucinogenic | X | X |
| Herbal preparations | X | X |
| Plants | X | X |
| Nicotine | X | |
| HEAVY METALS | | |
| Arsenic | | Not known |
| Lead | X | |
| Mercury | | Not known |
| Cadmium and other metals and metalloids | X | |
| HOUSEHOLD TOXINS | | |
| Antiseptics, disinfectants, and sterilants | X | |
| Camphor and mothballs | | Not known |
| PESTICIDES | | |
| Insecticides: Organophosphates and carbamates | X | |
| Insectisides: Chlorinated hydrocarbons, pyrethrins, and DEET | | Not known |
| Rodenticides | | Not known |
| Herbisides: Paraqaut and diquat | | Not known |
| OCCUPATIONAL AND ENVIRONMENTAL TOXINS | | |
| Recognition and follow-up of workplace poisonings | N/A | |
| Methernoglobinemia | | Not known |
| Simple asphyxiants and pulmonary irritants | | X |
| Smoke inhalation | | X |
| Carbon monoxide | | X |
| Cyanide and hydrogen sulfide | X | |
| Hydrocarbons | X | |
| Caustics and batteries | | X |
| Hazardous materials releases | N/A | |
| Farm toxicology | X | |
| Art hazards | | X |
| TOXIC ENVENOMATIONS | | |
| Snakes and other reptiles | | X |
| Arthropods | X | |
| Marine animals | X | |

EXAMPLE EMBODIMENT 10

Optical changes in chromatophores are monitored and analyzed using a detection system configured to receive a light flux from a chromatophore population retained in a cell chamber such as that illustrated in the figures accompanying Example Embodiment 11. Cell chambers can be constructed using a series of layers that are laminated. Alternatively, a cell chamber can be formed using, for example, injection molding, casting, or machining. In a laminated cell chamber, one or more layers that define an interior of the chamber form a biomatrix layer on which the sensor cells are cultured. Some layers are configured to provide fluid interconnect and transport for delivery of samples and other reagents. One or more of the layers is transparent to permit detection of optical changes in the chromatophores. Biocompatible materials are selected for the cell chamber and are generally durable materials that tolerate sterilization processes. Suitable materials include MELINEX 453 polyester because it is clear and hydrolytically stable at room temperature.

The laminated cell chamber is sandwiched between the two halves of a fluid interconnect that is in communication with a fluid delivery system and a sample injection system. Dimensions and hexagonal geometry of the fluid interconnect are selected for convenience in illuminating the sensor cells and recording changes in the sensor cells.

Construction of a cell chamber using a lamination process permits cell chamber geometry and fluid interconnects to be configured as required. In addition, the lamination method permits rapid, inexpensive chamber designs so that cell configurations can be selected for a particular application.

A pressure-sensitive adhesive(PSA) bonds laminated layers together to form the cell chamber. The PSA was selected to be biocompatible and hydrolytically stable. Hydrolytic stability was assessed by immersing PSA samples in water for several days. Some samples became milky in color, indicating that these sample were water permeable and likely to leak after prolonged water exposure. A very Dension adhesive FT 8311 was used because of its ability to withstand exposure to analytes and other materials. Further, biocompatibility tests were conducted on FT8311. Several chambers were fabricated and populated with cells. The populated chambers were monitored over several weeks to determine how long the cells would survive in the chambers. The only biocompatibility issue associated with the FT 8311 was that occasionally the adhesive would form bubbles that served as small antechambers next to the main cell chamber. If chemicals were used to clean the chambers prior to population, these chemicals can be caught in the antechambers and subsequently diffuse into the main chamber after cell population. The result is a drastic reduction in the shelf life of the cells.

The geometry of the cell chamber was based on the feeding requirements of sensor cells, the shear tolerance of sensor cells, and to afford an optimal field of view of the sensor cells, as described below.

In the first embodiment of a cytosensor the optics subsystem images the center 1 mm×1 mm area of the 3 mm×3 mm total sample area onto the color CCD array for optimal field of view. A Hastings triplet lens provided an achromatic, flat field of view.

The fluidics subsystem is designed such that the shear tolerance of cells is compensated for. In order to maintain cell viability the shear stress for a range of design options (chamber cross sectional area as measured by the chamber height) was calculated assuming viscous channel flow. Results show that the shear stress decreases rapidly with channel height and falls below the expected allowable of 1 $N/m^2$ at a height of 350 microns with a flow rate of 10 liters per minute in a one-millimeter wide channel. This result is inversely linear with flow rate (if the flow rate is reduced by a factor of 2 then the maximum channel height that yields the critical shear stress is increased by a factor of two).

The uniformity of delivery of analyte to the chamber and the flow conditions in the chamber depend on the downstream variability of the chamber cross section geometry. The chamber inlet section and the flow connections with the inlet channels influence the chamber flow conditions. These conditions were studied for a range of flow rates using a rapidly diffusing inlet (approximately 30° diffusion angle). Images of the flow within the chamber using a dissolved dye in water injected upstream of the chamber and allowed to flow steadily into the chamber show that a relatively uniform front of analyte can be achieved within the chamber and the frontal concentration gradient will depend on the diffusion coefficient of the analyte. Results were identical for a wide range of flow rates from 1 to 50 $\mu L$ per minute.

Fluidics connection points were built to specifications described elsewhere herein. The connection of the chamber to the analyte supply reservoir can be made in a variety of ways as long as the connections are bio-compatible and maintain their integrity (leak-proof) under pressures developed within the chamber. A simple connector was used which had an inlet tube at right angles to the chamber flow direction. The end of the tube was flanged, with the flanged portion held tight against the inlet port walls such that fluid could escape through the tube into the chamber. Other possibilities were used with success including o-ring seals and gasket material to prevent leaks.

A syringe injection system and syringe pumping system with the following attributes was used to deliver sample and aqueous medium to the cell chamber. This allowed easy variation of the flow rate ranges and provided long term operation at a set flow rate condition. The syringe pump was not absolutely continuous in that the supply mechanism provided very short duration steps to the syringe injection mode. Due to the very slow flow rates used this resulted in pulsing flow conditions within the chamber. This condition was found not to change the overall operation of the chromatophores.

Response time of the instrument includes sample arrival time at the cell chamber that can be adjusted according to the following considerations. The analyte can be delivered as a uniform front (slug) flow into the chamber. The time for the sample to arrive at the chamber can be varied by altering the set flow rate delivered by the pump or by varying the inlet channel length and cross sectional area. Sample calculations of the dead-volumes used in this embodiment show that the dead-volumes are sufficiently small. The waste stream was discarded, but can be expected to have other uses, such as providing a sample for further analysis to unspecified additional instrumentation, such as a mass spectrometer.

A schematic diagram of an optical system is given in Example Embodiment 11. A lens system was used to magnify the field of view and project it efficiently onto the imaging chip of the specified video camera. The cell chamber was illuminated with Nichia "white" LEDs which are based on a Ce:YAG phosphor over a blue InGaN LED emitter. The resulting spectrum still contains a large amount of the blue light in addition to a broad-band quasi-white emission from the phosphor. Filters or gratings can be used to adjust and/or dynamically alter the wavelength of light in order to accentuate the readouts from given colors of sensor cells. The illumination source can be filtered to test for optimum color illumination. The optimum color can then be matched by either filters or a combination of pure colored LEDs. Certain cells may reflect or transmit certain colors much better and thus provide more efficient detection. LED illumination adds no heat to the cells and requires very simple power of 10 mA at about 2.8 V. A periodically switching circuit can be used to modulate the light source during measurements to permit narrowband or lock-in detection.

A detection and identification algorithm uses a time sequence of images acquired either asynchronously or synchronously. In one embodiment, the images are collected on the average of one frame per second, but this rate is typically based on the rate of content change in the previous images. The system is capable of acquiring up to 30 images per second. The optimal sampling rate should match the estimated (on-line) rate of change of the image content.

Each image is represented by N×M array A, whose entries are P dimensional vectors. Such an array can be viewed as P dimensional discrete field. N and M define the grid, which conceptually divides the camera field of view into small rectangular regions called pixels or picture elements (e.g. field of view X by Y is divided into rectangles of (X/N) by (Y/M)). The P-dimensional discrete field model represents most of the known digital image formats. The image is initially acquired in RGB format. Thus each entry of A represents an average color from a picture element using P=3 dimensional vector of intensities of red, green and blue color components. Typically these intensities are normalized to take the values between 0 and 1. The generalized color histogram can be then viewed as a map of A into a 3 dimensional unit cube. Since the image is a discrete description of the optical appearance of the field of cells, the analyzer uses the colors and shapes to characterize the cell state.

Color segmentation based on reducing the number of distinct colors in the image to the maximum of K color-clusters (in the first embodiment, K is typically between 5 and 10). This reduction process is based on a generalized K-means algorithm. A color cluster is a set of colors which are "alike", and the colors from different clusters are "not alike". A quantitative description of a cluster is "an aggregation of points in a multi-dimensional space, such that the distance between any two points in the cluster is less than the distance between any point in the cluster and any point not in it." Intuitively clusters are connected regions of a multi-dimensional space containing a relatively high density of points, separated from other such regions by a region of a relatively low density of points. The segmentation takes place in a color histogram space. The RGB coordinates are transformed to a suitable color space where the distance between colors can be defined to ensure, for example, visual uniformity. The HSV (hue, saturation, and value) space is used in some examples. The distance D is calculated using quasi-periodic measure. The number of color classes K is adjusted adaptively using dynamic programming techniques. The smallest K is sought such that the variance (calculated using D) of each cluster does not exceed a priori specified threshold. The dynamic programing method allows re-using the initial segmentation for K classes to perform efficiently (K+1) class segmentation.

The segmentation is performed in an abstract color space. The clusters are next mapped onto a 2 dimensional image space where the geometrical shape of clusters is of interest. The morphological filtering is applied to each color class to eliminate small spatially isolated clusters and to merge the close ones. For example the cluster should be of the size expected for a chromatophore or a group of chromatophores.

The image segments represent now the areas filled with erythrophores, melanophores, and so on. The background is also isolated The temporal statistics and features of filtered clusters are next calculated and include: area, convex hull, bounding polygon, convex area, equivalent diameter, major and minor axis lengths, solidity, extent, orientation, eccentricity, and nth order moments (both spatial using Euclidean distance, and in color space using D measure).

The next two steps determine if the statistics representing various chromatophores change significantly over time based on analysis of series of images. Dynamic patterns (trends) of selected statistics are estimated (for example, area and 2nd order spatial moments), using a conditionally linear filter that generalizes Kalman ink filtering methods. This filter tests sequentially two alternative hypotheses about the parameters of a mixture of two distributions. The null hypothesis assumes that there is no bioagent present and that the cell's statistics are slowly varying. The alternative hypothesis assumes that after being exposed to a bioagent the cell statistics reach a distinct from the initial state equilibrium. A mixture of two Gaussian distributions is used with a slowly varying mean and variance of the first one and constant moments of the second. The test control parameters include probability of false alarm and detection delay. The acceptance of the second hypothesis marks the end of detection process and stops the image acquisition.

Time-dependent or dynamic pattern behavior is parametrically identified from the statistics waveform in the transition region (i.e. in the non-causal neighborhood of the time instant signaled by the detection algorithm). A BAR-MAX (Bilinear Auto-Regressive Moving Average) model is used, however various parameterized models can be used. The estimated model parameters are matched against a stored library of template signatures. These template signatures represent the results of controlled experiments when the living cells were exposed to known (type and concentration) bioactive agent. A proximity matrix approach is used but since the matching problem is of a low dimension (number of model parameters), various statistical (geometric) pattern recognition techniques can be used. Some of the cell responses to specific bioactive agents lend themselves to structural (syntactic) pattern recognition. In this approach the patterns are composed of simple sub-patterns. A sub-pattern can be built from simpler parts with grammatical techniques. Primitives (or the simplest sub-patterns) can be shared among many different experiments just relaxing the need for extensive experimentation and creation of large signature libraries. The outcomes of pattern matching for various statistics represent "votes" that establish a confidence level for agent identification.

Detection methods are conveniently implemented on a general-purpose microprocessor running Windows NT. The numerical calculations use fixed-point arithmetic and are ready for implementations on DSP type boards. The color segmentation algorithm is multi-threaded and can be easily ported to a multi-processor computer or multi DSP chip board. The identification and pattern recognition algorithms have hierarchical organization suitable for communication between several sensors in order to obtain more reliable detection results.

The representation of the cells state as a mathematical field and the general segmentation algorithm allow use of multi-spectral (not necessarily visual) images. Due to the sequential data processing the storage (i.e. memory) requirements are minimal. The system minimizes energy use by adapting the image sampling rates, which is an essential feature in mobile device operation.

Screen capture is shown with reference to Example Embodiment 11 based on detection results using 92 images that are acquired every 5 seconds. An alarm is triggered at a 60th frame, with a delay of two frames. Signature identification uses 10 frames (from frame 58 to 67). Frames 1 to 57 correspond to slowly changing statistics (null hypothesis). Frames 68 to 92 represent statistical equilibrium.

Microlamination techniques for fabricating microtechnology-based devices for micro-scale bio-devices are based on patterning and assembling thin shims and bonding them into a composite assembly. Microlamination typically involves three steps: 1) lamina patterning, 2) laminae registration to form an assembly, and 3) bonding of the assembly. A dual microchannel array fabricated by microlamination methods using polyimide as a thermal adhesive is shown in Example Embodiment 11. Microlamination permits fabrication of metal and/or polymeric devices with high aspect ratios in large production volumes.

Various microlamination schemes can be used. For example, polyester films can be patterned using 266 nm laser micromachining and bonded together using pressure-sensitive adhesives. Polycarbonate films can be patterned with 266 nm laser micromachining and bonded by solvent welding.

In some cell chambers, two laminae are used. One lamina is a flat cover plate that provides optical access into and sealing of the cell chamber. The other lamina is micromolded lamina. Such polymeric microchannels and chamber substrates can be fabricated using soft lithography methods and substrates can be formed in poly(dimethylsiloxane) (PDMS). The PDMS substrates can be formed using a combination of laser-based mask-making and contact photolithography. A mask can be made using selective laser ablation of a chromium-on-glass contact mask. Contact photolithography on a thick photoresist can be used to create a master mold of the microfluidic structure to be used as a mandrel in micromolding. An example of an SU-8 master mold for a particular embodiment is shown in the figures. In addition, bulk silicon etching can be used to create micromolding mandrels. A PDMS pre-polymer can be cast and cured on a mandrel.

Bonding of a cover plate onto a PDMS substrate can be handled conformally or adhesively. If necessary, cover plates can be readily assembled and disassembled by using nonadhesive, conformal contact with the molded PDMS substrate, allowing direct access to sample microchannels after an experiment. PDMS sample channels and chambers may be sealed permanently by oxidizing two PDMS surfaces in a plasma discharge and bringing them into conformal contact. Alternately, UV-curable adhesives may be used to permanently seal chambers. The use of adhesives may require the design and fabrication of adhesive reservoirs in the polymeric substrate.

PDMS substrates can be used as mandrels in a replica molding process to generate modest volumes of polyurethane or other crosslinked polymers. Replica molding is capable of fine-feature (submicron), high-aspect-ratio (20:1) pattern generation inside of microchannels and chambers, if necessary. Bonding between polyurethane and cover slips can be handled by a partial cure method or by UV-curable adhesives. The partial cure method simply involves putting the cover slip in contact with the polymeric substrate before it is fully polymerized and then finish curing the substrate.

High-volume molding and bonding can also be provided through injection molding and ultrasonic welding of cover slips to substrates.

Either tissue explants (scales, fin tissue), isolated chromatophores, or continually dividing populations of chromatophores can be employed in a cell-chamber. Chromatophore populations can also be populated into entrapped forms or encapsulated forms. In a specific embodiment, a cell chamber was populated with isolated Betta chromatophores, comprising approximately 1000 chromatophores (90% erythrophores, 9% melanophores, 1% iridophores) into a 1 $mm^2$ viewing area. The ratio of color types of chromatophores in a population can be varied to take advantage of distinct sensitivities of certain color classes of chromatophores. For example, there is evidence of selective sensitivity of erythrophores to *cholera* toxin, and melanophores to pertussis toxin. The numbers of chromatophores which are populated into the cytosensor can also be varied. Also, additional cell types such as PC12 cells, which can provide additional dimensions of sensitivity by being coupled to chromatophores, can also be included in the sensor cell populations.

The sensor cells are typically incorporated into a chamber or entrapped form at least one to three days prior to testing against an analyte, in order to give time for the cells to become firmly attached and adapted to in vitro conditions. That period can be lengthened to up to the maximum period that Betta chromatophores survive in vitro. During this storage period (the time between initializing the population and when the cells are used to test analytes), the cells have feeding requirements that are attended to according to the general criteria that a population of cells requires a flow rate of medium amounting to an exchange of 50 to 5000 picoliters per cell per day, and 0.02 to 2 pmol $O_2$ per cell per day. In a specific embodiment involving 1000 chromatophores in a 1 $mm^2$ viewing area of a cell chamber, this degree of medium exchange is accomplished by passive diffusion of medium from a bulk volume in which the chamber inlets and outlets are submerged. The feeding requirement can also be accomplished via active fluid flows, conveyed by capillary action or mechanical pumping.

As described for a specific embodiment, upon injection of 100 nM norepinephrine, the analyzer indicated >0.99 probability of a biologically active agent. Similarly, the optical changes occurring in Betta chromatophores upon exposure to bacterial cells and to PC12 cells show that a cytosensor built according to these specified principles and designs is capable of detecting biologically active agents with strong certainty.

EXAMPLE EMBODIMENT 11

Figure 25:
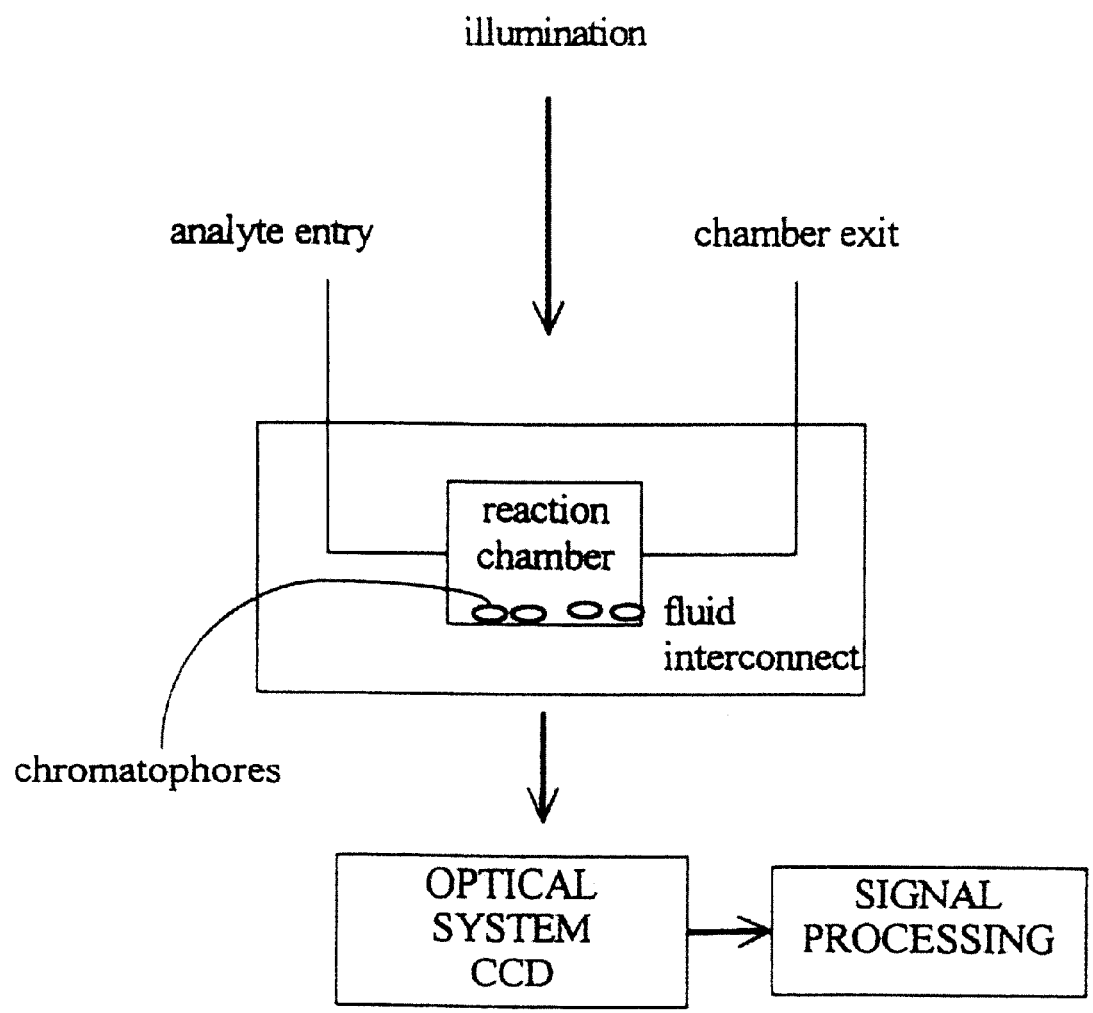
FIG. 25 is a schematic diagram of a cytosensor.

FIG. 25 is a schematic diagram of a cytosensor apparatus that includes an analyte entry tube that delivers an analyte to a reaction cell that contains selected chromatophores. The reaction cell defines a reaction chamber that includes side walls and one or more transparent windows, and the chromatophores are held stationary in the reaction chamber. In a specific embodiment, the analyte entry tubing is 0.25 mm inside diameter TEFLON tubing, and a 1 microliter analyte volume is introduced into the reaction chamber. The analyte can be introduced with a syringe, a syringe pump, a peristaltic pump, or other pump. Alternatively, the analyte can be introduced by wicking with, for example, cellulose fibers, or using a capillary flow.

Chromatophores introduced into the reaction chamber can be retained in the reaction chamber by permitting the chromatophores to settle onto a chamber surface. Superior chromatophore retention is achieved by treating the chamber surface with an attachment factor such as collagen and/or fibronectin. Attachment of the chromatophores is generally adequate 1–24 hr after introduction, and can be verified by observation with a light microscope. After the chromatophores are attached to the If chamber surface, flow rates into and out of the chamber can be increased without dislodging the chromatophores.

Figure 26A:
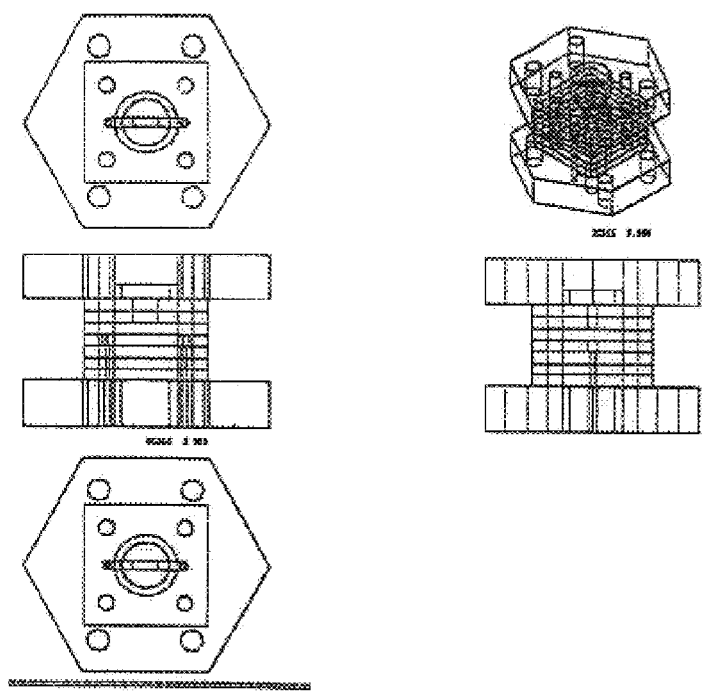
FIGS. 26A–26B illustrate a cell chamber.
Figure 26B:
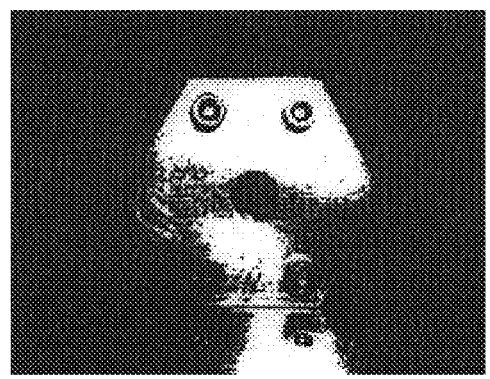

FIGS. 26A–26B illustrate one embodiment of a reaction cell. A reaction chamber is defined in a laminated stack of sheets of a transparent, adhesive-backed material such as MELINEX. The reaction chamber is typically rectangular, with representative dimensions of 2 mm by 3 mm by 0.4 mm. The 0.4 mm depth of the chamber is generally selected as an integer multiple of the thickness of the sheets laminated to form the reaction cell. Inlet and outlet apertures of about 0.5 mm diameter are provided for introduction of and extraction of analytes and other reagents.

As shown in FIG. 26A, the reaction cell is mounted to a fluid interconnect. The fluid interconnect includes a top plate and a bottom plate having central apertures to permit illumination of the chromatophores. These plates are illustrated in FIGS. 27 and 28A–28B. Mounting holes are provided for attaching the fluid interconnect to the reaction cell, and fluid inlets/outlets are provided as well. Bolts (not shown) are used to connect the top and bottom plates, sandwiching the reaction cell.

Figure 29:
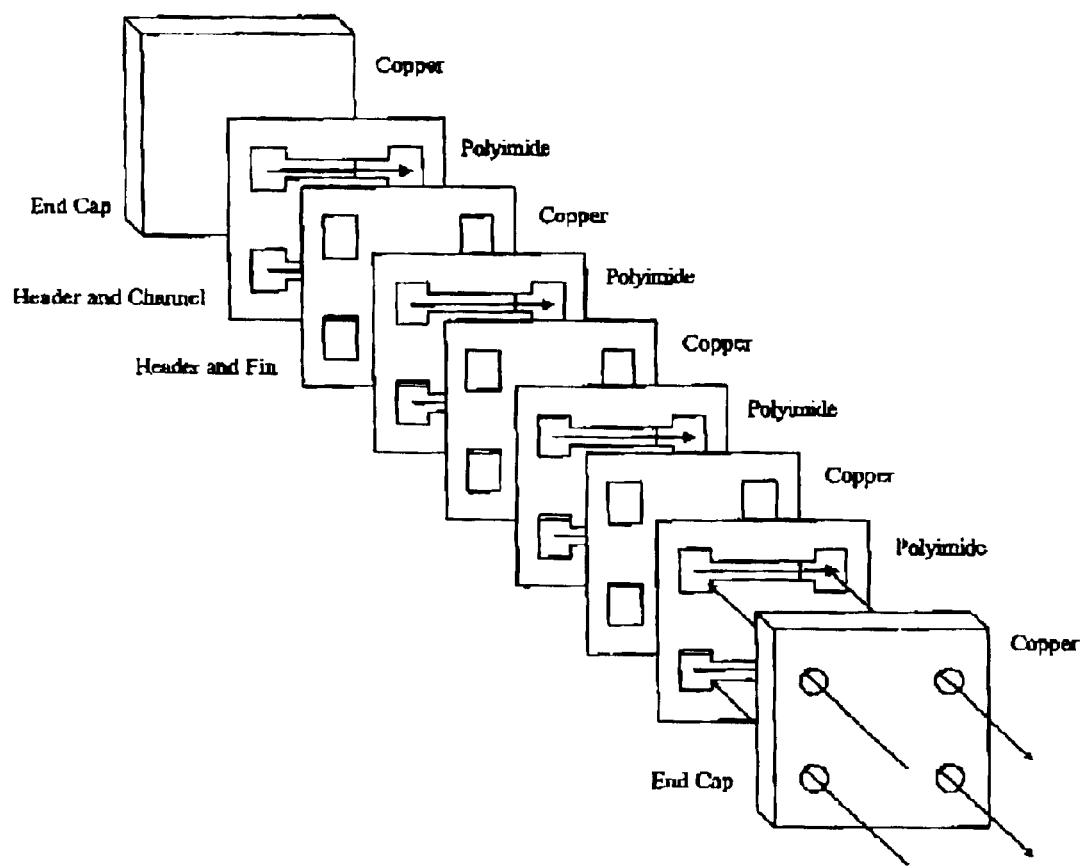
FIG. 29 is a schematic diagram illustrating a microlamination method for defining a cell chamber.

FIG. 29 is a diagram of an alternative reaction cell that defines two reaction chambers. A stack of polyimide layers and copper layers are laminated by heating the stack to that the polyimide layers bond the copper layers. The stack is terminated on a first surface with a first end cap, and on a second surface with a second end cap that includes inlet/output apertures for any necessary analytes or other materials. Reaction cells that include fewer than or more than two reaction chambers can be fabricated similarly.

Figure 30A:
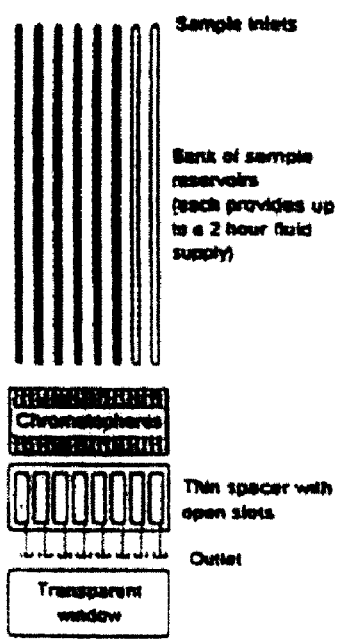
FIGS. 30A–30C are schematic diagrams of multi-analyte reaction cells that include analyte reservoirs.
Figure 30B:
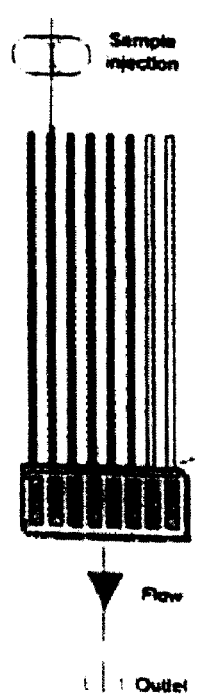
Figure 30C:
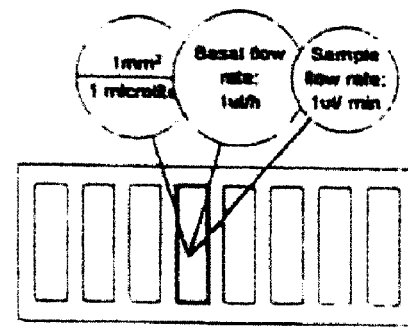
Figure 31:
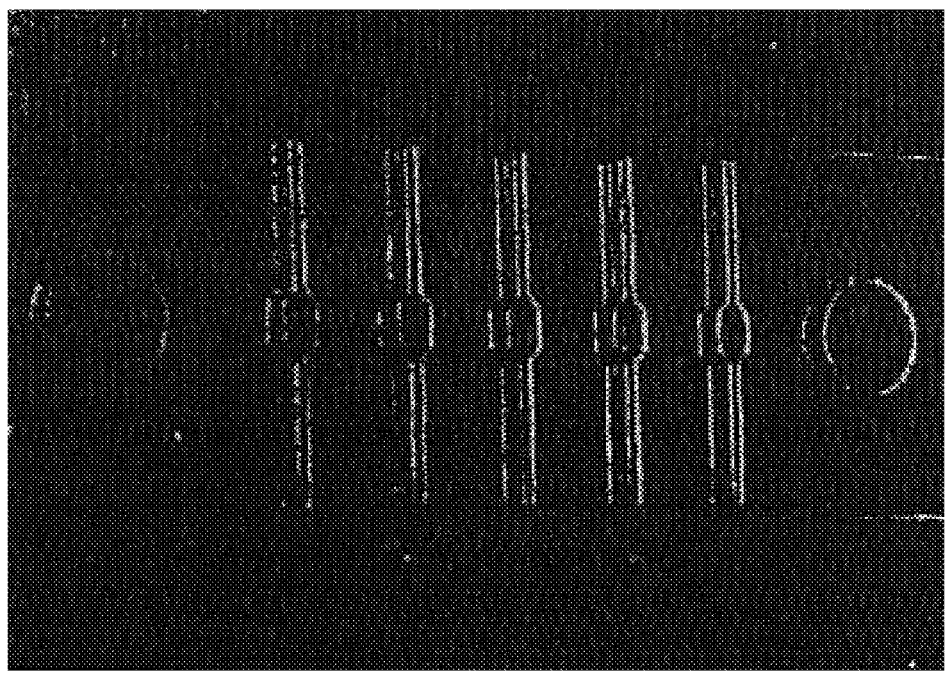
FIG. 31 is a photograph of a mold for a reaction chamber.

FIGS. 30A–30C are schematic diagrams of a multi-analyte reaction cells that include analyte reservoirs and FIG. 31 is photograph of a micromold for fabrication of reaction chambers.

Figure 32:
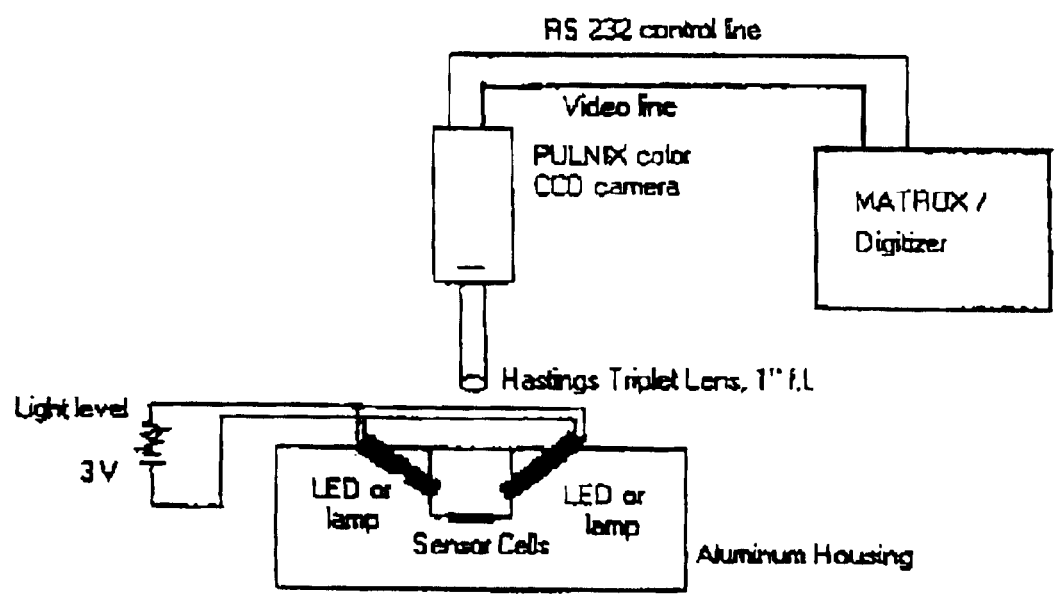
FIG. 32 is a schematic diagram of an optical detection system.

FIG. 32 is a block diagram of an optical apparatus for detecting optical characteristics or changes in such characteristics of chromatophores. One or more light sources such as LEDs, a laser diode or other laser, or lamps are situated to illuminate the chromatophores. In an embodiment, illumination from the light sources is collected with a lens that directs the collected illumination to the chromatophores. Light reflected by or transmitted through the chromatophores is collected with a lens and directed to a imaging system that includes a CCD or other camera Typically, the chromatophores are imaged onto the CCD. The CCD supplies an electrical image signal (typically an analog NTSC video signal) to a digitizer that produces a digital image of the electrical image signal that is supplied to a computer. Alternatively, an image sensor that provides a digital image directly can be used. The computer receives the digital image and stores the digital image in a tagged image file format (TIFF) or other convenient format for processing. Images are generally obtained at a rate of about 2/sec. The apparatus is configurable for measurement of transmitted or reflected light. Typically, transmitted or reflected light is suitable for melanophores, erythrophores, and xanthophores, but for some chromatophores such as iridophores, reflected light is superior. The apparatus is also configurable for measurements of fluorophores.

Images are typically acquired in a red-green-blue (RGB) color representation in which values (r, g, b) for each of the colors R, G, B are assigned to each pixel. Other representations can be used, such as a hue-saturation-intensity representation, or other representations. After conversion into the selected color representation, the image data is segmented into areas corresponding to one or more pre-defined colors or color ranges that are based on the selected chromatophores. A color segment is defined as a predetermined number of adjacent pixels having a color within a predetermined range. This procedure is described in detail below.

In a specific example, the image sensor is a ½" interline transfer CCD color camera Color camera variables include the number of the CCD arrays (e.g. 3-CCD arrays with RGB filters), CCD formats (typically ⅓", ½" and 1"), and resolution (e.g., the number of horizontal and vertical pixels N, M, respectively). For example, a CCD camera can have N=768 columns and M=494 rows of pixels, or 379,392 total pixels. and the CCD cell size is 8.4 $\mu$m (H)×9.8 $\mu$m(V). The camera produces an analog RGB signal that is digitized using a multi-channel frame grabber having sampling rates up to 30 MHz and a data transfer rate of 130 MB/second. A digital color camera can also be used. Such a camera typically has a variable speed shutter (1/60 sec. to 1/10,000 sec.) and can be operated both synchronously and asynchronously.

Figure 33:
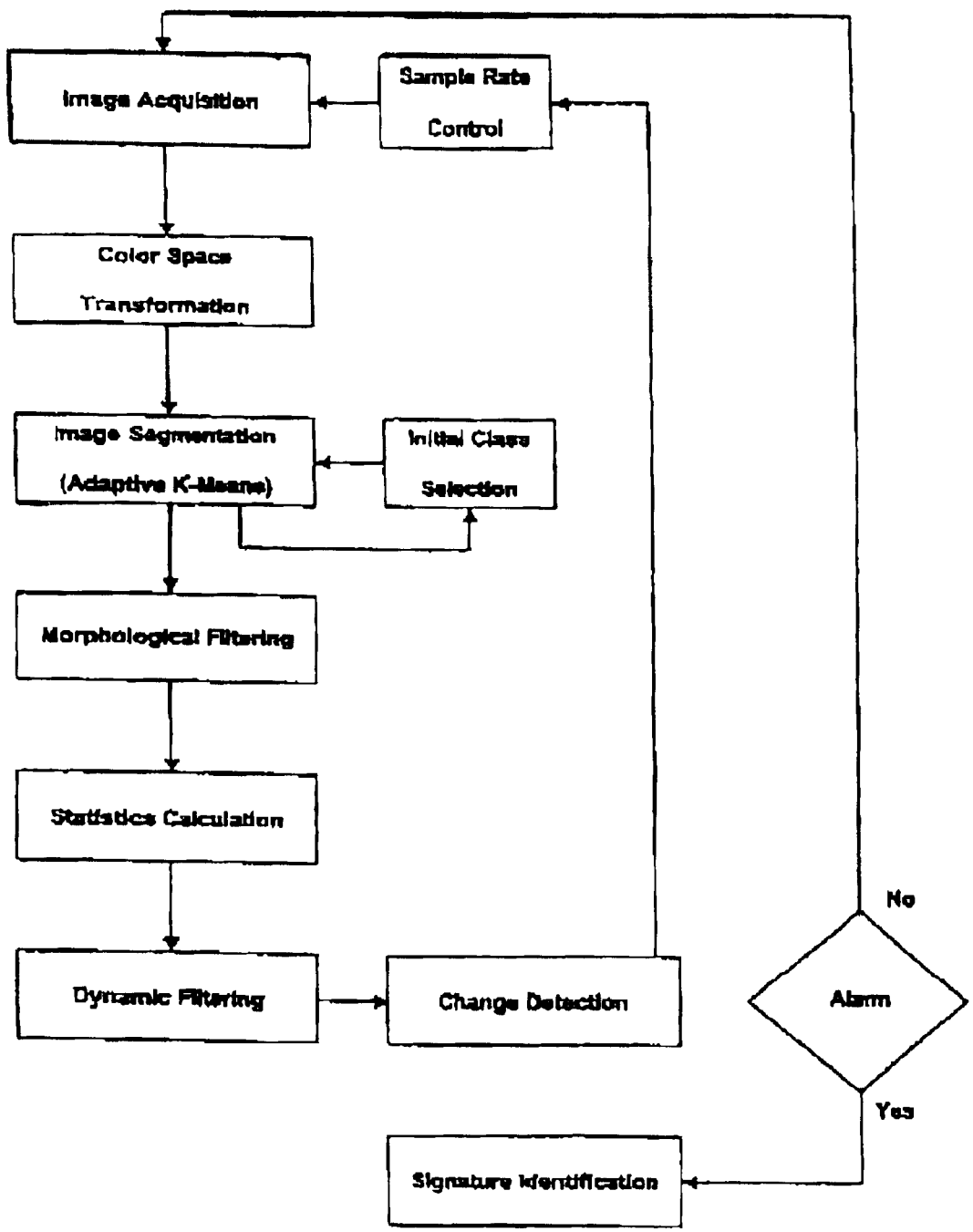
FIG. 33 is a block diagram of a method of analyzing cytosensor data.

FIG. 33 is a block diagram of a method of processing the digital images that uses a time sequence of images acquired either asynchronously or synchronously. Images are typically collected at about one image (frame) per second, but the collection rate is adjusted based on the rates of change of image parameters calculated from previous image and acquisition rates of up to 30 images per second are achievable with conventional image sensors. An optimal acquisition rate can be selected to match the estimated (on-line) rate of change of the image content.

Each image is represented by NxM array A, whose entries are P dimensional vectors. Such an array can be viewed as P dimensional discrete field. N and M define a grid that divides the image into small rectangular regions called pixels or picture elements, e.g., a field of view of dimensions X by Y is divided into pixels (rectangles) of dimensions (X/N) by (Y/M). The P-dimensional discrete field model represents most digital image formats, including the common RGB format. Thus each entry of A represents an average color from a picture element using a P=3 dimensional vector of intensities of red, green and blue color components. Typically these intensities are normalized to take values between 0 and 1. The generalized color histogram can be then viewed as a map of A into a 3 dimensional unit cube. Since the image is a discrete description of the optical appearance of the field of cells, the analyzer can use colors and shapes to characterize the cell state.

In a color space transformation step, the representation of the image in RGB space is transformed to a suitable color space where the distance between colors can be defined to provide, for example, visual uniformity. In an example, a HSV (Hue, Saturation, and Value) space is used.

After color space transformation, an image segmentation step is executed to divide the image into segments based on pixel color. Color segmentation is performed by selecting a specific color coordinate or combination of coordinates, and characterizing pixels based on this coordinate (or coordinates). This process is based on a generalized K-Means algorithm. A color cluster is a set of colors which are "alike," and the colors from different clusters are "not alike." A quantitative description of a cluster is "an aggregation of points in a multi-dimensional space, such that the distance between any two points in the cluster is less than the distance between any point in the cluster and any point not in it". Intuitively clusters are connected regions of a multi-dimensional space containing a relatively high density of points, separated from other such regions by a region of a relatively low density of points. The segmentation takes place in a color histogram space. The distance D is calculated using a quasi-periodic measure based primarily, in a representative example, on the hue coordinate (H) of the image pixels and secondarily, on a contribution based on the saturation coordinate (S). A number of color classes K is adjusted adaptively using dynamic programming techniques. The smallest K is sought such that a color variance (calculated using D) of each of the clusters does not exceed an a priori specified threshold. The dynamic programming method re-uses the initial segmentation for K classes to perform efficiently (K+1) class segmentation. Typically, the image is divided into 5–10 color classes.

After segmentation, the color clusters are associated with their corresponding image (spatial) coordinates for evaluation of cluster geometrical shape in a morphological filtering step. Morphological filtering is applied to each color class to eliminate small spatially isolated clusters and to merge close clusters. For example, morphologically filtered clusters should correspond to the size expected for an image of a chromatophore or a group of chromatophores. The morphologically filtered image contains areas that can be associated with erythrophores, melanophores, and other chromatophores as well as a background. Statistical and morphological parameters of the filtered clusters are calculated in a statistics calculation step. Representative calculated parameters of the color clusters include area, convex hull, bounding polygon, convex area, equivalent diameter, major and minor axis lengths, solidity, extent, orientation, eccentricity, and nth order moments (both spatial using Euclidean distance, and in color space using, for example, the distance D).

In a dynamic filtering step and a change detection step, changes in filtered color clusters are detected based on an analysis of series of images rather than a single image. Dynamic patterns (trends) of selected statistical or other parameters are estimated (for example, area and 2nd order spatial moments), using a conditionally linear filter, which generalizes traditional Kalman filtering methods. This filter tests sequentially two alternative hypotheses about the parameters of a mixture of two distributions. The null hypothesis assumes that there is no bioagent present and that the cells statistics are slowly varying. The alternative hypothesis assumes that after being exposed to a bioagent the cell statistics reach an equilibrium that is distinct from the initial state equilibrium. In a representative example, a mixture of two Gaussian distributions is used having a slowly varying mean and variance and a second having constant moments. The test control parameters include probability of false alarm and detection delay. The acceptance of the second hypothesis marks the end of detection process and stops the image acquisition.

Dynamic patterns are parametrically identified from the statistics waveform in the transition region (i.e. in the non-causal neighborhood of the time instant signaled by the detection algorithm) using, for example, a BARMAX (Bilinear Auto-Regressive Moving Average) model, but various parameterized models can also be used. The estimated model parameters are matched against a stored library of template signatures. These template signatures represent the results of controlled experiments in which chromatophores are exposed to known (type and concentration) bioactive agents. Mercury and Gemini use. Since thus matching problem is of a low dimension (number of model parameters), various statistical (geometric) pattern recognition techniques such as proximity matrix methods can be used here. Some of the cell responses to specific bioactive agents lend themselves to structural (syntactic) pattern recognition. In this all approach the patterns are composed of simple sub-patterns. A sub-pattern can be built from simpler parts with grammatical techniques. Primitives (or the simplest sub-patterns) can be shared among many different experiments to reduce the need for extensive experimentation and the creation of large signature libraries. The outcomes of pattern matching for various statistics represents "votes", defining the confidence level of agent identification.

Such a detection method is implemented on a general-purpose microprocessor such as an embedded Intel Pentium processor running Windows NT or a dedicated processor. Numerical calculations can use fixed-point arithmetic and are suitable for implementation on DSP type boards. The color segmentation algorithm is multi-threaded and can be easily ported to a multi-processor computer or multi DSP chip board. The identification and pattern recognition algorithms have hierarchical organization suitable for communication between several sensors in order to obtain more reliable detection results.

The representation of the cells state as a mathematical field and the general segmentation algorithm allow use of multi-spectral (not necessarily visual) images. Due to the sequential data processing the storage (i.e. memory) requirements are minimal. The system minimizes energy use by adapting the image sampling rates to permit mobile device operation.

Figure 34:
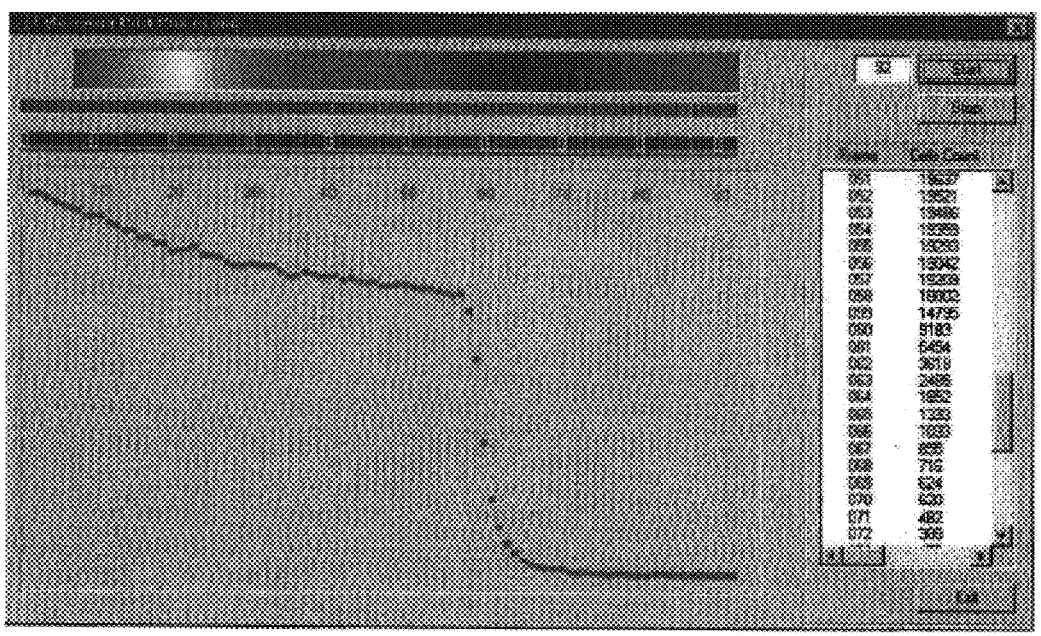
FIG. 34 is a graph illustrating data produced by the method of FIG. 33.

FIG. 34 illustrates results of image processing as described above. The screen image of FIG. 34 is based on 92 images that are acquired at a rate of about 5 images/second. An alarm is triggered at a 60th frame, with a delay of two frames. The signature identification uses 10 frames (from the $58^{th}$ frame to $67^{th}$ frame). Frames 1 to 57 correspond to slowly changing statistics (null hypothesis) and frames 68 to 92 represent equilibrium.

For convenience, FIGS. 5A–5B are provided to illustrate a change in an image hue coordinate after exposure to a selected analyte. While RGB color coordinates change (as shown is FIG. 5A), the change in hue of FIG. 5B is more apparent.

EXAMPLE EMBODIMENT 12

Selective routing of samples through high-throughput screening devices can be used in many applications, including cytosensor methods. Bio-capsules; capture dots; and micro-ball-valves are described in this Example Embodiment.

Micro-balls can be used in biomaterial carriers (capsules containing bio and ferromagnetic material) and in micro-ball valves. Apparatus for the immobilization of biomaterial in alginate beads can be adapted for micro-ball production Several microball compositions have been made and several thousands of micro-balls have been produced. Micro-balls of different sizes, densities, and percent by weight (Wt %) of ferromagnetic material have been produced. Micro-balls having diameters dp in a range of about 150–1000 $\mu$m, ferromagnetic Wt % of about 5%–20%, and densities in a range of about 1.05 g/cm$^3$ to 1.35 g/cm$^3$ have been produced.

Figure 35:
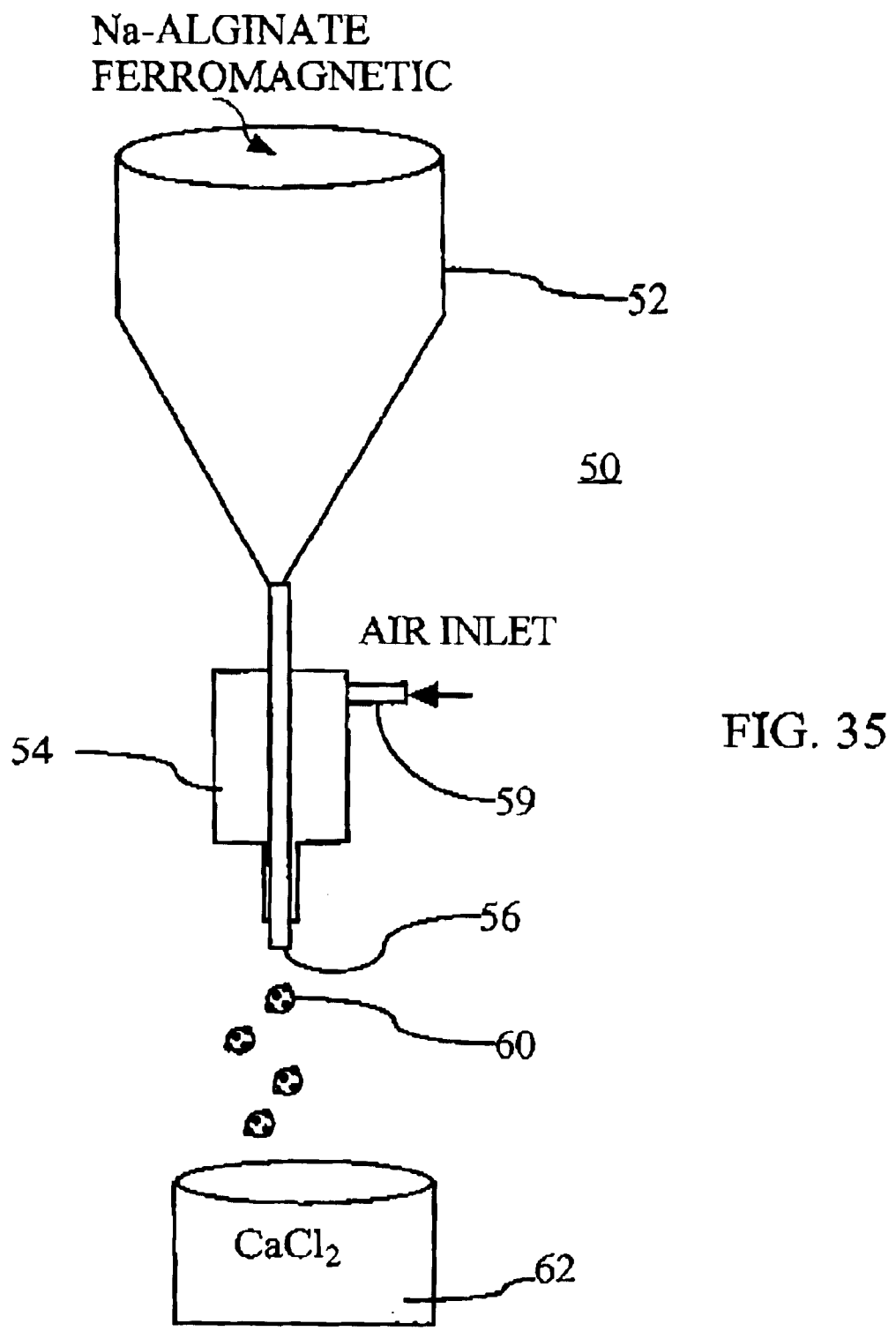
FIG. 35 is a schematic diagram of an encapsulation apparatus.
Figure 36:
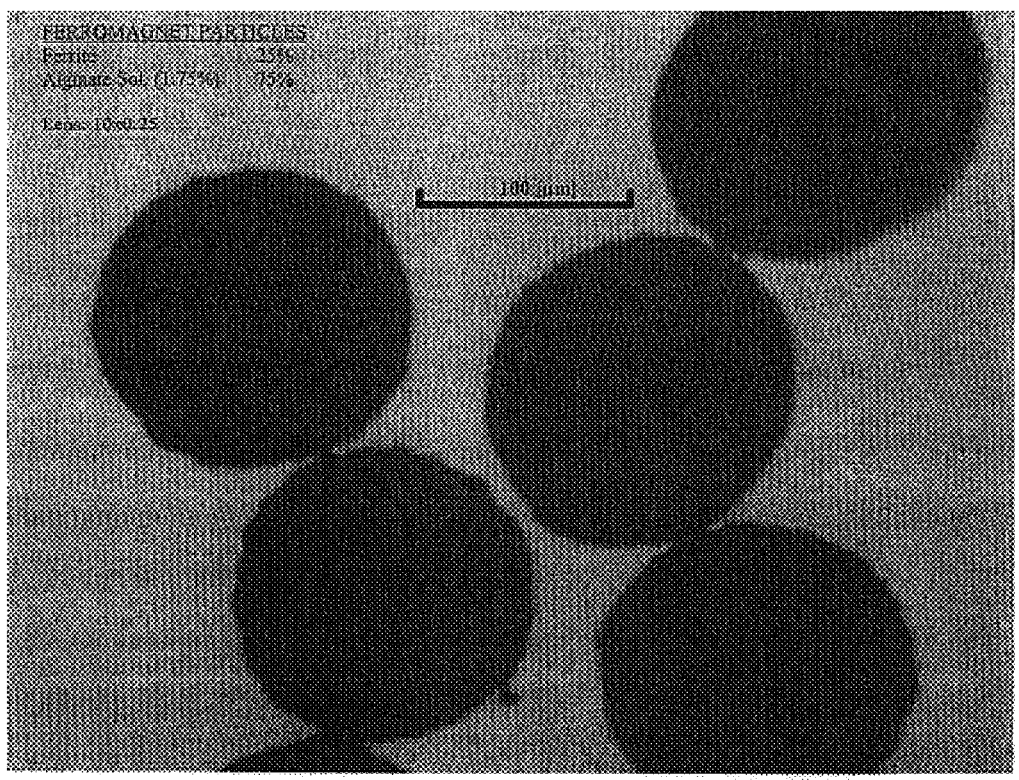
FIG. 36 is a photograph of a ferromagnetic micro-ball.

Micro-ball carriers are preferably in a size range of about 100–200 $\mu$m and can be produced with an extrusion apparatus such as apparatus 51 of FIG. 35. A mixture of 1.5% sodium alginate and 95% water is combined with a ferromagnetic material and an active substance and placed in a reservoir 52. The mixture is directed through a needle 54 or other channel and air is directed to a tip 56 of the needle 54 through an air inlet 58. Introduction of air into the inlet 58 shears off beads 60 at the tip 56. The beads 60 are directed into a CaCl$_2$ bath 62 in which Ca$^{2+}$ is exchanged for sodium ions Na$^+$ so that the alginate material is polymerized. The duration of exposure to the CaCl$_2$ bath determines the degree of polymerization. FIG. 36 is a photograph of several micro-balls (dp≈150 $\mu$m) produced with the apparatus 51.

Figure 37A:
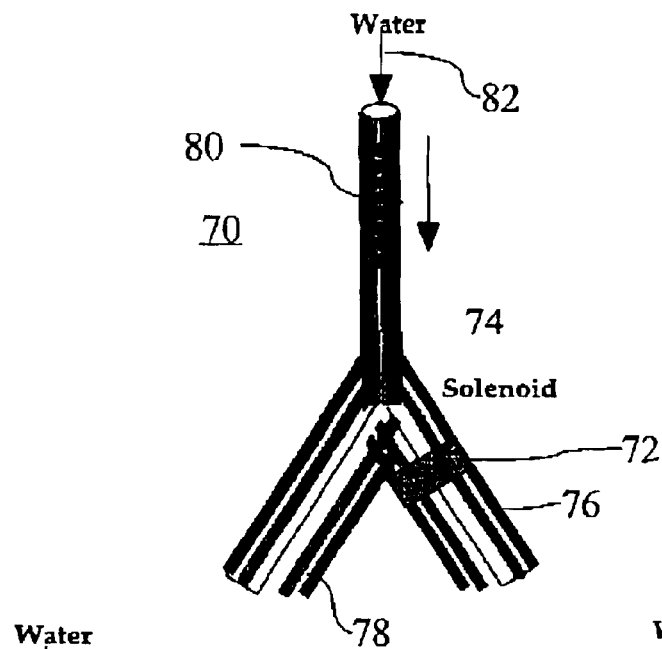
FIGS. 37A–37C illustrate operation of a Y-branch.
Figure 37B:
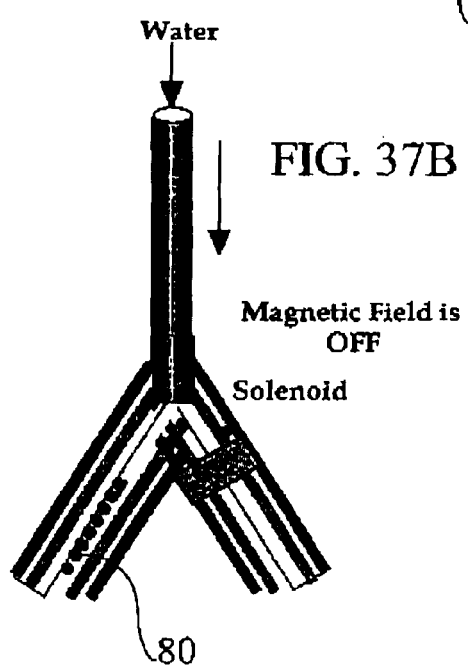
Figure 37C:
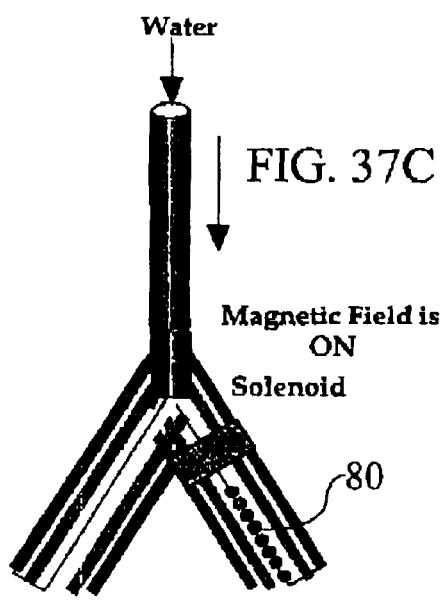

High-throughput screening devices typically require selective immobilization of biomaterial within a maze of micro-channels. Devices incorporating this capability are preferably programmable for a variety of operating configurations. Referring to FIGS. 37A–37C, a Y-branch 70 permits micro-balls containing a ferromagnetic material to be directed to a channel 76 as controlled by a magnetic field generated by a solenoid 72 positioned at an entrance 74 of the channel 76. Micro-balls are directed to one side of the Y-branch 70 by activating a magnetic field for a selected channel (e.g., channels 76, 78). As illustrated in FIG. 37B, with no applied magnetic field (the solenoid 72 in an off state), magnetic particles 80 in a liquid 82 are directed to both channels 76, 78. With an applied magnetic field as shown in FIG. 37C, the particles 80 are directed to the channel 76. In a specific example, micro-balls (the particles 80) of diameter $d_p$=500 μm were directed to a Y-branch having internal diameters of about $d_{ch}$=1000 μm. In other examples, particles of diameter of $d_p \approx 100$ μm were directed into channels of internal diameter $d_{ch} \approx 200$ μm.

Figure 38A:
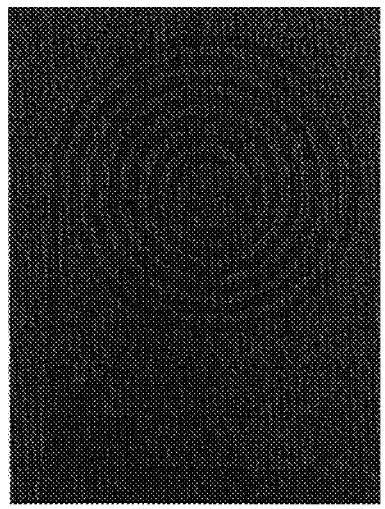
Figure 38B:
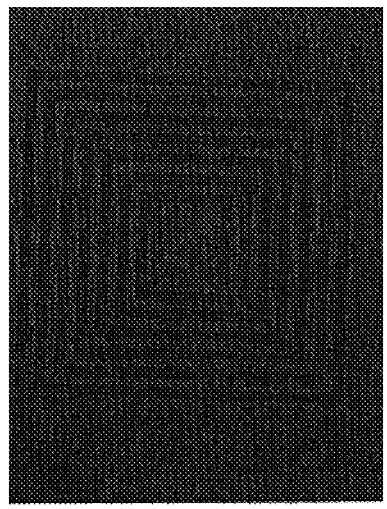
Figure 39:
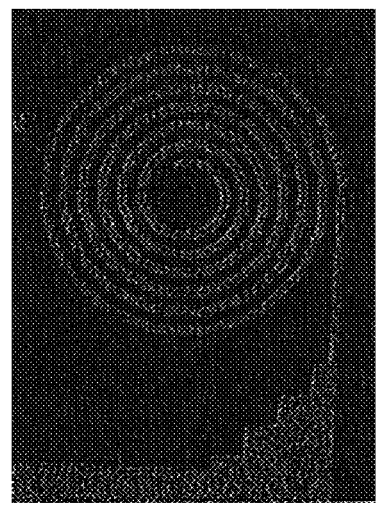
FIG. 39 is a photograph of a coil made using the mask of FIG. 38A.

Detailed calculations of magnetic fields from the thin film coils and magnetic forces on ferromagnetic beads can be used to determine capture dot geometry. Capture dots can be produced by electroforming into a lithographic mold. Round and square coils have been produced using various photolithographic (PL) test patterns. These patterns can include an oxide via to bottom conductor layer, a pad layer for electrical contact, a coiled conductor layer, and a test structure layer. Multiple patterns can be formed on a single mask. Some examples of mask patterns are shown in FIGS. 38A–38B and an electroformed coil made from the pattern of FIG. 38A is shown in FIG. 39.

A method for making contact printing masks for photolithography includes evaporation of a 0.5 μm chromium layer onto a glass microscope slide or other substrate. The chromium layer is selectively ablated using a 532 nm Nd:YAG laser. Because glass ($SiO_2$) is transparent to the 532 nm wavelength, the laser ablates the chromium while leaving the glass surface intact. Linewidths at least as small as 35 μm can be produced. The glass surface is typically somewhat "frosted" indicating that some amount of laser ablation or other effect occurs at the glass surface. Masks can also be made by direct writing with an ultraviolet (UV) on Cr/glass plates or by exposing photoresist/Cr/glass plates for etching of the Cr layer.

Figure 40A:
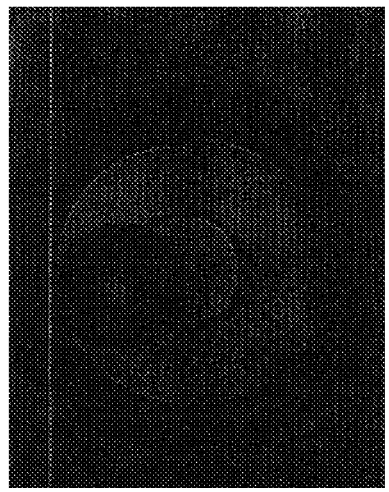
FIGS. 40A–40B are photographs of a micro-ball valve orifice and catch plate, respectively.
Figure 40B:

A two-way micro-ball valve based on capture dots technology for actuating a ferromagnetic ball on the order of several hundred microns can be used. A one-way micro-ball valve is shown in FIGS. 40A–40B. The micro-ball valve includes a valve chamber between a valve orifice (FIG. 40A) and a ball catch plate (FIG. 40B). The device is actuated hydraulically and permits flow in one direction. When flowing from the orifice to the catch plate, the ball is caught in the catch plate allowing flow through the valve. When flowing from the catch plate to the orifice, the ball seals the orifice causing flow to stop. The catch plate thus permits flow through the valve while retaining the ball.

The valve shown in FIGS. 40A–40B defines a chamber of approximately 900 μm diameter and has a glass ball of approximately 400 μm diameter. The valve is made of 9 layers, alternating 0.005 inch MELINEX 453 polyester film with Avery Dennison FT8311 double-sided pressure sensitive adhesive film. There are four FT8311 laminae interspersed between five MELINEX laminae. The two outside laminae are patterned as shown with the orifice and catch plate. The inner laminae are patterned with a circle of the diameter of the valve.

Several one-way valves similar to those of FIGS. 40A–40B were built and tested. Leakage within a diode (one-way) valve can be quantified as a diodicity (i.e. a ratio of pressure required to give an intended flow rate in a first direction to the pressure required to create the same flow rate in a second direction, opposite the first (an undesired flow direction). Table 2 summarizes the diodicity results from a particular valve.

TABLE 2

Micro-ball Valve Diodicity

| Flow rate (ml/min) | Forward flow Pressure (psi) | Reverse flow Pressure (psi) | Diodicity |
|---|---|---|---|
| 5 | 1.05 | 0.37 | 2.84 |
| 8 | 1.48 | 0.95 | 1.56 |
| 9 | 1.6 | 1.12 | 1.43 |
| 10 | 2.96 | 1.4 | 2.11 |

Figure 41:
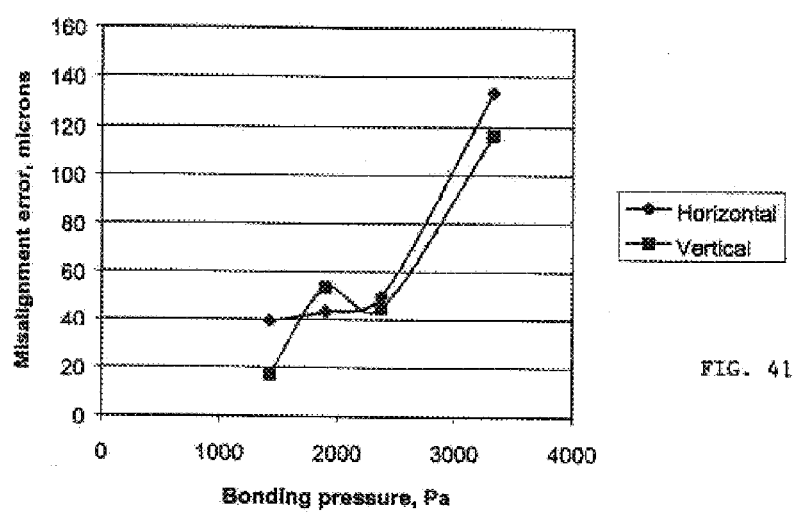
FIG. 41 is a graph of misalignment error as a function of bonding pressure.

The diodicity of this valve is limited by alignment errors between layers that prevent the ball from sealing the orifice. Misalignment as a function of bonding pressure was measured and is graphed in FIG. 41.

In other examples, adhesive appeared within the chamber causing the ball to stick as the pressure sensitive adhesive oozes under high bonding pressures. Therefore, the design for the middle chamber laminae was changed so that the circles cut in the FT8311 laminae for the chamber were larger than the circles cut in the MELINEX laminae. This was done to keep the ball from being exposed to any excess adhesive that might be squeezed out from between laminae. In addition, misalignment can still occur and alignment holes were provided to reduce misalignment. Use of a 266 nm Nd:YAG laser for patterning MELINEX layers and FT8311 laminae reduces thermal damage and improves chamber geometry.

Figure 42:
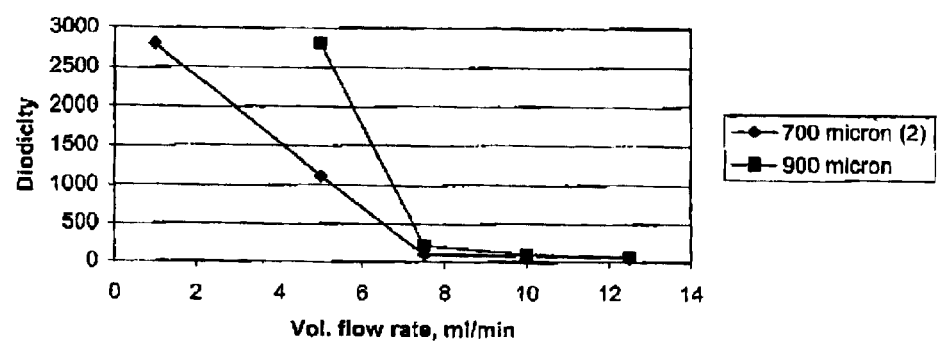
FIG. 42 is a graph of diodicity as a function of flow rate for micro-ball valves.
Figure 43A:
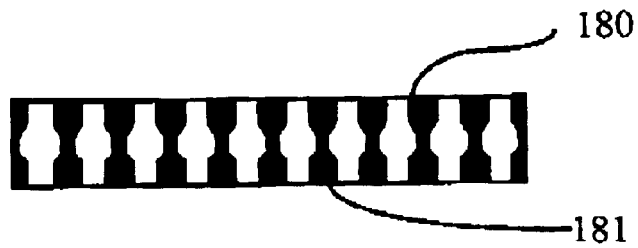
FIG. 43A–43E illustrate construction of a channel assembly.
Figure 43B:
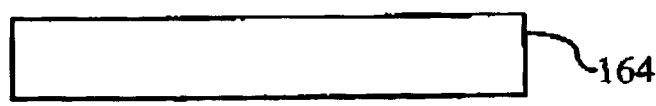
Figure 43C:
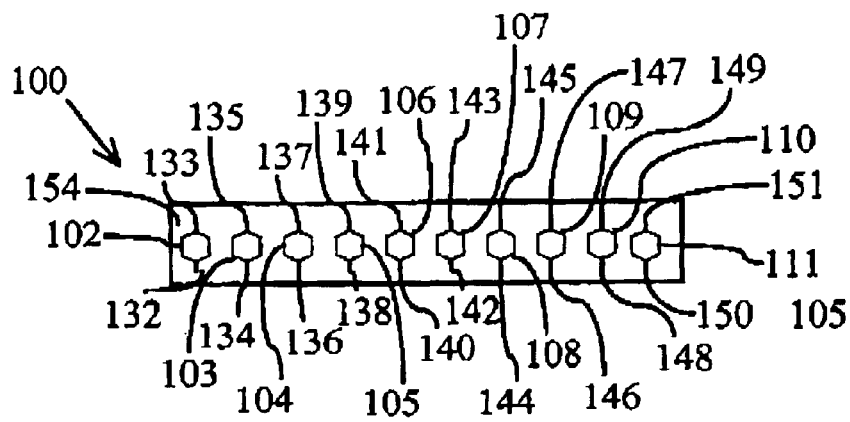
Figure 43D:
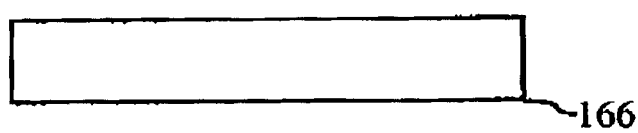
Figure 43E:
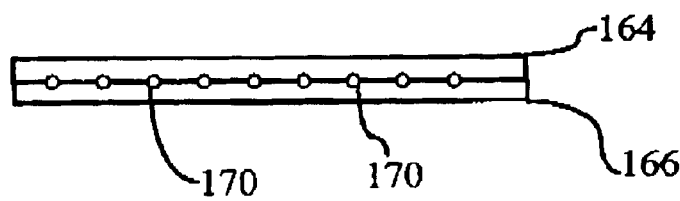

Valve performance with these improvements is illustrated in Table 3 and FIG. 42. All reverse flow pressure drops in Table 3 are 28 psi, limited by a pressure gauge in a measurement system. Therefore, diodicity for the valve at the tabulated flow rates is at least about 2,800. Leakage between the glass ball and the polyester orifice be less than 10 microliters/min at 28 psi. Such valves can include magnetic balls so that the valves are electromagnetically activated.

TABLE 3

Micro-ball Valve Diodicity

| Flow rate (ml/min) | Forward flow Pressure (psi) | Reverse flow Pressure (psi) | Diodicity |
|---|---|---|---|
| Valve diameter = 700 microns | | | |
| 1 | <0.01 | 28 | >2800 |
| 5 | 0.025 | 28 | 1120.0 |
| 7.5 | 0.3 | 28 | 93.3 |
| 10 | 0.305 | 28 | 91.8 |
| 12.5 | 0.52 | 28 | 53.8 |
| Valve diameter = 900 microns | | | |
| 5 | <0.01 | 28 | >2800 |
| 7.5 | 0.13 | 28 | 215.4 |
| 10 | 0.27 | 28 | 103.7 |
| 12.5 | 0.45 | 28 | 62.2 |

EXAMPLE EMBODIMENT 13

Cytosensor chambers can be formed using conventional machining, laser machining, photolithographic processes, or other methods. Referring to FIGS. 1A–1E, a chamber array 100 includes chambers 102–111 that are defined by recesses in a polycarbonate plate 121. The chambers 102–111 are provided with channels 132–151 that extend toward edges 152, 154 of the plate 121. A chamber assembly 160 includes the plate 121, a top plate 164, and a bottom plate 166, The top plate 164 and the bottom plate 166 are attached to the plate 121 by sonic welding, an adhesive, or with solvent welding. In one example, the plate 121 is exposed to a mixture of methylene chloride, methyl alcohol, and toluene. After exposure, the mixture is blown from the plate 121 and the plate 121 is contacted to the top plate 164 and the bottom plate 166. The plates 121, 164, 166 are pressed together for bonding and can be conveniently aligned using alignment holes configured to fit on an alignment pin made from, for example, drill rod or other material. After bonding, the chamber assembly 160 can be treated to eliminate any solvent residue by heat treating, or other method.

Fluid ports 170 extend from the chambers 102–111 to sides 180, 181 for fluid entry and discharge. The fluid ports 170 can be formed by boring holes from the sides 180 to the channels 132–151. Fluid connection to the channels 132–151 can be made by inserting tubing such as microchannel tubing into the holes so that a leak free seal is formed. Capillary action or gravity can be used to direct fluids into one or more of the chambers through the tubing. In some examples, one of either the top plate or the bottom plate is white polycarbonate to enhance viewing of chromatophores. Typically the top plate is clear to permit viewing contents of the chambers, but some plates can be made of clear or black polycarbonate or other materials.

The invention is described above with reference to example embodiments. It will be apparent to those skilled in the art that these examples can be altered in arrangement and detail without departing from the scope of the invention. We claim all that is encompassed by the appended claims.

We claim:

1. A method for detecting a bioactive compound or organism, comprising:
   providing at least one bead comprising chromatophores in a first optical state;
   commingling the bioactive compound or organism with the chromatophores; and
   detecting an optical change in at least one chromatophore from the first optical state to a second optical state in response to the bioactive compound or organism.

2. The method of claim 1, wherein the chromatophores are fish chromatophores and an optical change in the at least one chromatophore is selected from a group consisting of pigment aggregation, pigment dispersion, and hue changes.

3. The method of claim 1, wherein the bioactive compound is selected from a group consisting of neurotransmitters, adrenergic agonists, adrenergic antagonists, seratonergic antagonists, hormones, cytoskeletal inhibitors, cAMP Signal transduction modulators, calcium ion signal transduction modulators, membrane voltage regulators, neurotoxins, protein kinase modulators, caustic irritants, heavy metals, polyaromatic hydrocarbons, organo phosphate nerve agents, psychogenic agents, antihistamines, enzyme inhibitors, algal toxins, bacteria, and bacterial protein toxins.

4. The method of claim 1, wherein the organism includes a bacteria, fungus, virus, plant, or animal.

5. The method of claim 1, wherein the chromatophores are Betta chromatophores.

6. The method according to claim 1, comprising:
   exposing a first type of chromatophore to a sample potentially comprising a bioactive compound or organism;
   exposing a second type of chromatophore to a sample potentially comprising a bioactive compound or organism; and
   identifying at least one class of compounds by comparing an optical appearance of the first type of chromatophore and the second type of chromatophore prior to exposure to the bioactive compound or organism and after exposure to the bioactive compound.

7. The method of claim 6, wherein the first and second types of chromatophore are melanophores and erythrophores, respectively.

8. The method of claim 7, wherein the chromatophores are fish chromatophores.

9. The method of claim 1 useful for identifying a calcium channel blocker, comprising:
   exposing an erythrophore chromatophore and a melanophore chromatophore to a known calcium channel blocker, thereby producing a known response to the calcium channel blocker;
   exposing the erythrophore chromatophore to a sample potentially comprising a calcium channel blocker;
   exposing the melanophore chromatophore to the sample; and
   determining that the sample includes a calcium channel blocker based on an erythrophore dispersion response and no melanophore response.

10. The method of claim 1 where the chromatophores have a first color prior to commingling the bioactive compound or organism with the chromatophores and a second color after commingling the bioactive compound or organism with the chromatophores, the method further comprising detecting a color change from the first color to the second color of at least one chromatophore.

11. The method of claim 10, further comprising determining if a test sample includes a compound selected from a group consisting of neurotransmitters, hormones, intracellular signal transduction agents, pharmaceutically active agents, toxic agents, agricultural chemicals, chemical toxins, biological toxins, microbes, and animal cells based on the color change.

12. The method of claim 1 further comprising:
   selecting a bacteria that produces a bacterial-induced response on the at least one chromatophore;
   exposing a combination of the at least one chromatophore and the bacteria to the bioactive compound;
   exposing the combination to a control compound selected based on a control response produced on the chromatophore;
   determining a measured response of the chromatophore to the exposure of the combination to the control compound; and
   evaluating the bioactive compound based on a difference in the measured response, the bacterial-induced response, and the control response.

13. The method of claim 12, wherein the control compound is norepinephrine.

14. The method according to claim 1 where the at least one bead is formed from glass or polymeric material.

15. The method according to claim 14 where the polymeric material is alginate.

16. A method for detecting a bioactive compound or organism, comprising:
   providing at least one bead comprising Betta chromatophores in a first optical state;
   exposing the Betta chromatophores in the first optical state to the bioactive compound or organism; and
   detecting an optical change in at least one Betta chromatophore from the first optical state to a second optical state in response to the bioactive compound or organism.

17. The method according to claim 16 where exposing comprises exposing two or more classes of *Betta splendens* chromatophores to the bioactive compound or organism.

18. The method according to claim 17 where the *Betta splendens* chromatophores are isolated chromatophores.

19. The method according to claim 16 and further comprising exposing the bioactive compound or organism to chromatophores in addition to the Betta chromatophores.

20. A method for detecting a bioactive compound or organism, comprising:

providing at least one bead comprising isolated chromatophores;

exposing the isolated chromatophores to a bioactive compound or organism; and quantifying a scalar optical change in at least one chromatophore in response to the bioactive compound.

21. A method for detecting a bioactive compound or organism, comprising:

providing beads comprising two or more types of isolated, primary *Betta splendens* chromatophores;

commingling the bioactive compound or organism with the chromatophores; and detecting a scalar optical change in at least one chromatophore in response to the bioactive compound or organism.

22. The method according to claim 21 where detecting the scalar optical change comprises computer aided detection.

* * * * *